(12) United States Patent
Thompson et al.

(10) Patent No.: US 7,452,893 B2
(45) Date of Patent: Nov. 18, 2008

(54) 4-CYCLOAKYLAMINOPYRAZOLO PYRIMIDINE NMDA/NR2B ANTAGONISTS

(75) Inventors: Wayne Thompson, Landsdale, PA (US); Steven D. Young, Lansdale, PA (US); Brian T. Phillips, Telford, PA (US); Peter Munson, Harleysville, PA (US); Willie Whitter, West Point, PA (US); Nigel Liverton, Harleysville, PA (US); Christine Dieckhaus, North Wales, PA (US); John Butcher, Telford, PA (US); John A. McCauley, Maple Glen, PA (US); Charles J. McIntyre, Lansdale, PA (US); Mark E. Layton, Harleysville, PA (US); Philip E. Sanderson, Valley Forge, PA (US)

(73) Assignee: Merck & Co., Inc., Rahway, NJ (US)

( * ) Notice: Subject to any disclaimer, the term of this patent is extended or adjusted under 35 U.S.C. 154(b) by 237 days.

(21) Appl. No.: 10/568,470

(22) PCT Filed: Aug. 11, 2004

(86) PCT No.: PCT/US2004/025961

§ 371 (c)(1),
(2), (4) Date: Feb. 14, 2006

(87) PCT Pub. No.: WO2005/019221

PCT Pub. Date: Mar. 3, 2005

(65) Prior Publication Data

US 2007/0037829 A1    Feb. 15, 2007

Related U.S. Application Data

(60) Provisional application No. 60/495,650, filed on Aug. 15, 2003.

(51) Int. Cl.
*C07D 487/04* (2006.01)
*A61K 31/519* (2006.01)
(52) U.S. Cl. .................. 514/262.1; 544/262
(58) Field of Classification Search ............ 544/262; 514/262.1
See application file for complete search history.

(56) References Cited

U.S. PATENT DOCUMENTS

| 4,904,666 | A | 2/1990 | Friebe et al. |
| 5,723,608 | A | 3/1998 | Yuan |
| 2005/0054658 | A1 | 3/2005 | Thompson et al. |

FOREIGN PATENT DOCUMENTS

| EP | 0 641 781 A | 3/1995 |
| EP | 0 729 758 A | 9/1996 |
| WO | WO 98/35048 A | 8/1998 |
| WO | WO 01/23389 | 4/2001 |

OTHER PUBLICATIONS

Anthony C. Bishop, et al. "Design of allele-specific inhibitors to probe protein kinase signaling" Current Biology, vol. 8, No. 5, 1998, pp. 257-266.
McCauley (Expert Opin. Ther. Patents, 2005, 15(4), 389-407).
Alden, P., HIV and the central nervous system, The Bay Area Reporter, Jun. 16, 2000, <http://www.aegis.org/news/bar/2000/BR000605.html> dowloaded on Jan. 22, 2007.
Robins, Roland K., J. Am. Chem. Soc., vol. 79, pp. 6407-6415, 1957.
Hamilton, Harriet W., Bristol, James A.: J. Med. Chem., vol. 26, pp. 1601-1606, 1983.
Rideout, Janet L., Krenitsky, Thomas A., Koszalka, George W., Cohn, Naomi K., et al.—J. Med. Chem., vol. 25, pp. 1040-1044, 1982.

*Primary Examiner*—Bruck Kifle
(74) *Attorney, Agent, or Firm*—William Krovatin; John C. Todaro

(57) ABSTRACT

Compounds represented by Formula (I) or pharmaceutically acceptable salts thereof, are effective as NMDA/NR2B antagonists useful for treating neurological conditions such as, for example, pain, Parkinson's disease, Alzheimer's disease, epilepsy, depression, anxiety, ischemic brain injury including stroke, and other conditions.

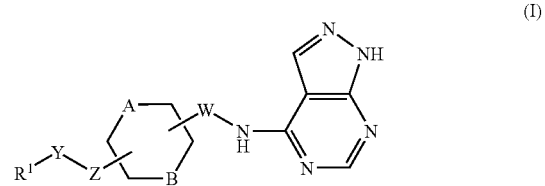

9 Claims, No Drawings

4-CYCLOAKYLAMINOPYRAZOLO PYRIMIDINE NMDA/NR2B ANTAGONISTS

RELATED APPLICATION DATA

This is a National filing under 35 USC 371 of PCT/US04/025961 filed Aug. 11, 2004, which claims priority from U.S. Ser. No. 60/495,650, filed Aug. 15, 2003.

FIELD OF THE INVENTION

This invention relates to 4-cycloalkylaminopyrazolo pyrimidine compounds. In particular, this invention relates to 4-cycloalkylaminopyrazolo pyrimidine compounds that are NMDA/NR2B antagonists useful for the treatment of neurological conditions such as pain, Parkinson's disease, Alzheimer's disease, epilepsy, depression, anxiety, ischemic brain injury including stroke, and other conditions.

BACKGROUND OF THE INVENTION

Ions such as glutamate play a key role in processes related to chronic pain and pain-associated neurotoxicity—primarily by acting through N-methyl-D-aspartate ("NMDA") receptors. Thus, inhibition of such action—by employing ion channel antagonists, particularly NMDA antagonists—can be beneficial in the treatment and control of Parkinon's disease and pain.

NMDA receptors are heteromeric assemblies of subunits, of which two major subunit families designated NR1 and NR2 have been cloned. Without being bound by theory, it is generally believed that the various functional NMDA receptors in the mammalian central nervous system ("CNS") are only formed by combinations of NR1 and NR2 subunits, which respectively express glycine and glutamate recognition sites. The NR2 subunit family is in turn divided into four individual subunit types: NR2A, NR2B, NR2C, and NR2D. T. Ishii, et al., *J. Biol. Chem.*, 268:2836-2843 (1993), and D. J. Laurie et al., *Mol. Brain Res.*, 51:23-32 (1997) describe how the various resulting combinations produce a variety of NMDA receptors differing in physiological and pharmacological properties such as ion gating properties, magnesium sensitivity, pharmacological profile, as well as in anatomical distribution.

For example, while NR1 is found throughout the brain, NR2 subunits are differentially distributed. In particular, it is believed that the distribution map for NR2B lowers the probability of side effects while treating Parkinson's disease or pain. Thus, it would be desirable to provide novel NMDA antagonists that target the NR2B receptor.

SUMMARY OF THE INVENTION

The present invention relates to 4-cycloalkylaminopyrazolo pyrimidine compounds represented by Formula (I):

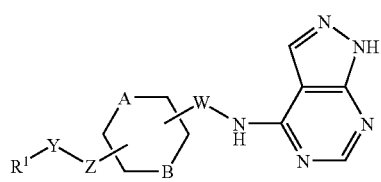

or pharmaceutically acceptable salts thereof. The present invention also provides pharmaceutical compositions comprising the instant compounds. This invention further provides methods to treat and prevent neurological conditions, including pain, Parkinson's disease, Alzheimer's disease, epilepsy, depression, anxiety, ischemic brain injury including stroke, and other conditions, utilizing the present compounds and compositions.

DETAILED DESCRIPTION OF THE INVENTION

The compounds of this invention are represented by Formula (I):

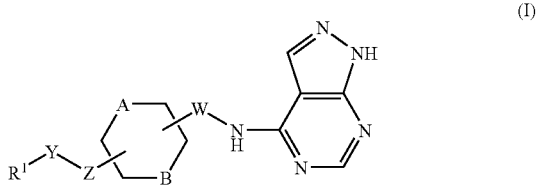

and pharmaceutically acceptable salts thereof, and individual and diastereomers thereof, wherein:

$R^1$ is selected from:

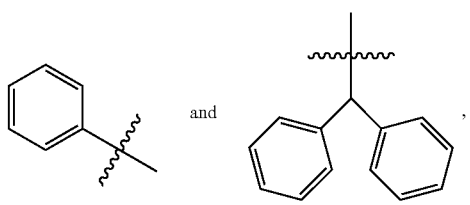

unsubstituted or substituted with one or more substituents selected from: halogen, —$R^2$, —O—$R^2$, —CN, —N($R^2$)$_2$, Y is selected from:

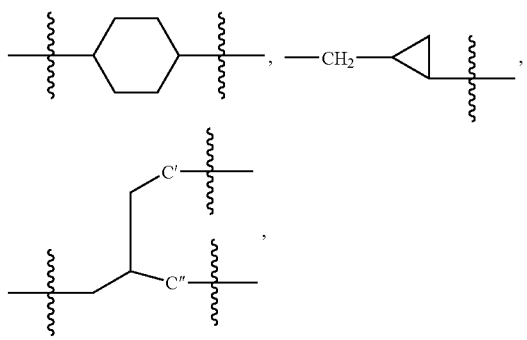

—$R^3$— and —$R^3$—O—$R^3$—, where C' and C" are each independently directly or indirectly bound to $R^1$ to form a 5 to 7 member fused ring;

Z is absent or is selected from O, $C_{1-6}$alkyl, $C_{1-6}$alkenyl, C(O), S, SO, SO$_2$, NR$^4$, where R$^4$ is $C_{0-6}$alkyl or $C_{0-6}$alkenyl, where said alkyl or alkenyl is unsubstituted or is substituted with one or more substituents selected from: halogen, —$R^5$, —O—$R^5$, —CN, —N($R^5$)$_2$;

A and B are each independently $C_{0-4}$alkyl, where a ring is formed comprising A and B, where an individual carbon atom in A and an individual carbon atom in B optionally bridge said ring, where each member of said ring is independently unsubstituted or substituted with one or more substituents selected from halogen, —$R^6$, —O—$R^6$, —CN, —N($R^6$)$_2$;

W is absent or is selected from from O, $C_{0-6}$alkyl, $C_{0-6}$alkenyl, C(O), S, SO, SO$_2$, N$R^7$, where said alkyl or alkenyl is unsubstituted or is substituted with one or more substituents selected from halogen, —$R^8$, —O—$R^8$, —CN, —N($R^8$)$_2$;

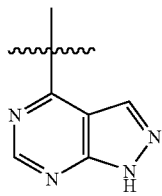

is unsubstituted or is substituted with one or more substituents selected from halogen, —$R^9$, —O—$R^9$, —CN, —N($R^9$)$_2$; and, $R^2$, $R^3$, $R^4$, $R^5$, $R^6$, $R^7$, $R^8$ and $R^9$ are each independently hydrogen, $C_{0-6}$alkyl, $C_{0-6}$alkenyl unsubstituted or substituted with one or more halogen.

In one embodiment, the compounds of this invention are represented by Formula (I), wherein:
$R^1$ is

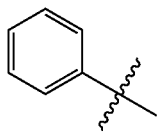

unsubstituted or substituted with halogen or —$R^2$, where $R^2$ is $C_{1-6}$alkyl;

Y is —$C_{1-6}$alkyl, independently unsubstituted or substituted with one or more halogen;

Z is O;

A and B are each independently $C_{0-4}$alkyl;

W is absent;

and pharmaceutically acceptable salts thereof and individual enantiomers and diastereomers thereof.

In another embodiment, the compounds of this invention are represented by Formula (Ia):

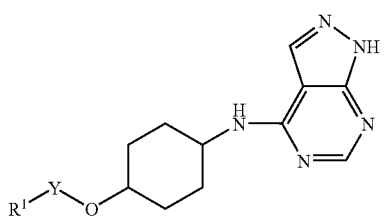

(Ia)

wherein:
$R^1$ is

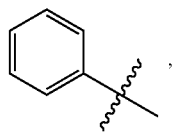

unsubstituted or substituted with halogen or —$R^2$, where $R^2$ is $C_{1-6}$alkyl, independently unsubstituted or substituted with one or more halogen;

Y is —$C_{1-6}$alkyl, independently unsubstituted or substituted with one or more halogen;

and pharmaceutically acceptable salts thereof and individual enantiomers and diastereomers thereof.

In yet another embodiment, the compounds of this invention are represented by Formula (Ib):

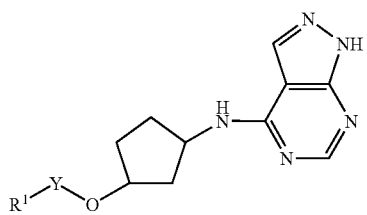

(Ib)

wherein:
$R^1$ is

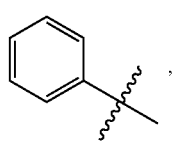

unsubstituted or substituted with halogen or —$R^2$, where $R^2$ is $C_{1-6}$alkyl, unsubstituted or substituted with one or more halogen;

the cyclopentyl group is unsubstituted or substituted with 1-3 fluorine;

Y is —$C_{1-6}$alkyl, unsubstituted or substituted with one or more halogen;

and pharmaceutically acceptable salts thereof and individual enantiomers and diastereomers thereof.

In still another embodiment, the compounds of this invention are represented by Formula (Ic):

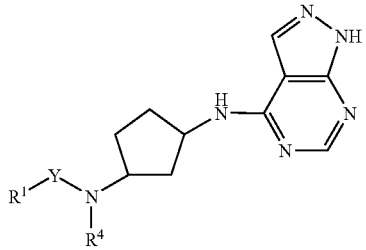

(Ic)

wherein:

R$^1$ is

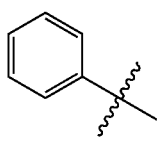

unsubstituted or substituted with halogen or —R$^2$, where R$^2$ is C$_{1-6}$alkyl, unsubstituted or substituted with one or more halogen;

R$^4$ is hydrogen or C$_{0-6}$alkyl unsubstituted or substituted with one or more halogen;

the cyclopentyl group is unsubstituted or substituted with 1-3 fluorine;

Y is —C$_{1-6}$alkyl, unsubstituted or substituted with one or more halogen;

and pharmaceutically acceptable salts thereof and individual enantiomers and diastereomers thereof.

As used herein, "alkyl" as well as other terms having the prefix "alk" such as, for example, alkoxy, alkanoyl, alkenyl, alkynyl and the like, means carbon chains which may be linear or branched or combinations thereof. Examples of alkyl groups include methyl, ethyl, propyl, isopropyl, butyl, sec- and tert-butyl, pentyl, hexyl, heptyl and the like.

The term "aryl", unless specifically stated otherwise, includes optionally substituted multiple and single ring systems such as, for example, phenyl, naphthyl and tolyl.

In the structures depicted throughout this application a hydrogen atom on an unsubstituted nitrogen atom may be either expressly shown or implicit. For example, the Formula I structure depicted above (with hydrogen atoms at two of the nitrogen atoms) may also be depicted as:

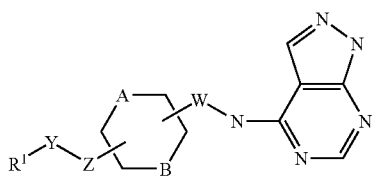

The same convention also applies to Formula Ia and Ib, and to all other generic structures and structures depicting individual species. Of course, nitrogen atoms may also be substituted with atoms and/or moieties other than hydrogen, as set forth elsewhere in this application.

Further, multiple enantiomers be depicted to describe the same compound. Thus, the Formula I structure can alternately be depicted as follows:

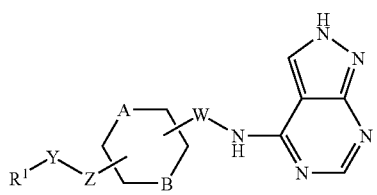

The term "HetAr" includes, for example, heteroaromatic rings such as pyrimidine and pyridine.

The term "(CH$_2$)$_0$" means that the methyl is not present. Thus, "(CH$_2$)$_{0-3}$" means that there are from none to three methyls present—that is, three, two, one, or no methyl present. When no methyl groups are present in a linking alkyl group, the link is a direct bond.

As appreciated by those of skill in the art, halo or halogen as used herein are intended to include chloro, fluoro, bromo and iodo. Similarly, C$_{1-6}$, as in C$_{1-8}$alkyl is defined to identify the group as having 1, 2, 3, 4, 5 or 6 carbons in a linear or branched arrangement, such that C$_{1-6}$alkyl specifically includes methyl, ethyl, n-propyl, iso-propyl, n-butyl, iso-butyl, tert-butyl, pentyl, and hexyl. Likewise, C$_0$, as in C$_0$alkyl is defined to identify the presence of a direct covalent bond (or hydrogen).

The term "substituted" is intended to include substitution at any or all position. Thus, substitution can be made at any of the groups. For example, substituted aryl(C$_{1-6}$)alkyl includes substitution on the aryl group as well as substitution on the alkyl group.

Compounds described herein may contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. Formula I (including Formulae Ia, Ib) is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

The term "pharmaceutically acceptable salts" refers to salts prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric, and tartaric acids.

The subject treated in the present methods is generally a mammal, preferably a human being, male or female, in whom antagonism of CGRP receptor activity is desired. The term "therapeutically effective amount" means the amount of the subject compound that will elicit the biological or medical response of a tissue, system, animal or human that is being sought by the researcher, veterinarian, medical doctor or other clinician. As used herein, the term "treatment" refers both to the treatment and to the prevention or prophylactic therapy of the mentioned conditions, particularly in a patient who is predisposed to such disease or disorder.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The pharmaceutical compositions of the present invention comprise a compound represented by Formula I (and/or pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

The present invention is further directed to a method for the manufacture of a medicament for the antagonism of NMDA/NR2B receptor activity in humans and animals comprising combining a compound of the present invention with a pharmaceutical carrier or diluent.

In practice, the compounds represented by Formula I, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compound represented by Formula I, and/or pharmaceutically acceptable salt(s) thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.5 mg to about 5 g of the active ingredient and each cachet or capsule preferably containing from about 0.5 mg to about 5 g of the active ingredient.

The pharmaceutical compositions of the present invention comprise a compound represented by Formula I (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, and/or pharmaceutically acceptable salts thereof, may also be prepared in powder or liquid concentrate form.

The utility of the compounds in accordance with the present invention as antagonists of NMDA/NR2B receptor activity may be demonstrated by methodology known in the art. Inhibition of the binding to NMDA receptors and functional antagonism of calcium efflux through NMDA channels were determined as follows:

Cell-Based Functional Assay to Determine $IC_{50}$ of NR2B Antagonists

The ability of selected compounds to inhibit NR1a/NR2B NMDA receptor, as measured by NR1a/NR2B receptor-mediated $Ca^{2+}$ influx, was assessed by the following calcium flux assay procedure:

NR1a/NR2B receptor transfected L(tk−) cells were plated in 96-well format at 3×10⁴ cells per well and grown for one to two days in normal growth medium (Dulbeccos MEM with Na pyruvate, 4500 mg glucose, pen/strep, glutamine, 10% FCS and 0.5 mg/mL geneticin). NR1a/NR2B-expression in these cells was induced by the addition of 4-20 nM dexamethasone in the presence of 500 µM ketamine for 16-24 hours. Solutions of NR2B antagonists were prepared in DMSO and serially diluted with DMSO to yield 10 solutions differing by 3-fold in concentration. A 96-well drug plate was prepared by diluting the DMSO solution 250-fold into assay buffer (Hanks Balanced Salt Solution (HBSS) $Mg^{2+}$ free (Gibco #14175-079) containing 20 mM HEPES, 2 mM $CaCl_2$, 0.1% BSA and 250 µM Probenecid (Sigma # P-8761)). After induction, the cells were washed twice (Labsystem cell washer, 3 fold dilutions leaving 100 µL) with assay buffer and loaded with 4 µM of the calcium fluorescence indicator fluo-3 AM (Molecular Probes # P-1241) in assay buffer containing Pluronic F-127 (Molecular Probes # P-3000) and 10 µM ketamine at 37° C. for one hour. The cells were then washed eight times with assay buffer leaving 100 µL of buffer in each well. Fluorescence intensity was immediately measured in a FLIPR (Fluorometric Imaging Plate Reader, Molecular Devices) using an excitation of 488 nm and emission at 530 nm. Five seconds after starting the recording of fluorescence intensity, 50 µL of agonist solution (40 µM glutamate/glycine, the final concentration 10 µM) was added and after one minute, when fluorescence signal was stable, 50 µL of NR2B antagonists and control solutions from the drug plate were added and the fluorescence intensity recorded for another 30 minutes. The $IC_{50}$ values were determined by a non-linear least squares fitting of the endpoint fluorescence values to Equation #1 below.

Equation #1:

$$\text{Endpoint Florescence} = \frac{(Y\max - Y\min)}{1 + ([\text{Drug}]/IC_{50})^{nH}} + Y\min$$

where, Ymin is average endpoint fluorescence of the control wells containing 1 µM of AMD-2 and Ymax is the average endpoint fluorescence of wells containing 0.1% DMSO in assay buffer.

Binding Assay to Determine $K_I$ NR2B Antagonists

The radioligand binding assay was performed at room temperature in 96-well microtiter plates with a final assay volume of 1.0 mL in 20 mM Hepes buffer (pH 7.4) containing 150 mM NaCl. Solutions of NR2B antagonists were prepared in DMSO and serially diluted with DMSO to yield 20 µL of each of 10 solutions differing by 3-fold in concentration. Non-specific binding (NSB) was assessed using AMD-1 (10 µM final concentration), and total binding (TB) was measured by addition of DMSO (2% final concentration). Membranes expressing NR1a/NR2B receptors (40 pM final concentration) and tritiated AMD-2 (1 nM final concentration) were added to all wells of the microtiter plate. After 3 hours of incubation at room temperature, samples are filtered through Packard GF/B filters (presoaked in 0.05% PEI, polyethylenine Sigma P-3143) and washed 10 times with 1 mL of cold 20 mM Hepes buffer per wash. After vacuum drying of the filter plates, 40 µL of Packard Microscint-20 was added and bound radioactivity determined in a Packard TopCount. The apparent dissociation constant ($K_I$), the maximum percentage inhibition (% $I_{max}$), the minimum percentage inhibition (% $I_{min}$) and the hill slope (nH) were determined by a non-linear least squares fitting the bound radioactivity (CPM bound) to Equation #2 below.

Equation #2:

$$CPM \ \text{Bound} = \frac{(SB)(\% I_{\max} - \% I_{\min})/100}{(1 + ([\text{Drug}]/(K_I(1 + [AMD-2]/K_D)))^{nH})} + NSB + (SB)(100 - \% I_{\max})/100$$

where, $K_D$ is the apparent dissociation constant for the radioligand for the receptor as determined by a hot saturation experiment and SB is the specifically bound radioactivity determined from the difference of TB and NSB control wells.

Synthesis of AMD-1 and AMD-2 may be accomplished according to the following reaction schemes:

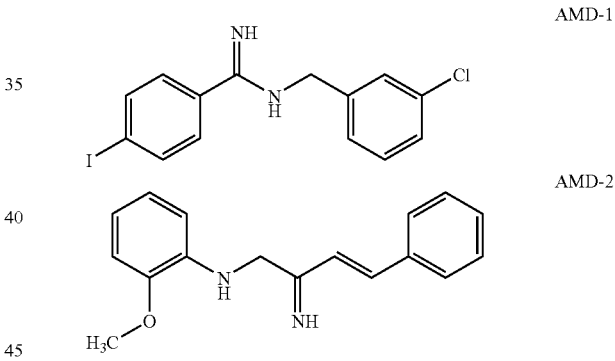

The precursor 26 for the synthesis of radiolabelled AMD-1 can be synthesized in accordance with the following procedure:

Reaction A

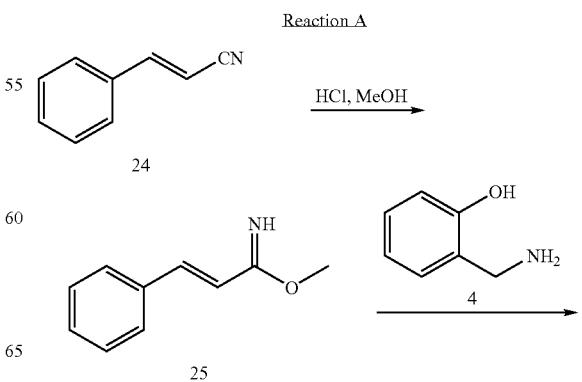

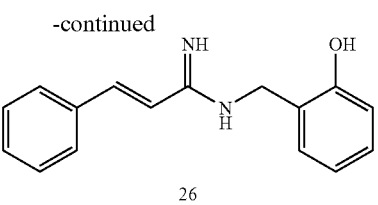

26

In accordance with the procedures of Reaction A, hydrogen chloride is bubbled through a solution of cinnamonitrile 24 in methanol at room temperature. The volatiles are removed under reduced pressure and the resulting residue is triturated with ether and filtered to yield the intermediate imidate 25. Inidate 25 is dissolved in methanol at ambient temperature, treated with amine 27 (commercially available from Acros Chemicals) at ambient temperature and stirred under argon. The volatiles are removed under reduced pressure and the residue purified by preparative HPLC or trituration with ether to afford amidine 26.

Titrated AMD-2 can be synthesized according to the following procedure:

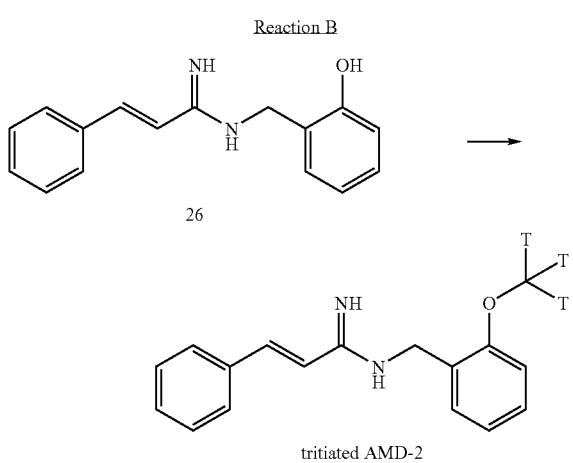

tritiated AMD-2

Tritiated AMD-2 was prepared by the following procedure, illustrated above in Reaction B: The precursor 26 (2 mg, 0.008 mmol) dissolved in dimethylformamide (0.6 mL) and potassium carbonate (1.2 mg) for 1 h. High specific activity tritiated methyl iodide (50 mCi, 0.0006 mmol, in toluene 1 mL, commercially available from American Radiolabeled Chemicals) was added at room temperature and stirred for 2 hours. The reaction mixture was filtered using a Whatman PTFE 0.45 μm syringeless filter device to remove any insoluble potassium carbonate, washed with Abs. ethanol (2 mL, commercially available from Pharmco), and the combined filtrates were concentrated to dryness at room temperature using a rotary evaporator; this also removed any unreacted tritiated methyl iodide. The residue was purified by HPLC chromatography on a Phenomenx Luna C8 semi-prep column (Luna 5 micro C8(2), 250×10.0 mm) using a gradient system of 20/80 acetonitrile/water with 0.1% trifluoroacetic acid to 100% acetonitrile with 0.1% trifluoroacetic acid in 20 min. Total activity of the product was 8 mCi. Further purification was effected by absorption onto a Waters C-18 Sep-pak column (Waters Sep-Pak PLUS C18) and elution with water followed by absolute ethanol. The product was diluted with absolute ethanol (10 mL) before submission for final analysis.

AMD-1 can be synthesized according to the general procedure described by C. F. Claiborne et al (Bioorganic & Medchem Letters 13, 697-700 (2003).

Unlabelled AMD-2 is prepared as follows:

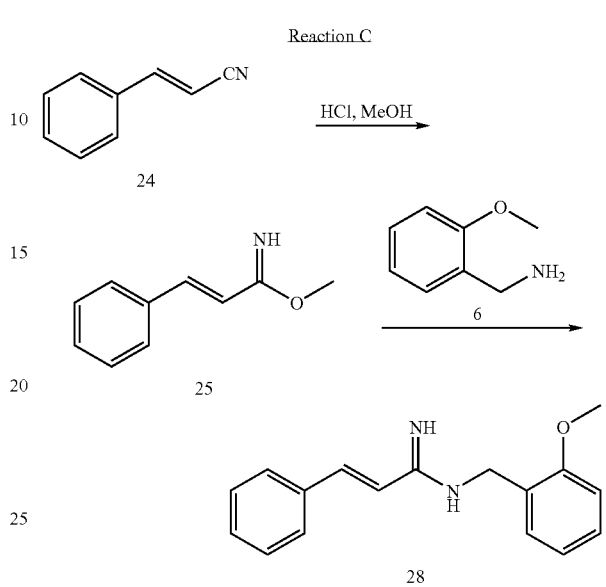

In accordance with Scheme 1b, hydrogen chloride is bubbled through a solution of cinnamonitrile 24 in methanol at room temperature. The volatiles are removed under reduced pressure and the resulting residue is triturated with ether and filtered to yield the intermediate imidate 25. Imidate 25 is dissolved in methanol at ambient temperature, treated with amine 29 at ambient temperature and stirred under argon. The volatiles are removed under reduced pressure and the residue purified by preparative HPLC or trituration with ether to afford amidine 28.

The compounds of this invention exhibit $IC_{50}$ and $K_I$ values of less than 50 μM in the functional and binding assays, respectively. It is advantageous that the $IC_{50}$ and $K_I$ values be less than 5 μM in the functional and binding assays, respectively. It is more advantageous that the $IC_{50}$ and $K_I$ values be less than 1 μM in the functional and binding assays, respectively. It is still more advantageous that the $IC_{50}$ and $K_I$ values be less than 0.1 μM in the functional and binding assays, respectively.

The present compounds are NMDA NR2B receptor antagonists, and as such are useful for the treatment and prophylaxis of diseases and disorders mediated through the NR2B receptor. Such diseases and disorders include, but are not limited to, Parkinson's disease, neuropathic pain (such as postherpetic neuralgia, nerve injury, the "dynias", e.g., vulvodynia, phantom limb pain, root avulsions, painful diabetic neuropathy, painful traumatic mononeuropathy, painful polyneuropathy), central pain syndromes (potentially caused by virtually any lesion at any level of the nervous system), and postsurgical pain syndromes (eg, postmastectomy syndrome, postthoracotomy syndrome, stump pain)), bone and joint pain (osteoarthritis), repetitive motion pain, dental pain, cancer pain, myofascial pain (muscular injury, fibromyalgia), perioperative pain (general surgery, gynecological), chronic pain, dysmennorhea, as well as pain associated with angina, and inflammatory pain of varied origins (e.g. osteoarthritis, rheumatoid arthritis, rheumatic disease, teno-synovitis and gout), headache, migraine and cluster headache, depression, anxiety, schizophrenia, stroke, traumatic brain injury, Alzheimer's disease, cerebral ischemia, amyotrophic lateral sclerosis, Huntington's disease, sensorineural hearing loss, tinnitus, glaucoma, neurological damage caused by epileptic seizures or by neurotoxin poisoning or by impairment of glucose and/or oxygen to the brain, vision loss caused by neurodegeneration of the visual pathway, Restless Leg Syndrome, multi-system atrophy, non-vascular headache, primary hyperalgesia, secondary hyperalgesia, primary allodynia, secondary allodynia, or other pain caused by central sensitization. Compounds of formula I may be used to prevent dyskinesias, particularly the side effects accompanying normal doses of L-Dopa. Furthermore, compounds of formula I may be used to decrease tolerance and/or dependence to opioid treatment of pain, and for treatment of withdrawal syndrome of e.g., alcohol, opioids, and cocaine.

The compounds of this invention are also useful for treating or preventing HIV- and HIV treatment-induced neuropathy, chronic pelvic pain, neuroma pain, complex regional pain syndrome, chronic arthritic pain and related neuralgias, treating or preventing chronic lower back pain, and treating or preventing pain resulting from, or associated with, traumatic nerve injury, nerve compression or entrapment, postherpetic neuralgia, trigeminal neuralgia, diabetic neuropathy, cancer and chemotherapy.

It is understood that compounds of this invention can be administered at prophylactically effective dosage levels to prevent the above-recited conditions, as well as to prevent other conditions mediated through the NMDA NR2B receptor.

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I, either administered separately or in the same pharmaceutical compositions, include, but are not limited to: (1) non-steroidal anti-inflammatory agents; (2) COX-2 inhibitors; (3) bradykinin B1 receptor antagonists; (4) sodium channel blockers and antagonists; (5) nitric oxide synthase (NOS) inhibitors; (6) glycine site antagonists; (7) potassium channel openers; (8) AMPA/kainate receptor antagonists; (9) calcium channel antagonists; (10) GABA-A receptor modulators (e.g., a GABA-A receptor agonist); (11) matrix metalloprotease (MMP) inhibitors; (12) thrombolytic agents; (13) opioids such as morphine; (14) neutrophil inhibitory factor (NIF); (15) L-Dopa; (16) carbidopa; (17) levodopa/carbidopa; (18) dopamine agonists such as bromocriptine, pergolide, pramipexole, ropinirole; (19) anticholinergics; (20) amantadine; (21) carbidopa; (22) catechol 0-methyltransferase ("COMT") inhibitors such as entacapone and tolcapone; (23) Monoamine oxidase B ("MAO-B") inhibitors; (24) opiate agonists or antagonists; (25) 5HT receptor agonists or antagonists; (26) NMDA receptor agonists or antagonists; (27) NK1 antagonists; (28) selective serotonin reuptake inhibitors ("SSRI") and/or selective serotonin and norepinephrine reuptake inhibitors ("SSNRI"); (29) tricyclic antidepressant drugs, (30) norepinephrine modulators; (31) lithium; (32) valproate; and (33) neurontin (gabapentin).

Creams, ointments, jellies, solutions, or suspensions containing the instant compounds can be employed for topical use. Mouth washes and gargles are included within the scope of topical use for the purposes of this invention.

A formulation intended for the oral administration to humans may conveniently contain from about 0.5 mg to about 5 g of active agent, compounded with an appropriate and convenient amount of carrier material which may vary from about 5 to about 95 percent of the total composition. Unit dosage forms can generally contain between from about 1 mg to about 1000 mg of the active ingredient.

The conditions recited herein can be treated or prevented by the administration of from about 0.01 mg to about 140 mg of the instant compounds per kilogram of body weight per day.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy. For example, inflammatory pain may be effectively treated by the administration of from about 0.01 mg to about 75 mg of the present compound per kilogram of body weight per day, or alternatively about 0.5 mg to about 3.5 g per patient per day. Neuropathic pain may be effectively treated by the administration of from about 0.01 mg to about 125 mg of the present compound per kilogram of body weight per day, or alternatively about 0.5 mg to about 5.5 g per patient per day.

The abbreviations used herein are as follows unless specified otherwise:

| | |
|---|---|
| 4-MeBnOH | 4-Methylbenzyl alcohol |
| CDI | 1,1'-Carbonyldiimidazole |
| TEA | Triethylamine |
| TBSCl | t-Butyldimethylsilyl chloride |
| DMF | Dimethylformamide |
| (+)-BINAP | (+)-2,2'-Bis(diphenylphosphino)-1,1'-binaphthyl |
| NaOtBu | Sodium t-butoxide |
| DIPEA | Diisopropylethylamine |
| EtOAc | Ethyl acetate |
| TBSOTf | t-Butyldimethylsilyl triflate |
| TBS | t-butyldimethylsilyl |
| THF | Tetrahydrofuran |
| DMAP | 4-Dimethylaminopyridine |
| RT | Room temperature |
| h | Hours |
| min | Minutes |
| DCM | Dichloromethane |
| MeCN | Acetonitrile |
| iPrOH | 2-Propanol |
| n-BuOH | 1-Butanol |
| EDC | 1-(3-Dimethylaminopropyl)-3-ethylcarbodiimide hydrochloride |
| HOAt | 1-Hydroxy-7-azabenzotriazole |

The compounds of the present invention can be prepared readily according to the following Schemes and specific examples, or modifications thereof, using readily available starting materials, reagents and conventional synthesis procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

Scheme 1

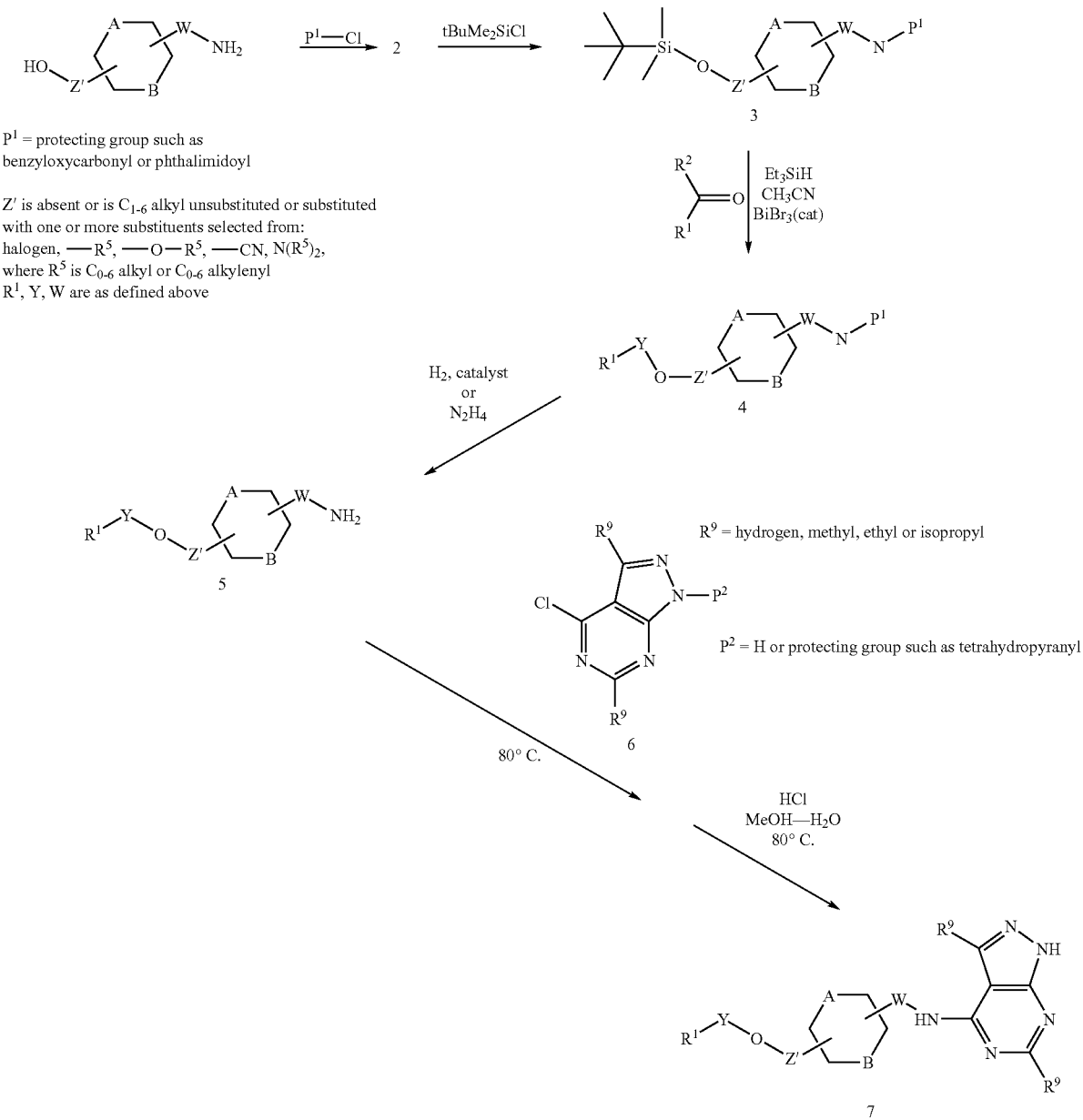

The synthesis of certain aryl-alkoxy substituted cycloalkanes is depicted in Scheme 1. In the first step, a hydroxycycloalkyl-amine 1 is protected with a suitable nitrogen protecting group stable to acidic conditions, such as benzyloxycarbonyl or phthalimidyl. The protected hydroxycycloalkyl-amine 2 is converted into a trialkylsilyl ether such as tert-butyldimethylsilyloxy, triethylsilyloxy-, triisopropylsilyloxy or trimethylsilyloxy-ether 3 using the standard literature procedures such as the one described in the literature (E. J. Corey and A. Venkateswarlu, J. Am. Chem. Soc. 1972, 94, 6190-91. The trialkylsilyloxy-ether 3 is then reductively alkylated with an aldehyde or ketone in the presence of a trialkylsilane such as triethylsilane or tert-butyldimethylsilane and a suitable aprotic acid catalyst such as trimethylsilyl triflate (S. Hatakeyama, H. Mori, K. Kitano, H. Yamada, and M. Nishizawa, Tetrahedron Lett., 1994, 35, 4367-70.), trimethylsilyl bromide or iodide (M. B. Sassaman, K. D. Kotian, G. K. Surya Prakash, and G. A. Olah, J. Org. Chem., 1987, 52, 4314-19) yielding an arylalkyl ether 4. A convenient procedure for generating the trialkylsilyl bromide catalyst in situ, is through the addition of catalytic amounts of bismuth tribromide in acetonitrile solvent (N. Komatsu, J. Ishida, H. Suzuki, Tetrahedron Lett., 1997, 38, 7219-22; J. S. Bojwa, X. Jiang, J. Slade, K. Prasad, O. Repic, T. J. Blacklock, Tetrahedron Lett. 2002, 43, 6709-13). The nitrogen protecting group is removed in the next step using standard methods such as hydrogenolysis, hydrazinolysis or acid hydrolysis, generating the amine-ether 5. The amine is alkylated with 4-chloro- 1H-pyrazolo[3,4-d]pyrimidine 6 (R. K. Robins, J. Amer. Chem. Soc., 78, 784-790 (1956)) using standard alkylation conditions providing the 4-amino-1H-pyrazolo[3,4-d]pyrimidines 7. As an alternative, a suitably N-alkoxymethyl protected derivative of 6 such as N-tetrahydropyranyl, N-tetrahydrofuranyl, or N-ethoxyethylidene provides cleaner products and avoids polymeric products arising from further alkylation of the 1H-pyrazolo[3,4-d]pyrimidine N-1 nitrogen. This type of protecting group is easily removed by brief treatment with aqueous acid in the last step.

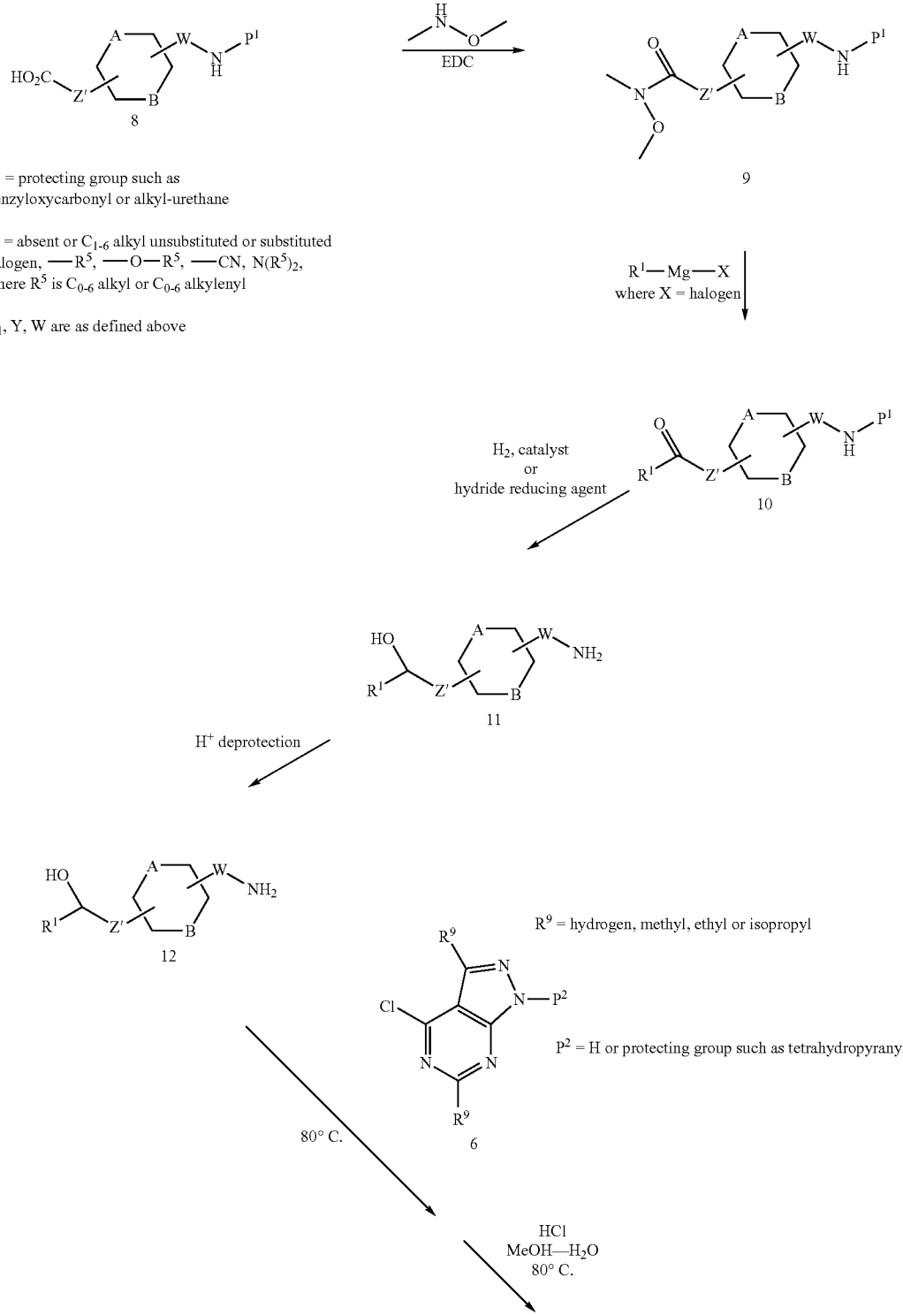

Scheme 2

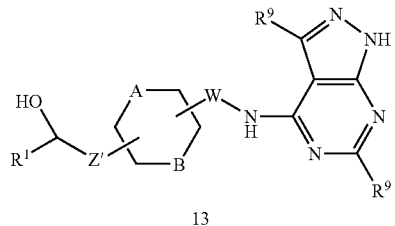

13

The synthesis of certain aryl-hydoxy-alkyl substituted cycloalkanes is depicted in Scheme 2. In the first step, a carboxy-cycloalkyl-amine is protected with a suitable nitrogen protecting group stable to organomagnesium or organolithium reagents, such as benzyloxycarbonyl or tert-butyloxycarbonyl urethanes. The protected carboxy-cycloalkyl-amine 8 is converted into an N-methoxy-N-methyl amide 9 using the standard literature procedures. The N-methoxy-N-methyl amide is converted into an arylalkyl ketone 10 using an organometallic reagent as described in the literature (S. Nahm and S. M. Weinreb, Tetrahedron Lett., 1981, 22, 3815-3818). The ketone 10 is reduced to alcohol 11 with a hydride reagent such as sodium borohydride or hydrogenated with a catalyst An alternative procedure is to convert either the N-methoxy-N-methyl amide 9 or the carboxylic acid 8 into an aldehyde derivative 14 which undergoes addition of the organometallic reagent to form the alcohol 11. The nitrogen protecting group is removed in the next step using standard methods such as hydrogenolysis, hydrazinolysis or acid hydrolysis, generating the amine-alcohol 12. The amine 12 is alkylated with 4-chloro-1H-pyrazolo[3,4-d]pyrimidine 6 (R. K. Robins, J. Amer. Chem. Soc., 78, 784-790 (1956)) using standard alkylation conditions providing the 4-amino-1H-pyrazolo[3,4-d]pyrimidines 7. As an alternative, a suitably N-alkoxymethyl protected derivative of 6 such as N-tetrahydropyranyl, N-tetrahydrofuranyl, or N-ethoxyethylidene provides cleaner products and avoids polymeric products arising from further alkylation of the 1H-pyrazolo[3,4-d]pyrimidine N-1 nitrogen. This type of protecting group is easily removed by brief treatment with aqueous acid in the last step.

Scheme 3

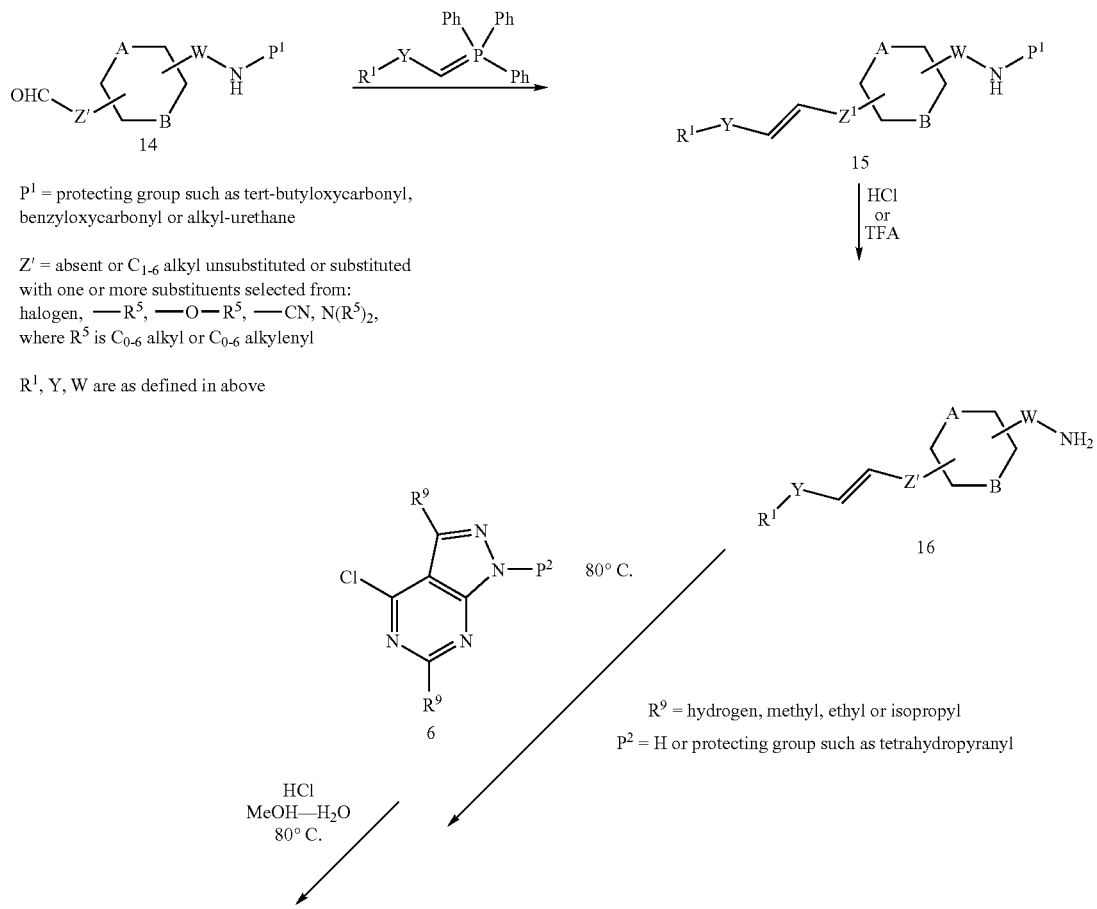

$P^1$ = protecting group such as tert-butyloxycarbonyl, benzyloxycarbonyl or alkyl-urethane $Z'$ = absent or $C_{1-6}$ alkyl unsubstituted or substituted with one or more substituents selected from: halogen, —$R^5$, —O—$R^5$, —CN, N($R^5$)$_2$, where $R^5$ is $C_{0-6}$ alkyl or $C_{0-6}$ alkylenyl $R^1$, Y, W are as defined in above $R^9$ = hydrogen, methyl, ethyl or isopropyl $P^2$ = H or protecting group such as tetrahydropyranyl -continued

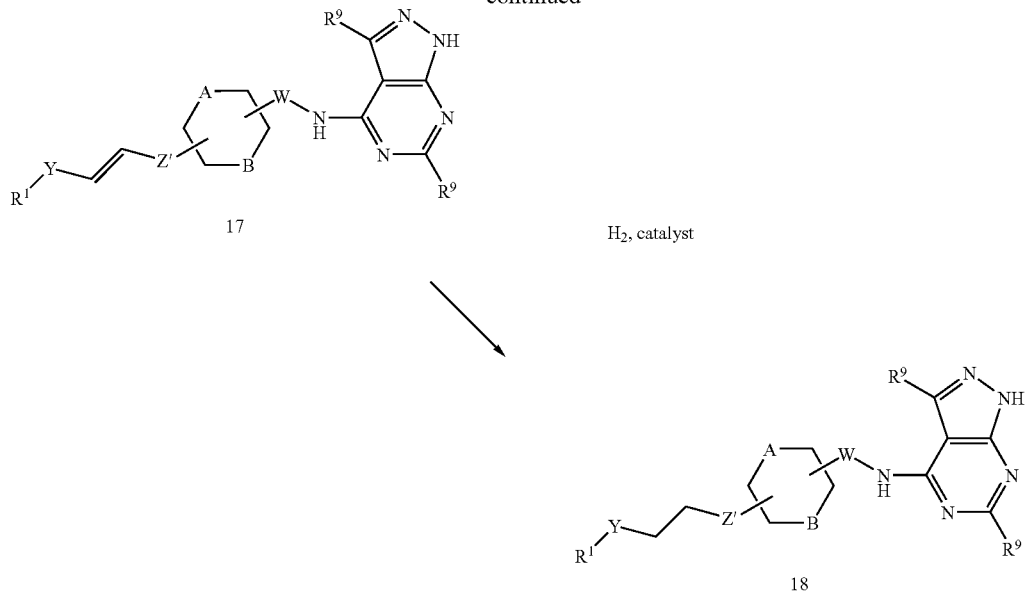

17

H₂, catalyst

18

The synthesis of certain aryl-alkyl substituted cycloalkanes is depicted in Scheme 3. In the first step, a aldehyde-cycloalkyl-amine 14, protected with a suitable nitrogen protecting group stable to organomagnesium or organolithium reagents, such as benzyloxycarbonyl or tert-butyloxycarbonyl urethanes, is reacted with a phosphorane reagent (Wittig reagent) using the standard literature procedures. The resulting olefin-urethane 10 is deprotected using standard methods such as, acid hydrolysis, generating the amine-olefin 16. The amine 16 is alkylated with 4-chloro-1H-pyrazolo[3,4-d]pyrimidine 6 (R. K. Robins, J. Amer. Chem. Soc., 78, 784-790 (1956)) using standard alkylation conditions providing the 4-amino-1H-pyrazolo[3,4-d]pyrimidines 17. As an alternative, a suitably N-alkoxymethyl protected derivative of 6 such as N-tetrahydropyranyl, N-tetrahydrofuranyl, or N-ethoxyethylidene provides cleaner products and avoids polymeric products arising from further alkylation of the 1H-pyrazolo[3,4-d]pyrimidine N-1 nitrogen. This type of protecting group is easily removed by brief treatment with aqueous acid in the last step. The olefin 17 is reduced to alkylcycloalkyl-4-amino-1H-pyrazolo[3,4-d]pyrimidine 18 hydrogenation over a catalyst.

Scheme 4

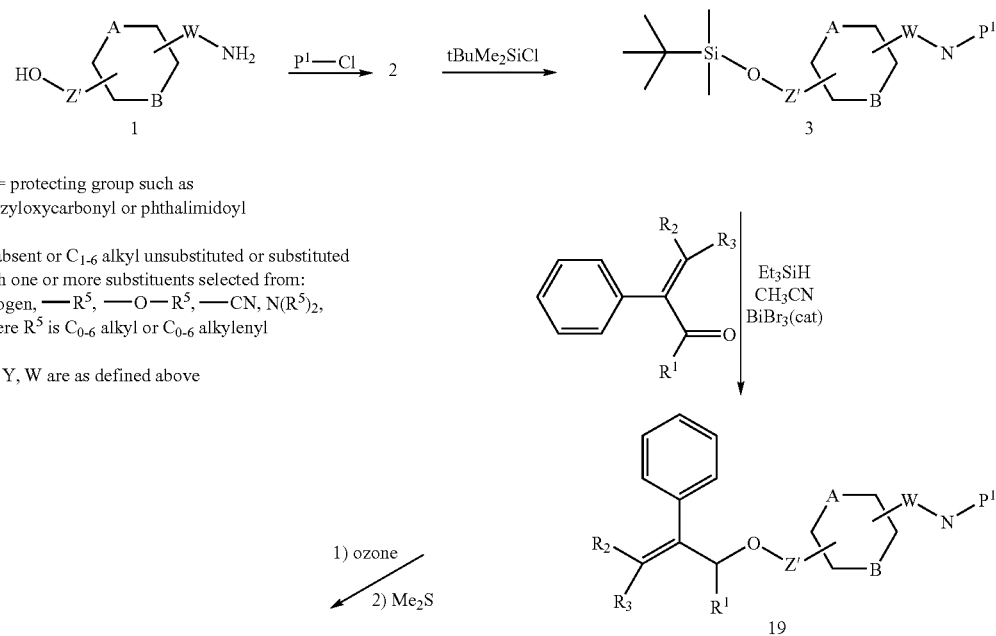

$P^1$ = protecting group such as benzyloxycarbonyl or phthalimidoyl $Z'$ absent or $C_{1-6}$ alkyl unsubstituted or substituted with one or more substituents selected from: halogen, —$R^5$, —O—$R^5$, —CN, N($R^5$)₂, where $R^5$ is $C_{0-6}$ alkyl or $C_{0-6}$ alkylenyl $R^1$, Y, W are as defined above

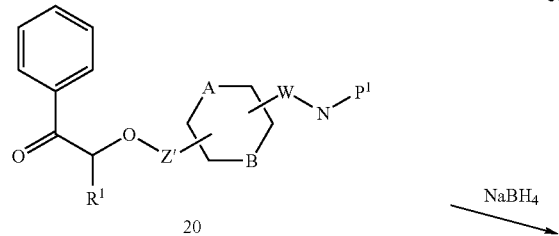

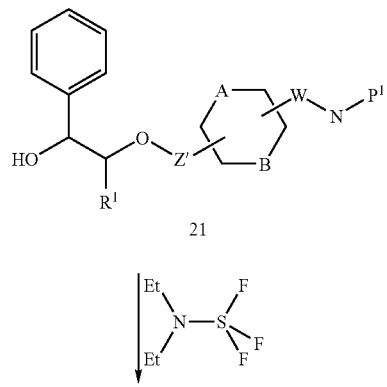

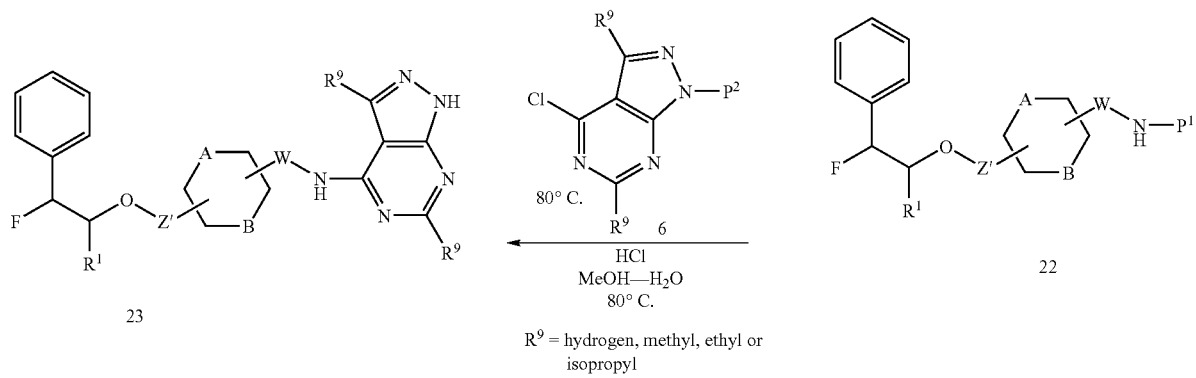

R⁹ = hydrogen, methyl, ethyl or isopropyl

A preferred embodiment is the incorporation of a fluorine substituent into the alkyl-, hydroxy-alkyl or alkoxyl side chain or cyclohexane ring. This can be effected by reaction of a hydroxy intermediate such as 11, 21 or 22 with diethylaminosulfur trifluoride [DAST] similar reagent as illustrated in Scheme 4. The incorporation of geminal a difluoro substitutent can be effected through the use of diethyl sulfur trifluoride on a ketone intermediate such as 20. The ketone and hydroxy intermediates 20 and 21 can be obtained as shown in Scheme 4 by the ether synthesis described for Scheme 1 substituting an unsaturated aldehyde or ketone in the alkylation step. Cleavage of the olefin intermediate 19 yields the ketone 20 which can be further reduced to give hydroxy intermediate 21 with a hydride reducing agent such as sodium borohydride. Reaction of the hydroxy intermediate 21 with diethyl sulfur trifluoride generates the fluoro compound 22. Conversion of 21 into the 4-amino-1H-pyrazolo[3,4-d]pyrimidine 23 uses the methodology as described in Schemes 1-3 above. The use of a chiral reducing agent further provides a a majority of the desired enantiomer of 21. This enantiomerically enhanced form of 21 yields a majority of the desired enantiomer of the chiral fluoro compound 23.

Scheme 5
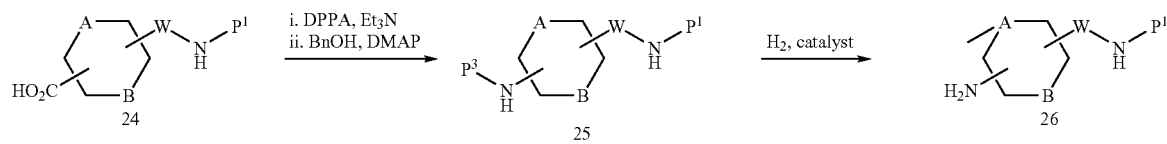
P[1] = protecting group such as BOC
P[3] = protecting group such as Cbz
R[1] and W are as defined above
R[3'] is C0-5 alkyl, unsubstituted or substituted with one or more halogen
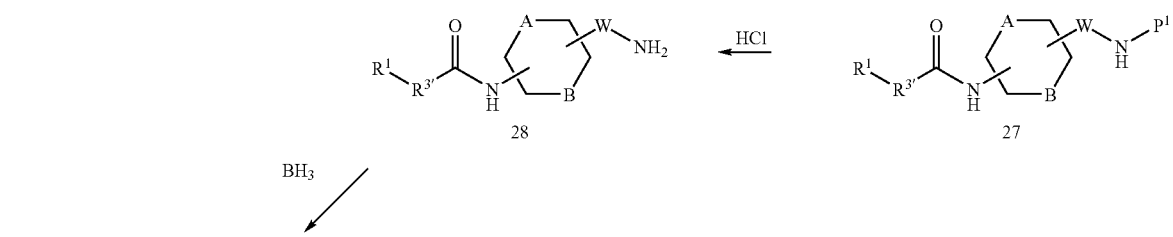
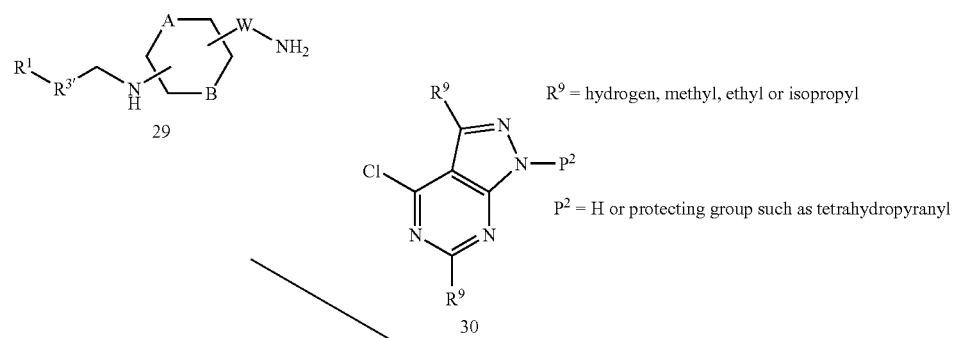
R[9] = hydrogen, methyl, ethyl or isopropyl
P[2] = H or protecting group such as tetrahydropyranyl
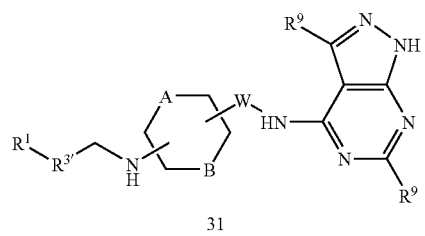

The synthesis of certain amino substituted cycloalkanes is depicted in Scheme 5. First an N-protected aminocycloalkane carboxylic acid 24 is subjected to a Curtius reaction to give amine 26 via the intermediate heteroprotected diaminocycloalkane 25. Amine 26 is acylated with a suitable carboxylic acid derivative to give amide 27 and the protecting group is then removed, in this case with acid, to give amide 28. The amide is then reduced with a reagent such as borane to give diamine 29. The diamine is then reacted with protected 4-chloro-1H-pyrazolo[3,4d]pyrimidine 30 and the protecting group removed to give 31.

EXAMPLE 1 trans-(4-Phenethyloxy-cyclohexyl)-(1H-pyrazolo[3,4-d]pyrimidin-4-yl)-amine

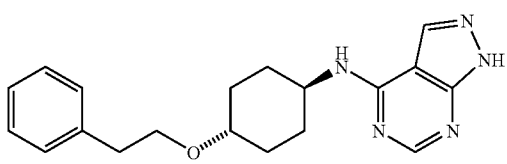

Step 1:
trans-2-(4-Hydroxy-cyclohexyl)-isoindole-1,3-dione

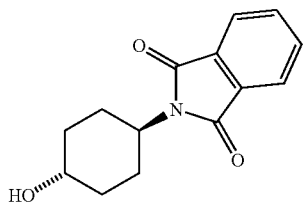

A mixture of 31 grams of trans-4-aminocyclohexanol, 550 mL of anhydrous THF, 45 mL of triethylamine and 53 g of N-carboethoxy-phthalimide was heated to reflux for 18 h, cooled, and diluted with 1500 mL of ethyl acetate. The solution was washed with 250 mL of 10% HCl, 100 mL of saturated sodium bicarbonate then dried over magnesium sulfate. Concentration under reduced pressure gave 66 g of product as a white crystalline solid contaminated with ethyl carbamate. This material was sufficiently pure for the next step, although it could be recrystallized from boiling ethyl acetate-hexane. 1H NMR (400 MHz, CDCl3) 7.8 (m, 2H), 7.7 (m, 2H), 4.15 (m, 1H), 3.7 (m, 1H), 2.3 (dd, 2H), 2.1 (d, 2H), 1.78 (d, 2H), 1.4 (dd, 2H).

Step 2: trans-2-(4-(tert-Butyl-dimethyl-silyloxy-cyclohexyl)-isoindole-1,3-dione

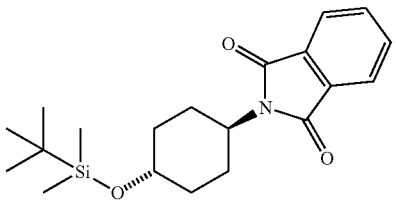

A mixture of 13 g of 2-(4-hydroxy-cyclohexyl)-isoindole-1,3-dione (Compound 1), 10 g of tert-butyldimethylsilyl chloride, 9.3 g of imidazole and 40 mL of DMF was stirred for 24 h. The mixture was diluted with 500 mL of ether and washed with 3×500 mL portions of water, dried over magnesium sulfate and concentrated under reduced pressure. The product crystallized under vacuum as a white solid: 18.5 g. 1H NMR (400 MHz, CDCl3) 1H NMR (400 MHz, CDCl3) 7.8 (m, 2H), 7.7 (m, 2H), 4.15 (m, 1H), 3.7 (m, 1H), 2.3 (dd, 2H), 2.1 (d, 2H), 1.78 (d, 2H), 1.4 (dd, 2H), 0.9 (s, 9H), 0.5 (s, 6H).

Step 3: trans-2-(4-Phenylethyloxy-cyclohexyl)-isoindole-1,3-dione

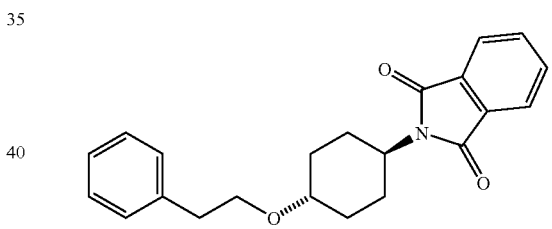

To a solution of 10 g of ethyl phenylacetate in 100 mL of dry toluene cooled to −78° C. under nitrogen was added drop-wise 68 mL of 0.9 M di-isobutyl-aluminum hydride in toluene, keeping the internal temperature below −68° C. When the addition was complete, the reaction was quenched with 200 mL of 10% HCl, and extracted into 2×100 mL portions of ether. The combined ether layers were washed with 2×100 mL portions of 10% HCl, 100 mL of saturated sodium bicarbonate, diluted with 100 mL of toluene, and dried over magnesium sulfate. Concentration under reduced pressure gave 7.1 g of phenyl acetaldehyde as a volatile liquid. 1H NMR (400 MHz, CDCl3) 9.8 (s, 1H), 7.5-7.2 (m, 5H), 3.7 (s 2H). To a stirred mixture of 10 g of trans-2-(4-(tert-butyl-dimethyl-silyloxy-cyclohexyl)-isoindole-1,3-dione (Compound 2), 150 mL of anhydrous acetonitrile, 7 mL of triethylsilane and 0.7 g of bismuth tribromide was added 5 g of the freshly prepared phenyl acetaldehyde slowly keeping the temperature at or below 25° C. by means of a cooling bath. After stirring for 2 h, the reaction was quenched with 50 mL of saturated sodium bicarbonate and extracted with 3×150 mL portions of ethyl acetate. The combined extracts were dried over magnesium sulfate and concentrated under reduced pressure. Chromatography over silica gel eluting with a gradient of 2%-25% ethyl acetate in hexane gave 9.0 g of product as a white crystalline solid: 1H NMR (400 MHz, CDCl3) 7.8 (m, 2H), 7.7 (m, 2H), 7.3-7.1 (m, 5H), 4.15 (m, 1H), 3.7 (t, 2H), 3.38 (m, 1H), 2.9 (t, 2H), 2.22 (d, 2H), 2.3 (dd, 2H), 2.18 (d, 2H), 1.78 (d, 2H), 1.4 (dd, 2H).

Step 4: trans 4-Phenylethyloxy-cyclohexylamine

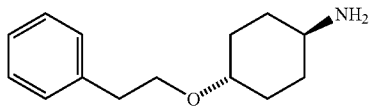

To a solution of 9 g of trans-2-(4-phenylethyloxy-cyclohexyl)-isoindole-1,3-dione in 60 mL of THF and 150 mL of ethanol was added 3.75 mL of hydrazine hydrate and the mixture heated to reflux for 4 h, then 80 mL of 6N HCl was added and the reflux was continued for 1 h. The cooled mixture was concentrated under reduced pressure to remove ethanol and filtered. The filter pad was washed with 2×50 mL of dilute HCl and the combined filtrates basified to pH 10 with 20% sodium hydroxide and extracted with 3×150 mL portions of chloroform. The combined extracts were dried over magnesium sulfate and concentrated under reduced pressure. Further drying under vacuum gave 6 g of product as an oil. MS (m+1)=220.2; 1H NMR (400 MHz, CDCl3) 7.3-7.1 (m, 5H), 3.7 (t 2H), 3.2 (m, 1H), 2.9 (t, 2H), 2.7 (m, 1H), 2.0 (d, 2H), 1.85 (d, 2H), 1.4 (br s, 2H), 1.3 (dd, 2H), 1.15 (dd, 2H).

Step 5: trans-(4-Phenethyloxy-cyclohexyl)-(1H-pyrazolo[3,4-d]pyrimidin-4-yl)-amine

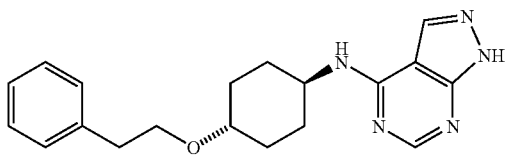

A mixture of 219 mg of trans-4-(2-phenyl-ethoxy)-cyclohexylamine, 154 mg of 4-chloro-1H-pyrazolo[3,4-d]pyrimidine (R. K. Robins, J. Amer. Chem. Soc., 78, 784-790 (1956)), 10 mL of 2-propanol and 0.174 mL of N,N-diisopropyl-ethylamine was heated to 80° C. for 12 hours. The mixture was cooled and concentrated under reduced pressure and purified by either preparative TLC eluting with 50:50:5 THF:diethyl ether:NH4OH or preparative reverse phase chromatography on delta Pak C (C-18 column) eluting with a gradient of 90:10 to 0:100 of 0.1% TFA in H₂O: CH3CN gave 60-92% of (4-phenethyloxy-cyclohexyl)-(1H-pyrazolo[3,4-d]pyrimidin-4-yl)-amine as a white crystalline solid. MS (m+1)=338.32; 1H NMR (400 MHz, CDCl3) 8.43 (s, 1H), 7.92 (s, 1H), 7.3-7.2 (m, 5H), 3.7 (t, 2H), 3.3 (m, 1H), 2.9 (t, 2H), 2.22 (d, 2H), 2.1 (d, 2H), 1.7 (m, 1H), 1.5 (dd, 2H), 1.4 (m, 2H).

EXAMPLE 2 trans-[4-(2-Fluoro-2-phenyl-ethoxy-cyclohexyl)-(1H-pyrazolo[3,4-d]pyrimidin-4-yl)-amine

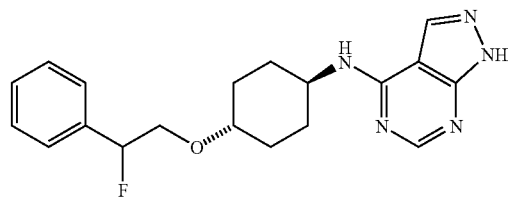

Step 1: trans-2-[4-(5-Methyl-2-phenyl-hex-2-enyloxy)-cyclohexyl]-isoindole-1,3-dione

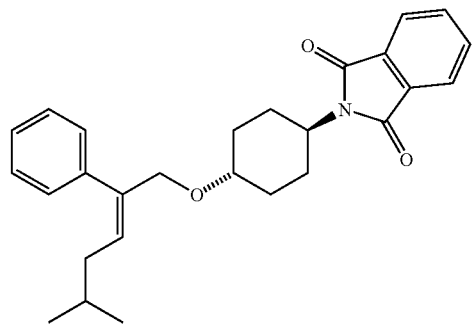

To a stirred mixture of 1 g of trans-2-(4-(tert-butyl-dimethyl-silyloxy-cyclohexyl)-isoindole-1,3-dione, 20 mL of anhydrous acetonitrile, 0.8 mL of triethylsilane and 0.6 g of 5-methyl-2-phenyl-2-hexenal (commercial, predominantly trans was added ) 0.08 g of bismuth tribromide. After stirring for 1.3 h, the reaction was quenched with 10 mL of saturated sodium bicarbonate and extracted with 3×25 mL portions of ethyl acetate. The combined extracts were dried over magnesium sulfate and concentrated under reduced pressure. Chromatography over silica gel eluting with a gradient of 1%-20% ethyl acetate in hexane gave first 0.30 g of saturated product, trans-2-[4-(5-methyl-2-phenyl-hexyloxy)-cyclohexyl]-isoindole-1,3-dione, then 0.50 g of product as a resin: 1H NMR (400 MHz, CDCl3) 7.8 (m, 2H), 7.7 (m, 2H), 7.3-7.1 (m, 5H), 5.8 (t, 1H), 4.25 (s, 2H), 4.15 (m, 2H), 3.4 (m, 1H), 2.3 (m, 2H), 2.1 (d, 2H), 1.9 (t, 2H), 1.75 (d, 2H), 1.65 (, 1H), 1.35 (m, 2H), 1.3 (t, 2H), 0.9 (d, 6H).

Step 2: trans-2-[4-(2-Oxo-2-phenyl-ethoxy)-cyclohexyl]-isoindole-1,3-dione

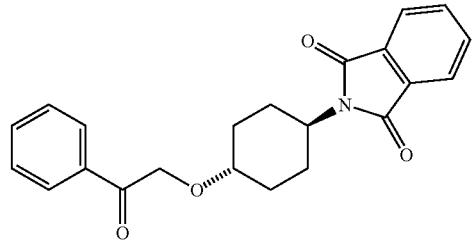

To a stirred solution of 2 g of trans-2-[4-(5-methyl-2-phenyl-hex-2-enyloxy)-cyclohexyl]-isoindole-1,3-dione in 100 mL of dichloromethane cooled to −78° C. was dispersed a stream of ozone from an ozone generator until a blue color persisted. The excess ozone was purged with nitrogen until the blue color dissipated, and 5 mL of methyl sulfide was added. After warming to room temperature over 30 min, the solution was concentrated under reduced pressure. Chromatography over silica gel eluting with a gradient of 2%-30% ethyl acetate in hexane gave 1.8 g of product as a white crystalline solid: 1H NMR (400 MHz, CDCl3) 8.0 (d, 2H), 7.8 (m, 2H), 7.6 (t, 1H), 7.5 (t, 2H), 4.8 (s, 2H), 4.18 (m, 1H), 3.5 (m, 1H), 2.35 and 2.25 (overlapping dd and d, 4H), 1.8 (d, 2H), 1.5 (dd, 2H).

Step 3: trans-2-[4-(2-Hydroxy-2-phenyl-ethoxy)-cyclohexyl]-isoindole-1,3-dione

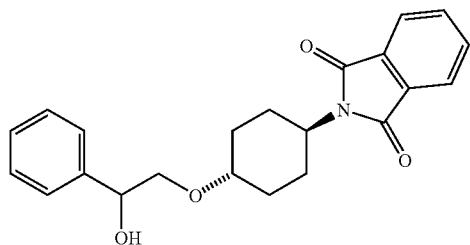

A mixture of 1 g of trans-2-[4-(2-oxo-2-phenyl-ethoxy)-cyclohexyl]-isoindole-1,3-dione and 0.1 g of 10% palladium on carbon in 100 mL of ethanol was stirred under 1 atm. of hydrogen overnight. The catalyst was filtered off and the filtrate concentrated to dryness under reduced pressure. Drying under vacuum gave 1.0 g of product as a white crystalline solid: 1H NMR (400 MHz, CDCl3) 7.8 (m, 2H), 7.65 (t, 1H), 7.4-7.2 (m, 5H), 4.82 (d, 1H), 4.1 (m, 1H), 3.65 (m, 2H), 3.4 (m, 2H), 2.3 (dd, 2H), 2.2 (m, 2H), 1.8 (d, 2H), 1.4 (dd, 2H).

Step 4: trans-2-[4-(2-Fluoro-2-phenyl-ethoxy)-cyclohexyl]-isoindole-1,3-dione

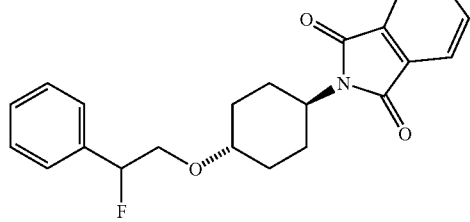

To a stirred solution of 1 g of trans-2-[4-(2-hydroxy-2-phenyl-ethoxy)-cyclohexyl]-isoindole-1,3-dione in 100 mL of dichloromethane cooled to −78° C. under nitrogen atmosphere was added 1.2 g of diethyl-amino sulfur-trifluoride. The mixture was allowed to warm and stir for 24 h, then quenched with 25 mL of saturated sodium carbonate. After stirring for 15 min, the mixture was diluted with 25 mL of dichloromethane and the layers separated. The organic layer was dried over magnesium sulfate and concentrated under reduced pressure. Chromatography over silica gel eluting with a gradient of 2%-30% ethyl acetate in hexane gave 0.7 g of product as a white crystalline solid: 1H NMR (400 MHz, CDCl3) 7.8 (m, 2H), 7.7 (t, 1H), 7.4-7.3 (m, 5H), 5.6 (dd, 1H), 4.1 (m, 1H), 3.9-3.65 (complex m, 2H), 3.45 (m, 1H), 2.3 (dd, 2H), 2.2 (m, 2H), 1.8 (d, 2H), 1.4 (dd, 2H).

Step 5: trans-4-(2-Fluoro-2-phenyl-ethoxy)-cyclohexyl-amine

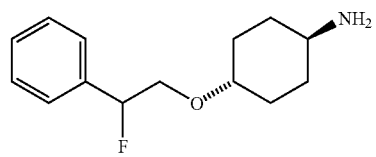

To a solution of 0.7 g of racemic trans-2-[4-(2-fluoro-2-phenyl-ethoxy)-cyclohexyl]-isoindole-1,3-dione in 15 mL of THF and 15 mL of ethanol was added 0.3 mL of hydrazine hydrate and the mixture heated to reflux for 4 h, then 5 mL of 6N HCl was added and the reflux was continued for 1 h. The cooled mixture was concentrated under reduced pressure to remove ethanol and filtered. The filter pad was washed with 2×10 mL of dilute HCl and the combined filtrates basified to pH 10 with 20% sodium hydroxide and extracted with 3×25 mL portions of chloroform. The combined extracts were dried over magnesium sulfate and concentrated under reduced pressure. Further drying under vacuum gave 0.4 g of product as an oil. MS (m+1)=238.3.

Step 6: 4-Chloro-1-(tetrahydro-pyran-2-yl)-1H-pyrazolo[3,4-d]pyrimidine and 4-chloro-2-(tetrahydro-pyran-2-yl)-2H-pyrazolo[3,4-d]pyrimidine

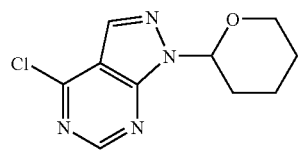

A mixture of 8.5 g of 4-chloro-pyrazolo[3,4-d]pyrimidine, 600 mL of acetonitrile, and 400 mg of camphor-sulfonic acid was stirred overnight. The mixture was washed with 25 mL of saturated sodium carbonate, dried over magnesium sulfate and concentrated to dryness under reduced pressure. Chromatography over silica gel eluting with a gradient of 1%-20% ethyl acetate in hexane gave 12 g of the 1-THP product as a white crystalline solid which was stored under nitrogen in the freezer: 1H NMR (400 MHz, CDCl3) 8.8 (s, 1H), 8.2 (s, 1H), 6.05 (d, 1H). Later fractions eluting with ethyl acetate contained 1.5 g the isomeric 2-THP product: 1H NMR (400 MHz, CDCl3) 8.25 (s, 1H), 8.15 (s, 1H), 5.85 (m, 1H). The ratio of the two isomeric products varied, but either isomer could be used in the alkylation step to generate a 4-alkylamino-pyrazolo[3,4-d]pyrimidine.

Step 7: trans-[4-(2-Fluoro-2-phenyl-ethoxy-cyclohexyl)-(1H-pyrazolo[3,4-d]pyrimidin-4-yl)-amine

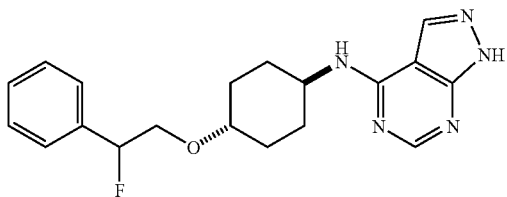

A mixture of 0.4 g of trans-4-(2-fluoro-2-phenyl-ethoxy)-cyclohexyl-amine, 0.5 g of 4-chloro-1-(tetrahydro-pyran-2-yl)-1H-pyrazolo[3,4-d]pyrimidine, and 0.4 mL of N,N-diisopropylethylamine in 25 mL of 2-propanol was heated to reflux under nitrogen overnight. The mixture was cooled and concentrated under reduced pressure. The tan residue was taken up in 200 mL of ethyl acetate, washed with 20 mL of saturated sodium bicarbonate, dried over magnesium sulfate and concentrated under reduced pressure. Chromatography over silica gel eluting with a gradient of 50%-100% ethyl acetate in hexane gave 0.72 g of product as a white solid. The solid was taken up in 75 mL of methanol and 5 mL of 6N HCl and heated at reflux for 15 minutes, cooled and concentrated under reduced pressure to dryness. The solid residue was treated with 10 mL of concentrated aqueous ammonia and again concentrated to dryness. The resulting residue was extracted with 100 mL of chloroform, filtered and concentrated to dryness under reduced pressure. Chromatography over silica gel eluting with a gradient of 1%-5% methanol in ethyl acetate gave 0.45 g of product as a white solid: MS (m+1)=356.3; 1H NMR (400 MHz, CDCl3) 8.4 (s, 1H), 7.9 (s, 1H), 7.4-7.3 (m, 5H), 5.6 (dd, 1H), 3.9-3.65 (complex m, 3H), 3.4 (m, 1H), 2.3 (m, 2H), 2.2 (m, 2H), 1.75-1.4 (m, 4H).

Resolution into the pure enantiomers could be performed by isocratic elution on ChiralPak AD at 1 mL/min, eluting with 20% methanol in 2-propanol.

EXAMPLE 3 trans [4-(2,2-Difluoro-2-phenyl-ethoxy)-cyclohexyl)-carbamic acid tert-butyl ester

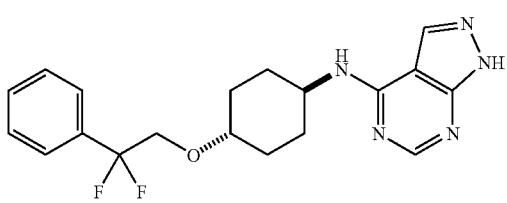

Step 1: trans (4-Hydroxy-cyclohexyl)-carbamic acid tert-butyl ester

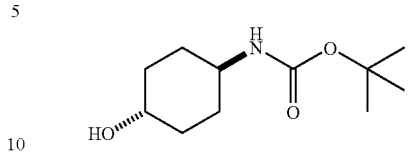

A mixture of 5 g of trans 4-aminocyclohexanol and 9.5 g of di-tert-butyl di-carbonate in 200 mL of THF was heated to reflux for 2 h at which time the mixture became homogeneous. The mixture was cooled and concentrated under reduced pressure. Drying under vacuum gave 9.34 g of product as a white crystalline solid; 1H NMR (400 MHz, CDCl3) 4.4 (br s, 2H), 3.6 (m, 1H), 3.4 (br s, 1H), 2.0 (t, 4H), 1.45 (s, 9H), 1.4 (dd, 2H), 1.2 (dd, 2H).

Step 2: cis (4-Hydroxy-cyclohexyl)-carbamic acid tert-butyl ester

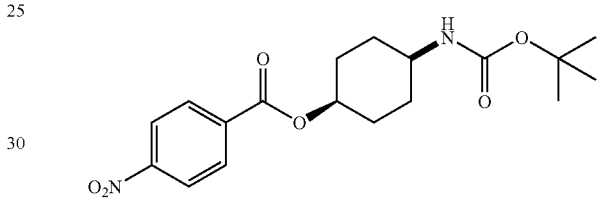

To a stirred mixture of 2.2 g of trans (4-hydroxy-cyclohexyl)-carbamic acid tert-butyl ester, 4 g of triphenyl-phosphine, 4.2 g of 4-nitrobenzoic acid, 120 mL of benzene and 10 mL of THF was added 3.5 g of diisopropyl-azo-di-carboxylate over 5 min. The mixture was allowed to stir at room temperature for 4 h and then concentrated under reduced pressure, taken up in 250 mL of dichloromethane and filtered and again concentrated. Chromatography on silica gel eluting with a gradient of 2%-20% ethyl acetate in hexane gave 1.2 g of product as a crystalline solid; 1H NMR (400 MHz, CDCl3) 8.3 (d, 2H), 8.2 (d, 2H), 3.8 (br m, 1H), 3.6 (br m, 1H), 2.4 (d, 1H), 2.1-1.6 (complex m, 8H), 1.45 (s, 9H).

Step 3: cis (4-Hydroxy-cyclohexyl)-carbamic acid tert-butyl ester

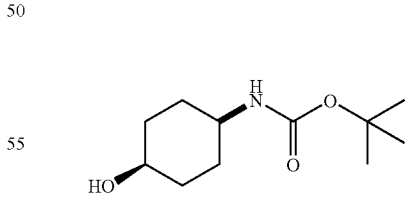

A mixture of 1.2 g of cis (4-hydroxy-cyclohexyl)-carbamic acid tert-butyl ester, 20 mL of 2N sodium hydroxide and 50 mL of THF was heated to reflux for 12 h. The mixture was cooled, diluted with 50 mL of water and extracted with 3×50 mL portions of ether. The combined extracts were dried over magnesium sulfate and concentrated under reduced pressure. Drying under vacuum gave 0.70 g of product as a white crystalline solid; 1H NMR (400 MHz, CDCl3) 4.5 (m, 1H), 3.9 (m, 1H), 3.5 (br s, 1H), 1.6 (m, 8H), 1.42 (s, 9H).

Step 4: 2,2-Difluoro-2-phenyl-ethanol

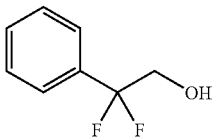

A stirred mixture of 2.2 g of difluoro-2-phenyl acetic acid ethyl ester (W. J. Middleton, E. M. Bingham, J. Org. Chem., 45, 2883-2887 (1980)), and 0.6 g of sodium borohydride in 75 mL of ethanol was kept at room temperature overnight, concentrated to near dryness under reduced pressure carefully acidified with 20 mL of 5% HCl and extracted into 3×50 mL of dichloromethane. The combined extracts were dried over magnesium sulfate and concentrated under reduced pressure. Drying under vacuum gave 1.7 g of product as an oil: 1H NMR (400 MHz, CDCl3) 7.5 (m, 5H), 4.0 (t, 2H).

Step 5: trans [4-(2,2-Difluoro-2-phenyl-ethoxy)-cyclohexyl)-carbamic acid tert-butyl ester

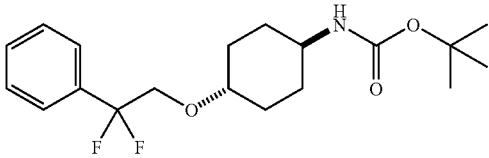

To a stirred mixture of 0.23 g of g of cis-(4-hydroxy-cyclohexyl)-carbamic acid tert-butyl ester, 0.54 g of 1.1'-(azodicarbonyl)-dipiperidine and 20 mL of benzene was added 0.4 g of tri-n-butyl-phosphine and 1.3 g (8 equivalents) of 2,2-difluoro-2-phenyl-ethanol. The mixture was heated to 60° C. overnight, then an additional 0.5 g of 1.1'-(azodicarbonyl)-dipiperidine and 0.4 g of tri-n-butyl-phosphine was added and heating continued for another 24 h. The mixture was cooled, diluted with 25 mL of toluene, filtered and the filter pad washed with 5 mL of toluene. The filtrate was purified by chromatography on silica gel eluting with a gradient of 0%-20% ethyl acetate in hexane gave 0.15 g of product as a resin: 1H NMR (400 MHz, CDCl3) 7.5 (m, 5H), 3.95 (m, 2H), 3.4 (m, 1H), 1.95 (m, 2H), 1.6 (m, 6H), 1.45 (s, 9H).

Step 6: trans [4-(2,2-Difluoro-2-phenyl-ethoxy)-cyclohexyl)-carbamic acid tert-butyl ester

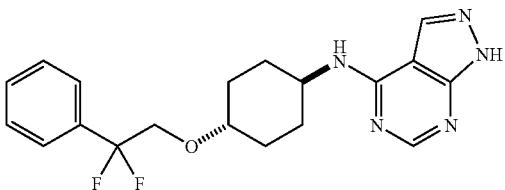

A mixture of 0.15 g of trans [4-(2,2-difluoro-2-phenyl-ethoxy)-cyclohexyl)-carbamic acid tert-butyl ester an 10 mL of 4N HCl in dioxane was stirred at room temperature for 4 h then concentrated to dryness under reduced pressure. The resulting HCl salt was taken up in 10 mL of 2-propanol with 0.05 g of 4-chloro-1H-pyrazolo[3,4-d]pyrimidine (R. K. Robins, J. Amer. Chem. Soc., 78, 784-790 (1956)), and 0.3 mL of N,N-diisopropyl-ethylamine and heated to 80° C. for 12 hours. The mixture was cooled and concentrated under reduced pressure and the crude product purified by either preparative TLC eluting with 50:50:5 THF:diethyl ether: NH4OH gave 20 mg of (4-phenethyloxy-cyclohexyl)-(1H-pyrazolo[3,4-d]pyrimidin-4-yl)-amine as a white crystalline solid. MS (m+1)=374.1; 1H NMR (400 MHz, CDCl3) 8.43 (s, 1H), 7.95 (s, 1H), 7.5-7.4 (m, 5H), 3.7 (t, 2H), 3.4 (m, 1H), 2.2 (d, 2H), 2.1 (d, 2H), 1.7 (m, 1H), 1.5 (dd, 21), 1.4 (m, 2H).

EXAMPLE 4

[4-((1R,2R)-2-Phenyl-cyclopropylmethoxy)-cyclohexyl]-(1H-pyrazolo[3,4-d]pyrimidin-4-yl)-amine

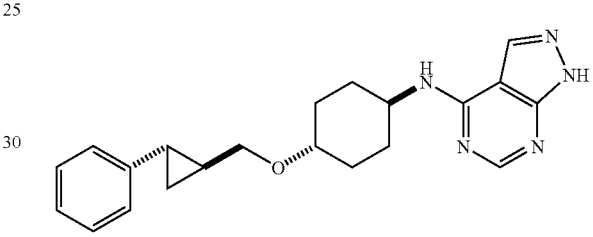

Step 1: (1R, 2R)-2-Phenyl-cyclopropanecarboxylic acid ethyl ester

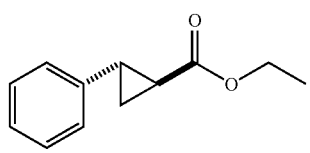

To an ice cold solution of 1.62 g of (1R, 2R)-2-phenyl-cyclopropane carboxylic acid (from racemic trans-2-phenyl-cyclopropane carboxylic acid by resolution on a chiral HPLC column) and 2.0 mL of triethylamine and 0.12 g of 4-dim-ethylaminopyridine was added 1.2 mL of ethyl chloroformate The mixture was allowed to warm and stir for 1 h, then washed with 25 mL of 3N HCl, 25 mL of water, 25 mL of saturated sodium carbonate and dried over magnesium sulfate. Removal of solvents under reduced pressure gave 1.9 g of product as an oil: MS (m+1)=191.1; 1H NMR (400 MHz, CDCl3) 7.3 (dd, 2H), 7.2 (t, 1H), 7.1 (d, 2H), 4.18 (q, 2H), 2.5 (m, 1H), 1.9 (m, 1H), 1.6 (m, 1H), 1.3 (overlapping m and t, 4H).

Step 2: [4-((1R,2R)-2-Phenyl-cyclopropylmethoxy)-cyclohexyl]-(1H-pyrazolo[3,4-d]pyrimidin-4-yl)-amine

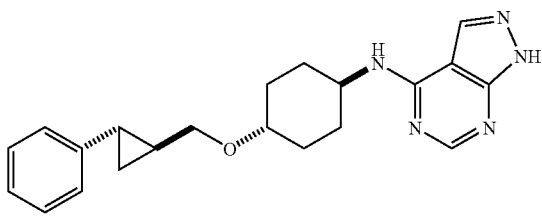

From (1R, 2R)-2-phenyl-cyclopropanecarboxylic acid ethyl ester, using the procedure described for the preparation of Example 1, Step 3 gave [4-((1R,2R)-2-phenyl-cyclopropylmethoxy)-cyclohexyl]-(1H-pyrazolo[3,4-d]pyrimidin-4-yl)-amine as a white solid: MS (m+1)=364.1; 1H NMR (400MHz, CDCl3) 8.45 (s, 1H), 7.92 (s, 1H), 7.3 (dd, 2H), 7.2 (t, 1H), 7.1 (d, 2H), 3.6 (m, 2H), 3.4 (m, 2H), 2.3 (d, 2H), 2.18 (d, 2H), 2.1 (d, 2H), 1.95 (m, 1H), 1.85 (m, 1H), 1.4 (m, 4H), 0.95 (m, 2H).

EXAMPLE 5 trans-{4-[2-(2-Fluoro-phenyl)-ethoxy]-cyclohexyl}-(1H-pyrazolo[3,4-d]pyrimidin-4-yl)-amine

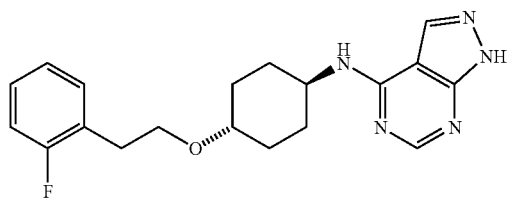

From 2-fluoro-phenylacetic acid ethyl ester, using the procedure described for the preparation of Example 1, Step 3 gave trans-{4-[2-(2-fluoro-phenyl)-ethoxy]-cyclohexyl}-(1H-pyrazolo[3,4-d]pyrimidin-4-yl)-amine as a white solid: MS (m+1)=356.1; 1H NMR (400 MHz, CDCl3) 8.4 (s, 1H), 7.92 (s, 1H), 7.2 (m, 2H), 7.05 (m, 2H), 4.0 (m, 1H), 3.65 (m, 2H), 3.3 (m, 1H), 2.95 (m, 2H), 2.22 (d, 2H), 2.15 (d, 2H), 1.7 (m, 1H), 1.5 (m, 2H), 1.4 (m, 2H).

EXAMPLE 6 trans-{4-[2-(4-Fluoro-phenyl)-ethoxy]-cyclohexyl}-(1H-pyrazolo[3,4-d]pyrimidin-4-yl)-amine

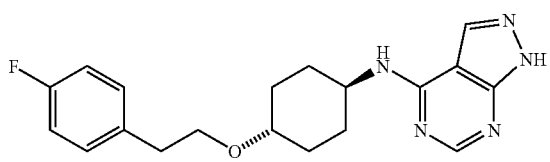

From 4-fluoro-phenylacetic acid methyl ester, using the procedure described for the preparation of Example 1, Step 3 gave trans-{4-[2-(4-fluoro-phenyl)-ethoxy]-cyclohexyl}-(1H-pyrazolo[3,4-d]pyrimidin-4-yl)-amine as a white solid: MS (m+1)=356.1; 1H NMR (400 MHz, CDCl3) 8.4 (s, 1H), 7.92 (s, 1H), 7.2 (m, 2H), 6.95 (m, 2H), 4.0 (m, 1H), 3.65 (m, 2H), 3.3 (m, 1H), 2.85 (m, 2H), 2.22 (d, 2H), 2.15 (m, 2H), 2.0 (m, 1H), 1.9 (m, 1H), 1.4 (m, 2H).

EXAMPLE 7 trans-{4-[2-(4-Methyl-phenyl)-ethoxy]-cyclohexyl}-(1H-pyrazolo[3,4-d]pyrimidin-4-yl)-amine

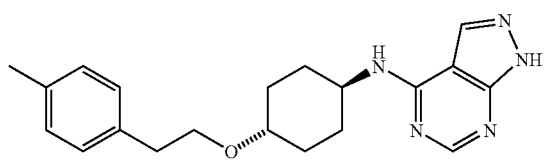

From 4-methyl-phenylacetic acid ethyl ester, using the procedure described for the preparation of Example 1, Step 3 gave trans-{4-[2-(4-methyl-phenyl)-ethoxy]-cyclohexyl}-(1H-pyrazolo[3,4-d]pyrimidin-4-yl)-amine as a white solid: MS (m+1)=352.2; 1H NMR (400 MHz, CDCl3) 8.42 (s, 1H), 7.92 (s, 1H), 7.1 (dd, 4H), 4.0 (m, 1H), 3.68 (m, 2H), 3.3 (m, 1H), 2.85 (m, 2H), 2.35 (s, 3H), 2.22 (d, 2H), 2.15 (d, 2H), 2.0 (m, 1H), 1.4 (m, 4H).

EXAMPLE 8 trans-{4-[2-(3-Fluoro-phenyl)-ethoxy]-cyclohexyl}-(1H-pyrazolo[3,4-d]pyrimidin-4-yl)-amine

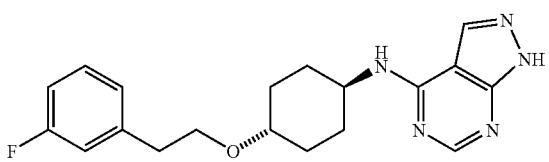

From 3-fluoro-phenylacetic acid methyl ester, using the procedure described for the preparation of Example 1, Step 3 gave trans-{4-[2-(3-fluoro-phenyl)-ethoxy]-cyclohexyl}-(1H-pyrazolo[3,4-d]pyrimidin-4-yl)-amine as a white solid: MS (m+1)=356.1; 1H NMR (400 MHz, CDCl3) 8.41 (s, 1H), 7.92 (s, 1H), 7.21 (m, 1H), 6.9 (m, 3), 4.1 (m, 1H), 3.68 (m, 2H), 3.3 (m, 1H), 2.85 (m, 2H), 2.22 (d, 2H), 2.15 (d, 2H), 1.6 (m, 1H), 1.45 (m, 2H), 1.2 (m, 2H).

EXAMPLE 9 trans-{4-[2-(2-Methyl-phenyl)-ethoxy]-cyclohexyl}-(1H-pyrazolo[3,4-d]pyrimidin-4-yl)-amine

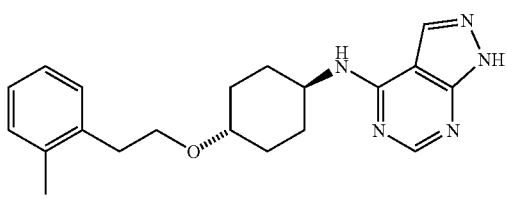

From 2-methyl-phenylacetic acid ethyl ester, using the procedure described for the preparation of Example 1, Step 3 gave trans-{4-[2-(2-methyl-phenyl)-ethoxy]-cyclohexyl}-(1H-pyrazolo[3,4-d]pyrimidin-4-yl)-amine as a white solid: MS (m+1)=352.1; 1H NMR (400 MHz, CDCl3) 8.42 (s, 1H), 7.92 (s, 1H), 7.15 (m, 4H), 4.0 (m, 1H), 3.68 (m, 2H), 3.3 (m, 1H), 2.85 (m, 2H), 2.34 (s, 3H), 2.22 (d, 2H), 2.15 (d, 2H), 1.7 (m, 1H), 1.5 (m, 2H), 1.4 (m, 2H).

EXAMPLE 10 trans-{4-[2-(3-Methyl-phenyl)-ethoxy]-cyclohexyl}-(1H-pyrazolo[3,4-d]pyrimidin-4-yl)-amine

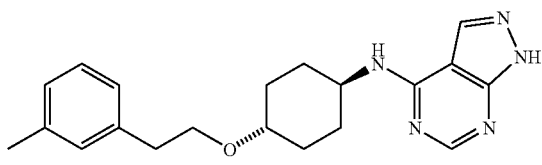

From 3-methyl-phenylacetic acid ethyl ester, using the procedure described for the preparation of Example 1, Step 3 gave trans-{4-[2-(3-methyl-phenyl)-ethoxy]-cyclohexyl}-(1H-pyrazolo[3,4-d]pyrimidin-4-yl)-amine as a white solid: MS (m+1)=352.4; 1H NMR (400 MHz, CDCl3) 8.42 (s, 1H), 7.92 (s, 1H), 7.2 (m, 1H), 7.0 (m, 3H), 4.0 (m, 1H), 3.68 (m, 2H), 3.3 (m, 1H), 2.85 (m, 2H), 2.33 (s, 3H), 2.22 (d, 2H), 2.15 (d, 2H), 1.7 (m, 1H), 1.5 (m, 2H), 1.4 (m, 2H).

EXAMPLE 11 trans-[4-(2-Fluoro-2-(2-fluorophenyl)-ethoxy-cyclohexyl)-(1H-pyrazolo[3,4-d]pyrimidin-4-yl)-amine

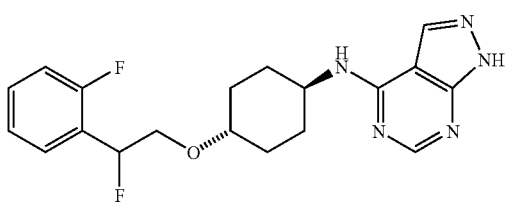

Step 1: trans (4-Hydroxy-cyclohexyl)-carbamic acid benzyl ester

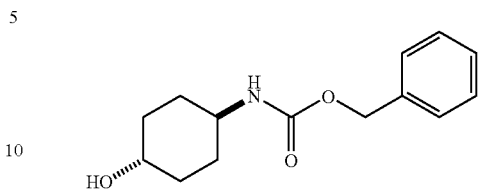

To an ice cold mixture of 50 g of trans 4-aminocyclohexanol in 500 mL of ethyl acetate and 500 mL of THF was added 200 mL of saturated sodium carbonate and the 65 mL of benzyl chloroformate drop-wise over 20 min. The mixture was allowed to warm and stir overnight and the precipitated product collected by filtration and washed with 200 mL of water. After drying under vacuum the white crystalline product weighed 84 g. The combined filtrates were shaken, separated and the aqueous layer extracted with 3×100 mL of ethyl acetate. The combined ethyl acetate extracts were dried over magnesium sulfate and concentrated under reduced pressure. Trituration with ether-hexane gave an additional 35.5 g of product as a white crystalline solid. MS (m+1)=250.4; 1H NMR (400 MHz, CDCl3) 7.4-7.3 (m, 5H), 5.1 (s, 2H), 4.6 (s, 1H), 3.6 (m, 1H), 3.5 (m, 1H), 2.0 (dd, 4H), 1.6 (d, 1H), 1.4 (dd, 2H), 1.2 (dd, 2H).

Step 2: trans (4-tert-Butyl-dimethyl-silanyloxy-cyclohexyl)-carbamic acid benzylester

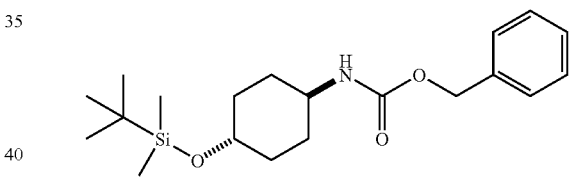

A mixture of 30.5 g of trans-(4-hydroxy-cyclohexyl)-carbamic acid benzylester, 23 g of tert-butyldimethylsilyl chloride, 64 g of imidazole and 55 mL of DMF was stirred for 24 h. The mixture was diluted with 250 mL of ether and washed with 4×250 mL portions of water, dried over magnesium sulfate and concentrated under reduced pressure. The product slowly crystallized under vacuum as a low melting solid: 45 g; 1H NMR (400 MHz, CDCl3) 7.4-7.3 (m, 5H), 5.1 (s, 2H), 4.6 (s, 1H), 3.6 (m, 1H), 3.5 (m, 1H), 2.0 (d, 2H), 1.8 (d, 2H), 1.6 (d, 1H), 1.4 (dd, 2H), 1.2 (dd, 2H), 0.9 (s, 9H), 1.05 (s, 6H).

Step 3: trans-[4-(2-Bromo-3-phenyl-allyloxy)-cyclohexyl]-carbamic acid benzyl ester

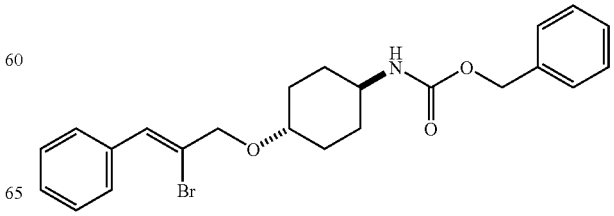

To a stirred mixture of 7.3 g of trans (4-tert-butyl-dimethyl-silanyloxy-cyclohexyl)-carbamic acid benzylester and 5.7 g of 2-bromocinnamaldehyde in 140 mL of anhydrous acetonitrile was added 0.57 g of bismuth tribromide. After 15 min, 5.8 mL of triethyl-silane was added drop-wise over 15 min. After stirring for 1 h, the reaction was complete by TLC analysis and was quenched with 50 mL of saturated sodium bicarbonate, allowed to stir until the black precipitated bismuth metal was consumed with the formation of a white precipitate and extracted with 3×250 mL portions of ethyl acetate. The combined extracts were dried over magnesium sulfate and concentrated under reduced pressure. Chromatography over silica gel eluting with a gradient of 0%-20% ethyl acetate in hexane gave 7.6 g (90%) of product as a white crystalline solid: MS (m+1)=444.3; 1H NMR (400 MHz, CDCl3) 7.6 (d, 2H), 7.35 (m, 8H), 7.07 (s 1H), 5.08 (s, 2H), 4.6 (s, 1H), 4.28 (s, 2H), 3.6 (m, 1H), 3.4 (m, 1H), 2.06 (d, 4H), 1.48 (dd, 2H), 1.2 (dd, 2H).

Step 4: trans-[4-(2-(2-Fluorophenyl)-3-phenyl-allyloxy)-cyclohexyl]-carbamic acid benzyl ester

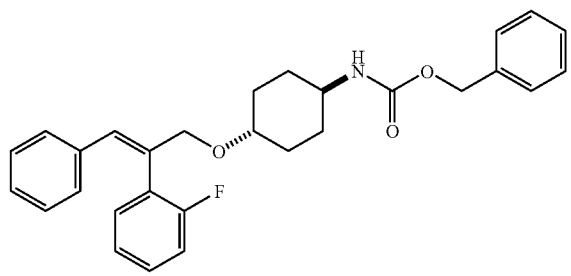

A stirred mixture of 0.44 g of trans-[4-(2-bromo-3-phenyl-allyloxy)-cyclohexyl]-carbamic acid benzyl ester, 0.15 g of 2-fluorophenylboronic acid, 0.47 g of barium hydroxide octahydrate, 25 mg of tetrakis-triphenylphosphine palladium, 6 mL of DME and 1 mL of water was heated to reflux for 12 h. The mixture was cooled and partitioned between 10 mL of sodium carbonate and 3×20 mL of ethyl acetate. The combined extracts were dried over magnesium sulfate and concentrated under reduced pressure. Chromatography over silica gel eluting with a gradient of 0%-20% ethyl acetate in hexane gave 0.42 g 460.2 of product as a white crystalline solid: MS (m+1)=460.4; 1H NMR (400 MHz, CDCl3) 7.3-7.2 (m, 9H), 7.1-6.95 (m, 5H), 6.8 (s 1H), 5.05 (s, 2H), 4.55 (s, 1H), 4.28 (s, 2H), 3.5 (m, 1H), 3.3 (m, 1H), 2.0 (m, 4H), 1.4 (dd, 2H), 1.15 (dd, 2H).

Step 5: Benzyl {trans-4-[2-(2-fluorophenyl)-2-hydroxyethoxy]cyclohexyl}carbamate

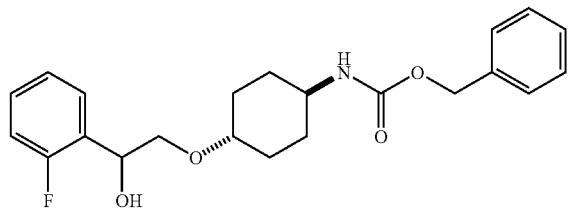

To a stirred solution of 41 g of trans-[4-(2-(2-fluorophenyl)-3-phenyl-allyloxy)-cyclohexyl]-carbamic acid benzyl ester in 750 mL of dichloromethane and 250 mL of methanol cooled to −78° C. was dispersed a stream of ozone from an ozone generator until a blue color persisted. The excess ozone was purged with nitrogen until the blue color dissipated, and 7.8 g of sodium borohydride was added. After warming to room temperature over 30 min, the solution was diluted with 50 mL of water and concentrated under reduced pressure. The residue was treated with 500 mL of 3N hydrochloric acid and extracted into 3×500 mL of ethyl acetate. The combined extracts were dried over magnesium sulfate and concentrated under reduced pressure. Chromatography over silica gel eluting with a gradient of 2%-30% ethyl acetate in hexane gave 30 g of product as a white crystalline solid: MS (m+1)=388.4; 1H NMR (400 MHz, CDCl3) 7.53 (m, 1H), 7.33 (m, 5H), 7.25 (m, 1H), 7.14 (m, 1H), 7.0 (m, 1H), 5.15 (d, 1H), 5.07 (s, 2H), 4.6 (m, 1H), 3.7 (d, 1H), 3.5 (br m, 1H), 3.4 (t, 1H), 3.3 (m, 1H), 2.9 (s, 1H), 2.0 (m, 4H), 1.2 (q, 2H), 1.15 (q, 2H).

Step 6: tert-butyl {trans-4-[2-(2-fluorophenyl)-2-hydroxyethoxy]-cyclohexyl}carbamate

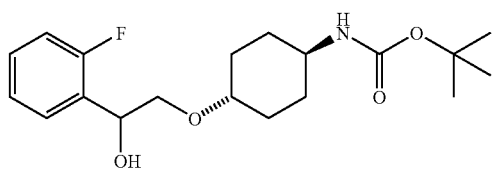

A solution of 26 g of benzyl {trans-4-[2-(2-fluorophenyl)-2-hydroxyethoxy]cyclohexyl}carbamate and 19.4 g of di-tert-butyldicarbonate in 300 mL of ethanol was stirred with 3 g of 10% palladium on carbon under 1 atm of hydrogen for 18 h. After removal of the catalyst by filtration and concentration under reduced pressure the product was crystallized by trituration with hexane. Drying under reduced pressure gave 24 g of product as a white crystalline solid: MS (m+1)=354.4; 1H NMR (400 MHz, CDCl3) 7.52 (m, 1H), 7.25 (m, 1H), 7.18 (m, 1H), 7.0 (m, 1H), 5.17 (d, 1H), 4.4 (br s, 1H), 3.7 (d, 1H), 3.4 (m, 2H), 3.3 (m, 1H), 2.9 (s, 1H), 2.0 (d, 4H), 1.43 (s, 9H), 1.4 (m, 2H), 1.15 (q, 2H).

Step 7: tert-butyl {trans-4-[2-fluoro-2-(2-fluorophenyl)ethoxy]cyclohexyl}carbamate

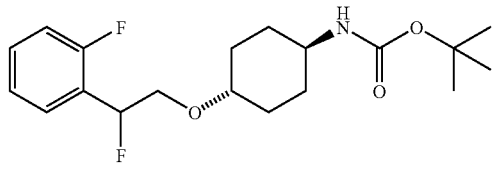

A solution of 18 g of tert-butyl {trans-4-[2-(2-fluorophenyl)-2-hydroxyethoxy]-cyclohexyl}carbamate in 200 mL of dichloromethane was added over 30 min to a solution of 23 g of diethyl-amino sulfur-trifluoride in 800 mL of dichloromethane cooled to −78° C. under nitrogen atmosphere. The mixture was allowed stir for 1 h at −78° C. then quenched with 100 mL of saturated sodium carbonate. After stirring for 15 min the layers were separated. The organic layer was dried over magnesium sulfate and concentrated under reduced pressure. Chromatography over silica gel eluting with a gradient of 2%-25% ethyl acetate in hexane gave 12 g of product as a white crystalline solid: 1H NMR (400 MHz, CDCl3) 7.45 (m, 1H), 7.3 (m, 1H), 7.2 (m, 1H), 7.06 (m, 1H), 5.15 (dm, JH-F=48 Hz), 4.18 (br s, 1H), 3.65 (complex m, 2H), 3.42 (br s, 1H), 3.3 (m, 1H), 2.0 (d, 4H), 1.42 (s, 9H), 1.4 (q, 2H), 1.15 (q, 2H).

Step 8: trans-4-[2-fluoro-2-(2-fluorophenyl)ethoxy]cyclohexanamine

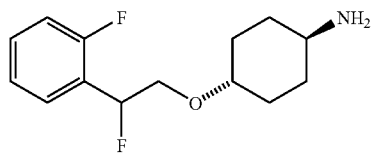

A mixture of 1 g of tert-butyl {trans-4-[2-fluoro-2-(2-fluorophenyl)ethoxy]-cyclohexyl}carbamate an 10 mL of 4N HCl in dioxane was stirred at room temperature for 3 h then concentrated to dryness under reduced pressure. The white crystalline hydrochloride salt could be converted into the free base by partitioning between 25 mL of 3N sodium hydroxide and 3×25 mL portions of chloroform. The combined extracts were dried over magnesium sulfate and concentrated under reduced pressure. Further drying under vacuum gave 0.72 g of product as an oil which crystallized on standing: MS (m+1)= 256.4; 1H NMR (400 MHz, CDCl3) 7.45 (m, 1H), 7.3 (m, 1H), 7.17 (m, 1H), 7.04 (m, 1H), 5.85 (dd, JHF=47 Hz, 1H), 3.75 (m, 2H), 3.3 (m, 1H), 2.7 (m, 1H), 2.02 (m, 2H), 1.85 (m, 2H), 1.3 (m, 2H), 1.05 (m, 2H).

Step 9: N-{trans-4-[2-fluoro-2-(2-fluorophenyl)ethoxy]cyclohexyl}-1-(tetrahydro-2H-pyran-2-yl)-1H-pyrazolo[3,4-d]pyrimidin-4-amine

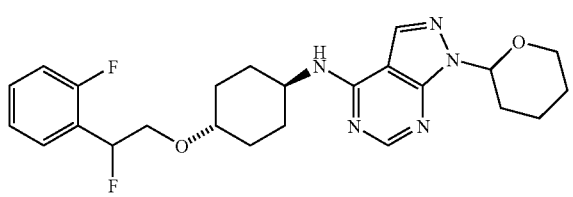

A mixture of 0.52 g trans-4-[2-fluoro-2-(2-fluorophenyl)ethoxy]-cyclohexanamine hydrochloride, 0.46 g of 4-chloro-1-(tetrahydro-pyran-2-yl)-1H-pyrazolo[3,4-d]pyrimidine, and 1 g of powdered sodium carbonate in 25 mL of 2-propanol was heated to 80° C. under nitrogen overnight. The mixture was cooled, filtered and the solid washed with 3×50 mL portions of 10% methanol in chloroform. The combined extracts were concentrated under reduced pressure. Chromatography over silica gel eluting with a gradient of 50%-100% ethyl acetate in hexane gave 0.82 g of product as a white solid: MS (m+1)=458.4.

Step 10: trans-[4-(2-Fluoro-2-(2-fluorophenyl)-ethoxy-cyclohexyl)-(1H-pyrazolo[3,4-d]pyrimidin-4-yl)-amine

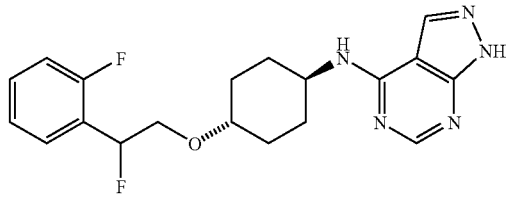

A mixture of 0.82 g of N-{trans-4-[2-fluoro-2-(2-fluorophenyl)ethoxy]cyclohexyl}-1-(tetrahydro-2H-pyran-2-yl)-1H-pyrazolo[3,4-d]pyrimidin-4-amine in 75 mL of 2-propanol and 2 mL of 12N HCl and heated to 90° C. for 1 h, cooled and concentrated under reduced pressure to dryness. The solid residue was triturated with 50 mL of ether and filtered. The solid hydrochloride salt was dissolved in 100 mL of methanol and 2 mL of concentrated aqueous ammonia and again concentrated to dryness. The resulting residue was extracted with 100 mL of chloroform, filtered and concentrated to dryness under reduced pressure. Chromatography over silica gel eluting with a gradient of 5%-10% methanol in ethyl acetate gave 0.67 g of product as a white solid: MS (m+1)=374.43; 1H NMR 8.4 (s, 1H), 7.95 (s, 1H), 7.48 (m, 1H), 7.38 (m, 1H), 7.2 (m, 1H), 7.05 (m, 1H), 5.85 (m, J$_{HF}$=47 Hz, 1H), 3.8 (m, 3H), 3.42 (br s, 1H), 2.25 (d, 2H), 2.18 (d, 2H), 1.58 (q, 2H), 1.4 (br m, 2H).

Resolution into the pure enantiomers could be performed by isocratic elution on ChiralPak AD at 1 mL/min, eluting with 20% methanol in 2-propanol.

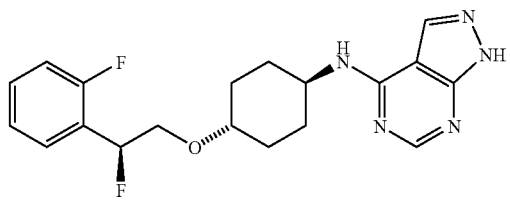

trans-[4-((2R)-2-Fluoro-2-(2-fluorophenyl)-ethoxy-cyclohexyl)-(1H-pyrazolo[3,4-d]pyrimidin-4-yl)-amine: $[\alpha]_D^{25° C.}$=−22.3° (c=1, MeOH) MS (m+1)=374.4; 1H NMR (400 MHz, CDCl$_3$) 8.4 (s, 1H), 7.95 (s, 1H), 7.48 (m, 1H), 7.38 (m, 1H), 7.2 (m, 1H), 7.05 (m, 1H), 5.85 (m, J$_{HF}$=47 Hz, 1H), 3.8 (m, 3H), 3.42 (br s, 1H), 2.25 (d, 2H), 2.18 (d, 2H), 1.58 (q, 2H), 1.4 (br m, 2H).

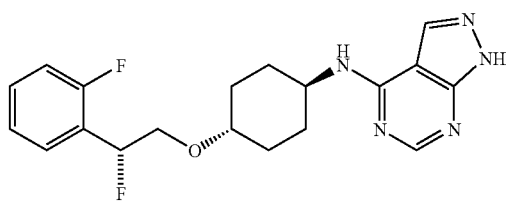

trans-[4-((2R)-2-Fluoro-2-(2-fluorophenyl)-ethoxy-cyclohexyl]-(1H-pyrazolo[3,4-d]pyrimidin-4-yl)-amine:
$[\alpha]_D^{25°\,C.}$=−22.3° (c=1, MeOH) MS (m+1)=374.4; 1H NMR (400 MHz, CDCl$_3$) 8.4 (s, 1H), 7.95 (s, 1H), 7.48 (m, 1H), 7.38 (m, 1H), 7.2 (m, 1H), 7.05 (m, 1H), 5.85 (m, $J_{HF}$=47 Hz, 1H), 3.8 (m, 3H), 3.42 (br s, 1H), 2.25 (d, 2H), 2.18 (d, 2H), 1.58 (q, 2H), 1.4 (br m, 2H).

EXAMPLE 12 trans-[4-(2-Fluoro-2-(2-methylphenyl)-ethoxy-cyclohexyl]-(1H-pyrazolo[3,4-d]pyrimidin-4-yl)-amine

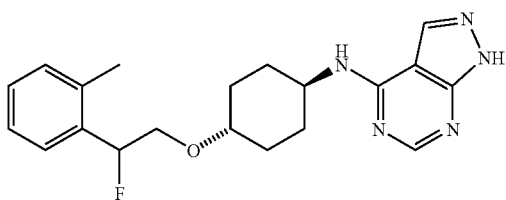

Step 1: trans-[4-(2-(2-Methylphenyl)-3-phenyl-allyloxy)-cyclohexyl]-carbamic acid benzyl ester

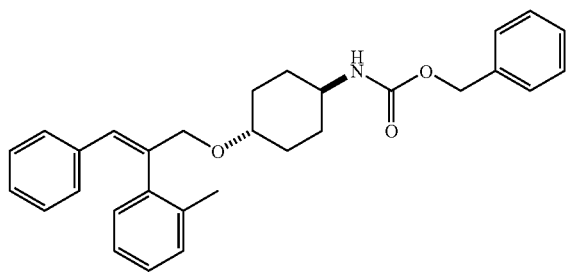

From trans-[4-(2-bromo-3-phenyl-allyloxy)-cyclohexyl]-carbamic acid benzyl ester, and 2-methylphenylboronic acid using the procedure described above for Example 11, Step 4, gave the product as a white crystalline solid: MS (m+1)= 456.5; 1H NMR (400 MHz, CDCl3) 7.3 (m, 2H), 7.2 (m, 7H), 7.05 (m, 3H), 6.85 (m, 2H), 6.66 (s 1H), 5.05 (s, 2H), 4.55 (s, 1H), 4.28 (s, 2H), 3.5 (m, 1H), 3.42 (s, 3H), 3.3 (m, 1H), 2.0 (m, 4H), 1.4 (dd, 2H), 1.15 (dd, 2H).

Step 2: trans-[4-(2-Fluoro-2-(2-methylphenyl)-ethoxy-cyclohexyl]-(1H-pyrazolo[3,4-d]pyrimidin-4-yl)-amine

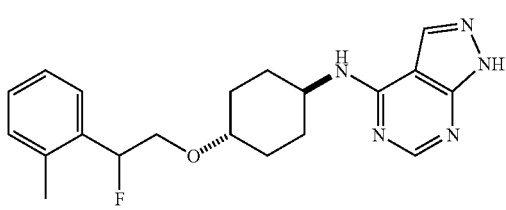

From trans-[4-(2-(2-methyl-phenyl)-3-phenyl-allyloxy)-cyclohexyl]-carbamic acid benzyl ester, using the procedures described for Example 11, Step 5 above gave product as a white solid: MS (m+1)=370.4

Resolution into the pure enantiomers could be performed by isocratic elution on ChiralPak AD at 1 mL/min, eluting with 20% methanol in 2-propanol.

EXAMPLE 13 cis-(4-Phenethyloxy-cyclohexylmethyl)-(1H-pyrazolo[3,4-d]pyrimidin-4-yl)-amine

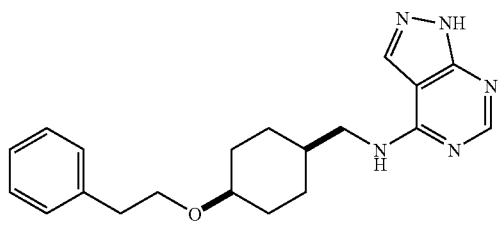

Step 1: cis-4-Hydroxy-cyclohexanecarboxylic acid ethyl ester

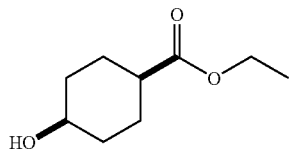

A mixture of 10 g of ethyl 4-hydroxybenzoate, 5 mL of acetic acid, 0.8 g of 5% rhodium on alumina, and 200 mL of ethanol was shaken under 55 psi of hydrogen for 48 h, filtered and concentrated under reduced pressure. The residue was taken up in 200 mL of toluene and again concentrated under reduced pressure to remove acetic acid. Drying under vacuum overnight gave 11 g of product, which was predominantly cis (83:17 cis: trans by HPLC), as a colorless oil: MS (m+1)= 173.2; 1H NMR (400 MHz, CDCl3) 4.1 (dd, 2H), 3.9 (m, cis isomer, 0.85H), 3.6 (m, trans isomer, 0.15H), 2.4 and 2.2 (m, 1H), 2.0 (m, 2H), 1.62 (m, 6H), 1.2 (t, 3H).

Step 2: cis-4-tert-Butyl-dimethylsilanyloxy-cyclohexanecarboxylic acid ethyl ester

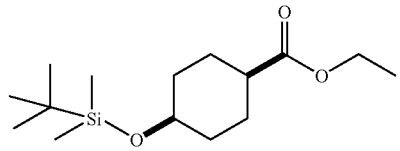

A mixture of 3 g of cis-4-hydroxy-cyclohexanecarboxylic acid ethyl ester, 3 g of imidazole, 33 g of tert-butyldimethylsilyl-chloride, and 6 mL of DMF was stirred under inert atmosphere overnight. The mixture was diluted with 250 mL of water and extracted into 3×50 mL portions of ether. The combined ether extracts were washed with 2×50 mL of water, dried over magnesium sulfate and concentrated under reduced pressure. Drying under vacuum overnight gave 4.5 g of product as a colorless oil: 1H NMR (400 MHz, CDCl3) 4.1 (dd, 2H), 3.58 (m, cis isomer, 0.85H), 2.2 (m, 1H), 1.95 (m, 4H), 1.6 (m, 1H), 1.5 (m, 1H), 1.22 (m, 6H), 0.9 (s, 9H), 0.04 (s, 6H).

Step 3:
cis-2-(4-Phenethyloxy)-cyclohexanecarboxylic acid ethyl ester

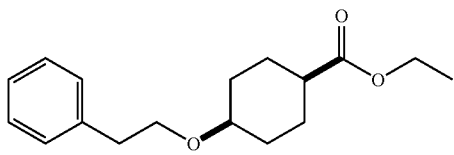

From 4 g of cis-4-tert-butyl-dimethylsilanyloxy-cyclohexanecarboxylic acid ethyl ester, using the procedure described for Example 1, Step 3 above, gave 3 g of a colorless resin: MS (m+1)=277.2.

Step 4: cis-(4-Phenethyloxy-cyclohexyl) methanol

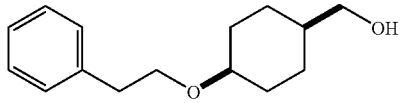

To a stirred, ice cold solution of 3 g of cis-2-(4-phenethyloxy)-cyclohexanecarboxylic acid ethyl ester, in 50 mL of THF was added 10 mL of 1M lithium aluminum hydride in THF. The mixture was allowed to warm to room temperature and stir for 1 h, then cooled in an ice bath and quenched with sequential addition of 0.5 mL of water, 0.5 mL of 1N sodium hydroxide, and 1.5 mL of water. After stirring for 30 min, the mixture was filtered, washed with 2×25 mL of ethyl acetate and combined extracts dried over magnesium sulfate and concentrated under reduced pressure: MS (m+1)=235.2, 1H NMR (400 MHz, CDCl3) 7.2 (m, 5H), 3.6 (t, 2H), 3.35 (m, 1H), 3.25 (m, 2H), 2.8 (t, 2H), 1.85 (d, 2H), 1.6-1.2 (complex m, 7H).

Step 5:
cis-2-(4-Phenethyloxy-cyclohexyl)-methylamine

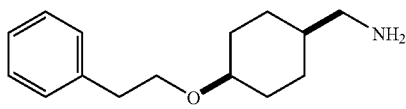

To a stirred, ice cold solution of 1.2 g of cis-(4-phenethyloxy-cyclohexyl) methanol and 1.5 mL of triethylamine, in 60 mL of dichloromethane was added 1.5 mL of methane-sulfonyl chloride drop-wise over 10 min. The mixture was allowed to stir for 30 min, then concentrated under reduced pressure and diluted with 50 mL of ether and washed with 25 mL of 10% HCl, 25 mL of water, 25 mL of saturated sodium carbonate. The combined extracts were dried over magnesium sulfate and concentrated under reduced pressure. The crude mesylate, 1.6 g, was used without further purification: 1H NMR (400 MHz, CDCl3) 7.2 (m, 5H), 4.0 (d, 2H), 3.6 (m, 3H), 3.0 (s, 3H), 2.85 (t, 2H), 1.95 (d, 2H), 1.8-1.2 (complex m, 9H). The mesylate was taken up in 20 mL of DMF and heated to reflux with 2 g of sodium azide to 80° C. overnight, cooled, filtered, and concentrated under reduced pressure (bath temp=60° C.) to remove most of the DMF. The residue was diluted with 50 mL of ether and washed with 2×50 mL of water, dried over magnesium sulfate and concentrated under reduced pressure. The crude azide, 1.5 g, was used without further purification: 1H NMR (400 MHz, CDCl3) 7.2 (m, 5H), 3.6 (t, 2H), 3.56 (m, 1H), 3.1 (d, 2H), 2.95 (t, 2H), 1.95 (d, 2H), 1.8-1.2 (complex m, 9H). To a stirred, ice cold solution of the crude azide in 12 mL of ethanol was added 0.3 g of sodium borohydride and then 0.9 g of nickel chloride hexahydrate. The resulting black mixture was stirred for 2 h, diluted with 50 mL of saturated sodium carbonate and extracted with 3×50 mL of chloroform. The combined extracts were dried over magnesium sulfate and concentrated under reduced pressure. Drying under vacuum gave 1.45 g of a thick oil: MS (m+1)=235.2, 1H NMR (400 MHz, CDCl3) 7.2 (m, 5H), 3.6 (t, 2H), 3.55 (m, 1H), 2.88 (t, 2H), 1.85 (d, 2H), 1.7-1.2 (complex m, 7H).

Step 6: cis-(4-Phenethyloxy-cyclohexylmethyl)-(1H-pyrazolo[3,4-d]pyrimidin-4-yl)-amine

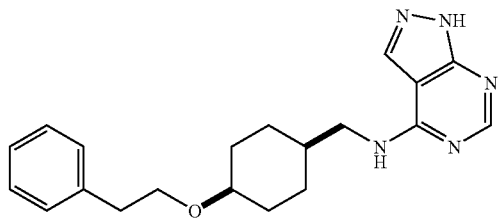

A mixture of 0.3 g of cis-2-(4-phenethyloxy-cyclohexyl)-methylamine, 0.2 g of 4-chloro-1H-pyrazolo[3,4-d]pyrimidine (R. K. Robins, J. Amer. Chem. Soc., 78, 784-790 (1956)), 10 mL of 2-propanol and 0.2 mL of N,N-diisopropyl-ethylamine was heated to 80° C. for 12 hours. The mixture was cooled and concentrated under reduced pressure and purified by preparative TLC eluting with 80:20:5 TBF:diethyl ether:NH4OH and preparative reverse phase chromatography on ChiralPak AD eluting with 80:20 hexane (0.1% diethylamine): ethanol gave 0.22 g of product as a white crystalline solid. MS (m+1)=352.3; 1H NMR (400 MHz, CDCl3) 8.4 (s, 1H), 7.92 (s, 1H), 7.2 (m, 5H), 3.6 (t, 2H), 3.55 (m, 1), 3.5 (m, 2H), 2.85 (t, 2H), 1.9 (m, 2H), 1.7 (m, 1H), 1.8-1.5 (m, 5H), 1.4 (m, 4H).

EXAMPLE 14 trans-(4-Phenethyloxymethyl-cyclohexyl)-(1H-pyrazolo[3,4-d]pyrimidin-4-yl)-amine

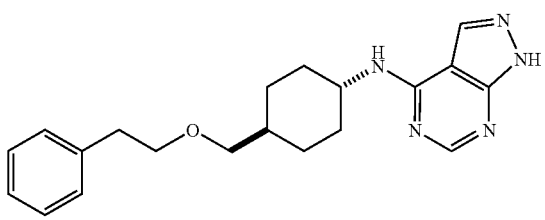

Step 1: cis-4-Methanesulfonyloxy-cyclohexanecarboxylic acid ethyl ester

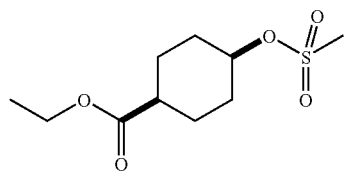

To a stirred, ice cold solution of 1.8 g of cis-4-hydroxy-cyclohexanecarboxylic acid ethyl ester, and 2.8 mL of triethylamine, in 25 mL of dichloromethane was added 0.85 mL of methane-sulfonyl chloride drop-wise over 10 min. The mixture was allowed to stir for 30 min, then concentrated under reduced pressure and diluted with 50 mL of ether and washed with 25 mL of 10% HCl, 25 mL of water, 25 mL of saturated sodium carbonate. The combined extracts were dried over magnesium sulfate and concentrated under reduced pressure. The crude mesylate, 2.5 g, was used without further purification: 1H NMR (400 MHz, CDCl3) 4.92 (m, 1H), 4.15 (q, 2H), 3.02 (s, 3H), 2.4 (m, 1H), 2.05 (m, 2H), 1.92 (m, 2H), 1.62-1.4 (complex m, 4H).

Step 2: cis-4-Methanesulfonic acid 4-hydroxymethyl-cyclohexyl ester

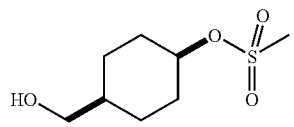

To a stirred solution of 2.5 g of cis-4-methanesulfonyloxy-cyclohexanecarboxylic acid ethyl ester in 30 mL of 1,2-dimethoxyethane was added 10 mL of 1M lithium borohydride in THF. The mixture was allowed to stir for overnight, then cooled in an ice bath and quenched by careful addition of 100 mL of 2N HCl and extracted into 3×50 mL portions of ethyl acetate. The combined extracts were and washed with 25 mL of saturated sodium carbonate, dried over magnesium sulfate, diluted with 50 mL of toluene and concentrated under reduced pressure. The crude hydroxy-mesylate, 1.8 g, was used without further purification: 1H NMR (400 MHz, CDCl3) 5.0 (m, 1H), 4.15 (m, 1H), 3.6 (m, 2H), 3.02 (s, 3H), 2.05 (m, 2H), 1.92 (m, 1H), 1.6 (complex m, 4H), 1.4 (dd, 2H).

Step 3: cis-Methanesulfonic acid 4-(tert-butyl-dimethyl-silanyloxymethyl-cyclohexyl ester

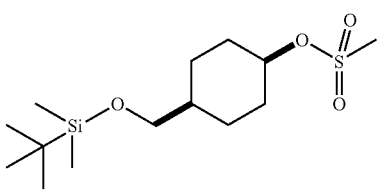

A mixture of 1.8 g of cis-4-methanesulfonic acid 4-hydroxymethyl-cyclohexyl, 1.7 g of imidazole, 1.8 g of tert-butyldimethylsilyl-chloride, and 4 mL of DMF was stirred under inert atmosphere overnight. The mixture was diluted with 100 mL of water and extracted into 3×25 mL portions of ether. The combined ether extracts were washed with 2×50 mL of water, dried over magnesium sulfate and concentrated under reduced pressure. Chromatography over silica gel using a gradient elution of 5% to 30% ethyl acetate in hexane gave first a 0.1 g of the trans isomer, 0.5 g of mixed fractions, then 0.9 g of pure cis product as a colorless thick oil: 1H NMR (400 MHz, CDCl3) 5.0 (m, 1H), 3.4 (d, 2H), 3.0 (s, 3H), 2.05 (m, 2H), 1.6 (m, 5H), 1.4 (m, 2H), 0.9 (s, 9H), 0.02 (s, 6H).

Step 4: cis-Methanesulfonic acid 4-phenethyloxymethyl-cyclohexyl ester

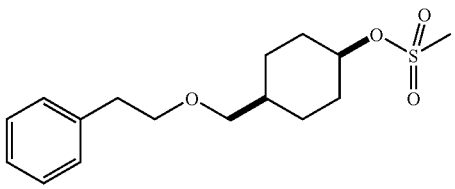

From 0.9 g of cis-methanesulfonic acid 4-(tert-butyl-dimethyl-silanyloxymethyl-cyclohexyl ester, 20 mL of anhydrous acetonitrile, 2.6 mL of triethyl silane, 1.6 mL of phenylacetaldehyde and 0.25 g of bismuth tribromide using the procedure described for Example 1, Step 3 above (chromatography using gradient elution 10%-35% ethyl acetate in hexane), gave 0.8 g of a colorless resin: 1H NMR (400 MHz, CDCl3) 7.3-7.2 (m, 5H), 5.0 (m, 1H), 3.62 (t, 2H), 3.28 (d, 2H), 3.0 (s, 3H), 2.88 (t, 2H), 2.05 (m, 2H), 1.65 (m, 4H), 1.58 (m, 1H), 1.4 (m, 2H).

Step 5:
trans-4-Phenethyloxymethyl-cyclohexylamine

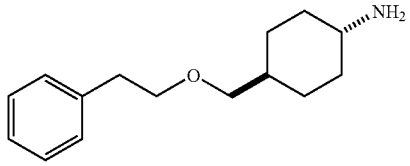

A stirred mixture of 0.8 g of cis-methanesulfonic acid 4-phenethyloxymethyl-cyclohexyl ester, 10 mL of DMF, and 1.8 g of sodium azide was heated to reflux with to 80° C. overnight, cooled, filtered, and concentrated under reduced pressure (bath temp=60° C.) to remove most of the DMF. The residue was diluted with 50 mL of ether and washed with 2×50 mL of water, dried over magnesium sulfate and concentrated under reduced pressure. The crude trans-azide, 0.8 g, was used without further purification: 1H NMR (400 MHz, CDCl3) 7.25-7.2 (m, 5H), 3.6 (t, 2H), 3.2 (overlapping m, 3H), 2.87 (t, 2H), 2.05 (d, 2H), 1.82 (d, 2H), 1.56 (m, 1H), 1.3 (m, 2H), 1.0 (dd, 2H).

A mixture of 0.8 g of the crude azide and 0.2 g of 10% palladium on carbon in 50 mL of ethanol was stirred under 1 atm of hydrogen for 4 h, filtered and concentrated under reduced pressure. Drying under vacuum gave 0.8 g of a thick oil: MS (m+1)=235.1, 1H NMR (400 MHz, CDCl3) 7.25-7.2 (m, 5H), 3.6 (t, 2H), 3.22 (d, 2H), 2.88 (t, 2H), 2.6 (m, 1H), 1.84 (d, 2H), 1.8 (d, 2H), 1.5 (m, 1H), 1.0 (m, 4H).

Step 6: trans-(4-Phenethyloxymethyl-cyclohexyl)-(1H-pyrazolo[3,4-d]pyrimidin-4-yl)-amine

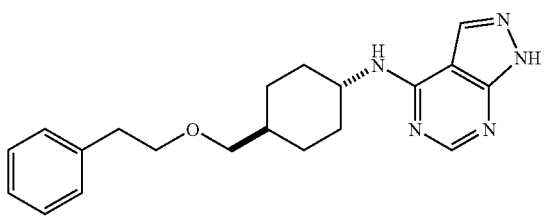

A mixture of 0.13 g of trans-4-phenethyloxymethyl-cyclohexylamine (Compound 45), 0.08 g of 4-chloro-1H-pyrazolo[3,4-d]pyrimidine (R. K. Robins, J. Amer. Chem. Soc., 78, 784-790 (1956)), 10 mL of 2-propanol and 0.1 mL of N,N-diisopropyl-ethylamine was heated to 80° C. for 12 hours. The mixture was cooled and concentrated under reduced pressure and purified by preparative TLC eluting with 90:10 THF:NH4OH: gave 0.15 g of product as a white crystalline solid. MS (m+1)=352.1; 1H NMR (400 MHz, CDCl3) 8.4 (s, 1H), 7.92 (s, 1H), 7.3-7.2 (m, 5H), 3.62 (t, 2H), 3.55 (m, 1H), 3.3 (d, 2H), 2.9 (t, 2H), 2.2 (d, 2H), 2.1 (s, 1H), 1.9 (d, 2H), 1.6 (m, 1H), 1.3 (m, 2H), 1.2 (dd, 2H).

EXAMPLE 15 cis-3-Phenyl-1-{3-[2-(1H-pyrazolo[3,4-d]pyrimidine4-ylamino)-ethyl]-cyclobutyl}-propan-1-ol

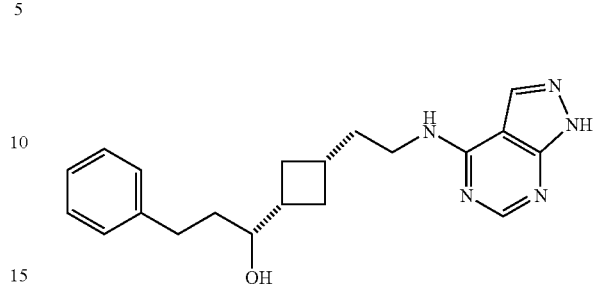

Step 1: 3-tert-Butoxycarbonylmethylene-cyclobutanecarboxylic acid

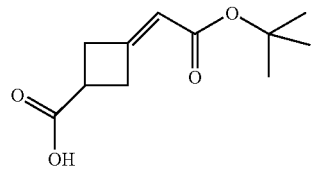

A mixture of 1.2 g of cyclobutanone-3-carboxylic acid (Pigou, P. E.; Shiesser, C. H.; J. Org. Chem. 53, 3841-3, 1988), 2.8 g of tert-butyl-dimethyl phosphono-acetate, 1.0 g of lithium hydroxide which had been dried at 120° C. for 30 min under vacuum, 6 g of activated 4A (heated in microwave oven then dried under vacuum for 1 h) molecular sieve dust and 50 mL of THF was heated to reflux under nitrogen for 24 h, cooled, diluted with 100 mL of ethyl acetate and 100 mL of 1N HCl and filtered through diatomaceous earth. The layers were separated and the aqueous layer extracted 4× mL of ethyl acetate. The combined organic extracts were diluted with 50 mL of toluene and concentrated under reduced pressure. Drying under vacuum overnight gave 2 g of product as a white crystalline solid: 1H NMR (400 MHz, CDCl3) 5.5 (s, 1H), 3.9-3.0 (complex m, 4H), 1.42 (s, 9H).

Step 2: cis-3-tert-Butoxycarbonylmethyl-cyclobutanecarboxylic acid

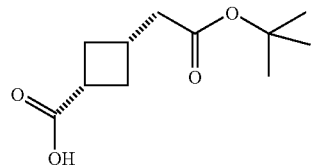

A mixture of 2 g of 3-tert-butoxycarbonylmethylene-cyclobutanecarboxylic acid, 150 mL of ethanol, 0.5 g of 5% platinum on carbon, and 200 mL of ethanol was stirred under 1 atm of hydrogen for 48 h overnight, filtered, diluted with 20 mL of toluene and concentrated under reduced pressure. Drying under vacuum overnight gave 2 g of product, which was predominantly as a colorless oil: 1H NMR (400 MHz, CDCl3) 10.2 (br s, 1H), 3.0 (m, 1H), 2.3 (m, 1H), 2.38 (m, 4H), 2.0 (dd, 2H), 1.4 (s, 9).

Step 3: cis-[3-(Methoxy-methyl-carbamoyl)-cyclobutyl]-acetic acid tert-butyl ester

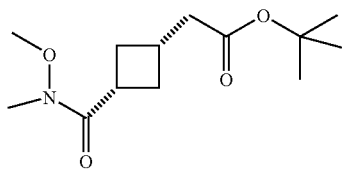

To an ice cold solution of 1.74 g of cis-3-tert-butoxycarbonylmethyl-cyclobutanecarboxylic acid, 3 mL of N-methyl-piperidine, and 50 mL of dichloromethane was added 1.7 mL of isobutyl chloroformate drop-wise over 5 min. After an additional 5 min, 1.6 g of N-methyl-N-methoxy-amine hydrochloride was added and the mixture allowed to warm with stirring overnight. The resulting mixture was diluted with 100 mL of dichloromethane, washed with 100 mL of water, 100 mL of 0.1 N HCl, 50 mL of saturated sodium carbonate and dried over magnesium sulfate. The solution was diluted with 50 mL of toluene and concentrated under reduced pressure. Drying under vacuum overnight gave 2.08 g of product as a colorless thick oil: MS (m+1)=258.3; 1H NMR (400 MHz, CDCl3) 3.62 (s, 3H), 3.16 (s, 3H), 2.35 (d, 2H), 2.0 (dd, 1H), 1.4 (s, 9H).

Step 4: cis-[3-(Methoxy-methyl-carbamoyl)-cyclobutyl]-acetic acid

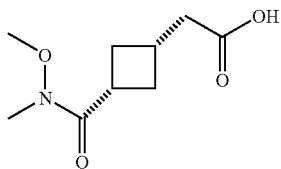

To an ice cold solution of 2 g of cis-[3-(methoxy-methyl-carbamoyl)-cyclobutyl]-acetic acid tert-butyl ester in 25 mL of dichloromethane was added 10 mL of trifluoroacetic acid. The mixture was allowed to warm and stir for 2 h then concentrated under reduced pressure. The residue was taken up in 3×50 mL of toluene and repeatedly concentrated under reduced pressure to remove trifluoroacetic acid. Drying under vacuum overnight gave 1.6 g of product as a colorless oil: MS (m+1)=202.3; 1H NMR (400 MHz, CDCl3) 9.0 (br s, 1H), 3.62 (s, 3H), 3.18 (s, 3H), 2.65 (m, 1H), 2.5 (overlapping d and m, 3H), 2.4 (dd, 1H), 2.0 (, m, 2H).

Step 5: cis-3-(2-Hydroxy-ethyl)-cyclobutanecarboxylic acid methoxy-methyl-amide

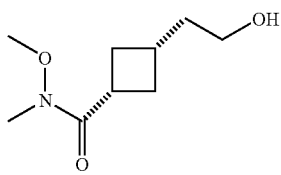

To an ice cold solution of 3.0 g of cis-[3-(methoxy-methyl-carbamoyl)-cyclobutyl]-acetic acid in 50 mL of THF was added 15 mL of 1M borane in THF. The mixture was allowed to stir for 15 min in the cold, then warm and stir for 30 min. The reaction was quenched with 25 mL of 10% HCl and extracted into 3×50 mL of ethyl acetate. The combined extracts were diluted with 50 mL of toluene, dried over magnesium sulfate and concentrated under reduced pressure. Drying under vacuum overnight gave 1.8 g of product as a colorless oil: MS (m+1)=188.45; 1H NMR (400 MHz, CDCl3) 3.62 (s, 3H), 3.6 (t, 2H), 3.18 (s, 3H), 2.35 (m, 1H), 2.3 (m, 3H), 1.984 (dd, 2H), 1.65 (dd, 2H).

Step 6: cis-{2-[3-Methoxy-methyl-carbamoyl)-cyclobutyl]-ethyl}-carbamic acid tert-butyl ester

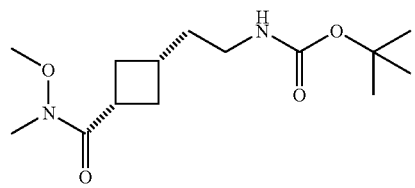

To an ice cold, stirred solution of 1.8 g of cis-3-(2-hydroxy-ethyl)-cyclobutane-carboxylic acid methoxy-methyl-amide, and 2.8 mL of triethylamine, in 100 mL of dichloromethane was added 0.8 mL of methane-sulfonyl chloride drop-wise over 10 min. The mixture was allowed to stir for 30 min, then concentrated under reduced pressure and diluted with 50 mL of ether and washed with 25 mL of 10% HCl, 25 mL of water, 25 mL of saturated sodium carbonate. The combined extracts were dried over magnesium sulfate and concentrated under reduced pressure. The crude mesylate, 2.6 g, was used without further purification: 1H NMR (400 MHz, CDCl3) 4.2 (t, 2H), 3.62 (s, 3H), 3.2 (m, 1H), 3.18 (s, 3H), 3.0 (s, 3H), 2.42-2.2 (complex m, 3H), 2.0 (m, 2H), 1.98 (dd, 2H). The mesylate was taken up in 30 mL of DMF and heated to reflux with 6 g of sodium azide to 85° C. overnight, cooled, filtered, and concentrated under reduced pressure (bath temp=60° C.) to remove most of the DMF. The residue was diluted with 50 mL of ether and washed with 2×50 mL of water, dried over magnesium sulfate and concentrated under reduced pressure. The crude azide, 1.5 g, was used without further purification: 1H NMR (400 MHz, CDCl3) 3.62 (s, 3H), 3.18 (t, 2H), 3.18 (s, 3H), 2.5-2.2 (complex m, 4H), 2.0 (m, 2H), 1.7 (dd, 2H). A mixture of the 1.2 g of crude azide, 1.5 g of di-tert-butyl-di-carbonate, 0.4 g of 10% palladium on carbon and 50 mL of ethyl acetate was stirred under 1 atm of hydrogen for 1 h, filtered, and concentrated under reduced pressure. Drying under vacuum gave 1.6 g of a thick oil. Chromatography over silica gel eluting with 50% ethyl acetate in hexane gave 1.2 g of the pure cis isomer as an oil: MS (m+1)=287.7, 1H NMR (400 MHz, CDCl3) 3.62 (s, 3H), 3.18 (s, 3H), 3.05 (m, 2H), 2.25 (m, 3H), 1.95 (m, 2H), 1.65 (m, 1H), 1.6 (dd, 2H), 1.42 (s, 9H).

Step 7: cis-{2-[3-(3-Phenyl-propionyl)-cyclobutyl]-ethyl}-carbamic acid tert-butyl ester

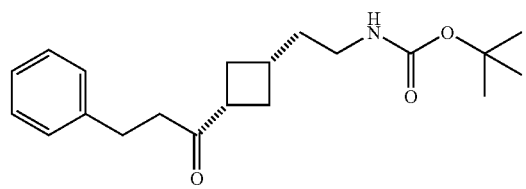

To an ice cold solution of 0.6 g of cis-{2-[3-methoxy-methyl-carbamoyl)-cyclobutyl]-ethyl}-carbamic acid tert-butyl ester in 10 mL of THF was added 9 mL of freshly prepared 0.7M phenethyl magnesium bromide (from phenethyl bromide and magnesium turnings in THF). After warming and stirring for 2 h, the reaction was quenched with 25 mL of 10% citric acid and extracted into 3×25 mL portions of ethyl acetate. The combined extracts were dried over magnesium sulfate and concentrated under reduced pressure. Drying under vacuum overnight gave 0.9 g of crude product as a colorless oil: MS (m+1)=332.7, 1H NMR (400 MHz, CDCl3) 7.3-7.1 (m, 5H), 3.05 (m, 2H), 2.9 (t, 2H), 2.65 (m, 2H), 2.2 (m, 3H), 1.8 (m, 1H), 1.6-1.5 (dd, 2H), 1.42 (s, 9H).

Step 8: cis-{2-[3-(1-Hydroxy-3-phenyl-propyl)-cyclobutyl]-ethyl}-carbamic acid tert-butyl ester

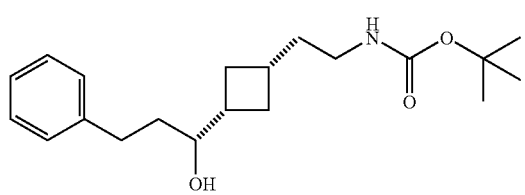

To an ice cold solution of 0.9 g of cis-{2-[3-(1-hydroxy-3-phenyl-propyl)-cyclobutyl]-ethyl}-carbamic acid tert-butyl ester in 50 mL of ethanol was added 0.8 g of sodium borohydride. Allowed to warm and stir for 1 h, then quenched with 20 mL of 10% citric acid and extracted into 3×25 mL of ether. The combined extracts were dried over magnesium sulfate and concentrated under reduced pressure. Drying under vacuum overnight gave 0.8 g of product as a colorless oil: 1H NMR (400 MHz, CDCl3) 7.3-7.1 (m, 5H), 3.4 (m, 1H), 3.05 (m, 2H), 2.9 (t, 1H), 2.8 (m, 1H), 2.6 (m, 1H), 2.2 (m, 4H), 1.8-1.5 (m, 5H), 1.42 (s, 9H).

Step 9: cis-1-[3-(2-Amino-ethyl)-cyclobutyl]-3-phenyl-propan-1-ol hydrochloride

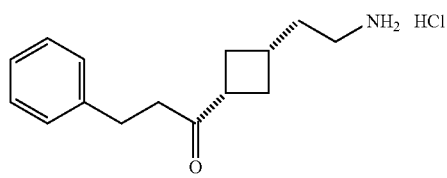

A mixture of 0.8 g of cis-{2-[3-(1-hydroxy-3-phenyl-propyl)-cyclobutyl]-ethyl}-carbamic acid tert-butyl ester and 25 mL of 4N HCl in dioxane was stirred at room temperature for 2 h, then concentrated to dryness and triturated with 50 mL of 5% ether in hexane and the solvents decanted. Drying under vacuum gave 0.8 g of the product as an amber resin: LCMS (m+1)=234.6.

Step 10: cis-3-Phenyl-1-{3-[2-(1H-pyrazolo[3,4-d]pyrimidine-4-ylamino)-ethyl]-cyclobutyl}-propan-1-ol

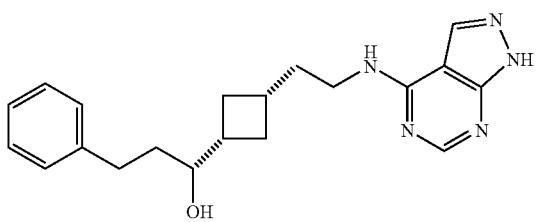

A mixture of 0.2 g of cis-1-[3-(2-amino-ethyl)-cyclobutyl]-3-phenyl-propan-1-ol hydrochloride, 0.12 g of 4-chloro-1H-pyrazolo[3,4-d]pyrimidine (R. K. Robins, J. Amer. Chem. Soc., 78, 784-790 (1956)), 10 mL of 2-propanol and 0.32 mL of N,N-diisopropyl-ethylamine was heated to 80° C. for 12 hours. The mixture was cooled and concentrated under reduced pressure and purified by preparative TLC eluting with 90:10 CHCl3: NH4OH: gave 0.15 g of product as a white solid. MS (m+1)=352.3; 1H NMR (400 MHz, CDCl3) 8.4 (s, 1H), 7.92 (s, 1H), 7.3-7.2 (m, 5H), 3.55 (m, 2H), 3.25 (s, 1H), 2.8 (m, 1H), 2.6 (m, 1H), 2.2 (m, 2H), 2.1 (ms, 1H), 1.6 (m, 12H). Resolution into the pure enantiomers could be performed by isocratic elution on Chiralcel OD at 1 mL/min, eluting with 80:5:5 hexane with 0.1% trifluoroacetic acid:2-propanol:methanol.

EXAMPLE 16 trans, trans-[4-(4-Phenyl-but-1-enyl)-cyclohexyl]-(1H-pyrazolo[3,4-d]pyrimidin-4-yl)-amine

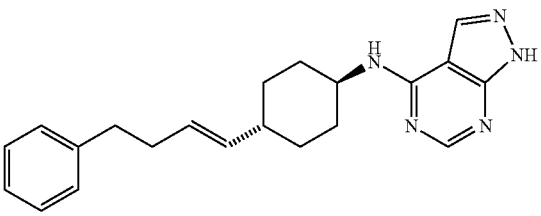

Step 1: trans, trans-[4-(4-Phenyl-but-1-enyl)-cyclohexyl]-carbamic acid tert-butyl ester

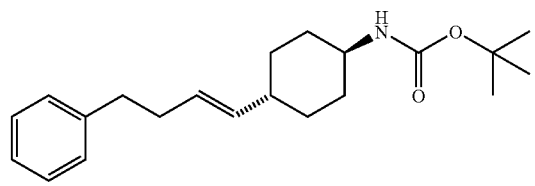

To a solution of 3-phenylpropyltriphenyl- phosphonium bromide (3.05 gm, 6.60 mmol) in THF (50 mL) at −78° C. and under nitrogen was added slowly n-butyl-lithium (2.5M in hexane, 2.40 mL, 6.00 mmol. The reaction was allowed to warm to 0° C., maintained at 0° C. for 1 hour, and cooled to −78° C. A solution of trans-tert-butyloxy-carbonyl-4-amino-cyclohexane-carboxaldehyde (Albany Molecular Research) (1.0 g) in THF (5 mL) was then added and the reaction allowed to room temperature and stir for 2 hours. The reaction was quenched with saturated aqueous ammonium chloride (50 mL) and extracted with ethyl acetate (2×50 ml). The organic extracts were dried over sodium sulfate, filtered, concentrated in vacuo and the resulting oil chromatographed on silica using 5-25% ethyl acetate/hexanes to give the desired product as a clear oil, 0.57 gm, (40%): $^1$H NMR 400 MHz ($\delta$, CDCL3) $\delta$: 7.30-7.24 (m, 2H); 7.20-7.14 (m, 3H); 5.32 (m, 1H); 5.17 (t, 1H); 4.38 (br s, 1H); 3.32 (br s, 1H); 2.65 (t, 2H); 2.32 (dd, 2H); 2.1-1.9 (m, 3); 1.3-1.0 (m, 6H); 1.42 (s, 9H).

Step 2: trans, trans-4-(4-Phenyl-but-1-enyl)cyclohexylamine

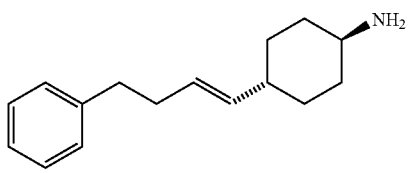

To a solution of 0.47 g of trans-[4-(4-phenyl-but-1-enyl)-cyclohexyl]-carbamic acid tert-butyl ester in 4 mL of dichloromethane at 0° C. and under nitrogen was added 2 mL of trifluoroacetic acid. The reaction was aged for 1 hour, concentrated under reduced pressure. The resulting oil dissolved in methylene chloride and concentrated to give an oil which was utilized in the next step without purification: LCMS (M+1)=230.

Step 3: trans, trans-[4-(4-Phenyl-but-1-enyl)-cyclohexyl]-(1H-pyrazolo[3,4-d]pyrimidin-4-yl)-amine

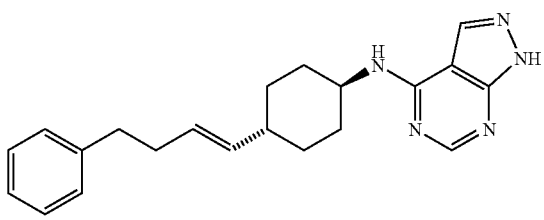

A mixture of 0.330 g of trans-4-(4-phenyl-but-1-enyl)-cyclohexyl-amine, 0.222 g of 4-chloro-1H-pyrazolo[3,4-d]pyrimidine (R. K. Robins, J. Amer. Chem. Soc., 78, 784-790 (1956)), 0.376 mL of di-isopropyl-ethylamine and 1.0 mL of dimethyl-formamide were combined and allowed to stir at room temperature for 18 h. The reaction was diluted with ethyl acetate (30 mL) and washed with saturated aqueous sodium bicarbonate. The ethyl acetate extract was dried over sodium sulfate, filtered, concentrated to an oil and chromatographed on silica using ethyl acetate to 5% methanol/ethyl acetate to give a crude product as a foam, (350 mg, 70%). Purification of the crude material (60 mg) using C-18 reversed phase chromatography (1% trifluroacetic acid in acetonitrile/water) gave 0.025 g of pure product as a foam: HRMS=348.2173.

EXAMPLE 17 trans-[4-(4-Phenyl-butyl)-cyclohexyl]-(1H-pyrazolo[3,4-d]pyrimidin-4-yl)-amine

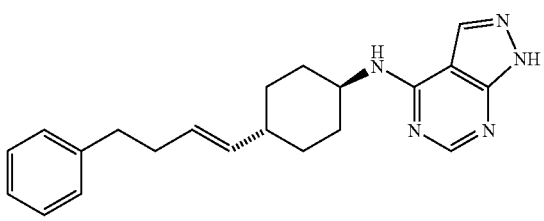

A mixture of 0.100 g of trans-[4-(4-phenyl-but-1-enyl)-cyclohexyl]-(1H-pyrazolo[3,4-d]pyrimidin-4-yl)-amine and 0.050 g of 10% palladium on carbon in 20 mL of ethanol was stirred under an atmosphere of hydrogen for 18 hours. The reaction was filtered to remove catalyst and concentrated under reduced pressure. Purification by C-18 reversed phase chromatography (0.1% trifluroacetic acid/water to 0.1% trifluoroacetic acid/acetonitrile) gave 0.200 g of pure product as a foam: HRMS=350.2324.

EXAMPLE 18

(R and S)-trans-4-Phenyl-1-[4-(1H-pyrazolo[3,4-d]pyrimidin-4-ylamino)-cyclohexyl]-butan-2-ol

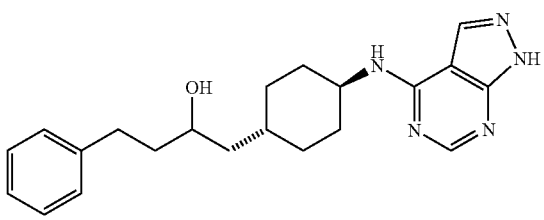

From commercial trans-tert-butyloxy-carbonyl-4-amino-cyclohexane-acetaldehyde (Albany Molecular Research) and excess phenethyl magnesium bromide, then in a manner similar to that described for Example 15, Steps 7-10: MS (m+1)= 366.1

EXAMPLE 19

(R and S)-cis-4-Phenyl-1-[4-(1H-pyrazolo[3,4-d]pyrimidin-4-ylamino)-cyclohexyl]-butan-2-ol

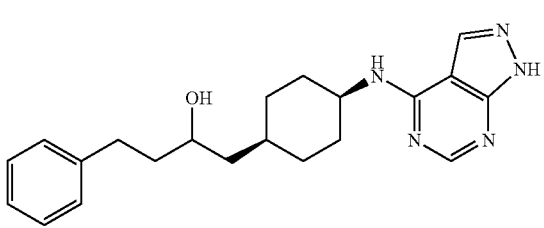

From commercial cis-tert-butyloxy-carbonyl-4-amino-cyclohexane-acetaldehyde (Albany Molecular Research) and excess phenethyl magnesium bromide, then in a manner similar to that described for Example 15, Steps 7-10: MS (m+1)=366.1

EXAMPLE 20 cis-(4-phenethyloxymethyl-cyclohexyl)-(1H-pyrazolo[3,4-d]pyrimidin-4-yl)-amine

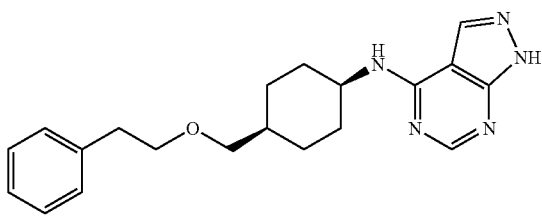

From trans-4-hydroxy-cyclohexanecarboxylic acid ethyl ester in a manner similar to that described for Example 15: MS (m+1)=352.1

EXAMPLE 21 trans-[3-Phenylpropyloxy)-cyclohexyl]-(1H-pyrazolo[3,4-d]pyrimidin-4-yl)-amine

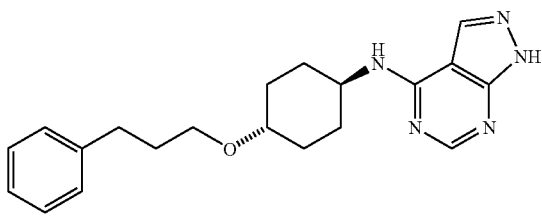

From trans-2-(4-(tert-butyl-dimethyl-silyloxy-cyclohexyl)-isoindole-1,3-dione and hydrocinnamaldehyde in a manner similar to that described for Example 1: MS (m+1)=352.1

EXAMPLE 22 cis-[3-Phenylpropyloxy)-cyclohexyl]-(1H-pyrazolo[3,4-d]pyrimidin-4-yl)-amine

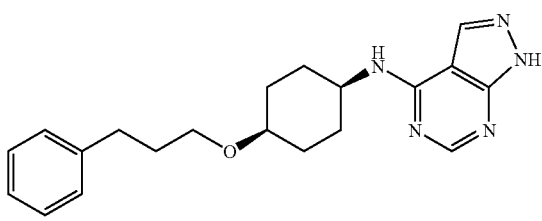

From cis-(4-tert-butyl-dimethyl-silanyloxy-cyclohexyl)-carbamic acid benzyl ester (prepared from cis (4-hydroxy-cyclohexyl)-carbamic acid tert-butyl ester, the product of Example 3, Step 3 by treatment with HCl in dioxane, protection with benzyl-chloroformate and tert-butyl-dimethyl-silyl chloride) and hydro-cinnamaldehyde in a manner similar to that described for Compounds 3-5: MS (m+1)=352.1

EXAMPLE 23 trans, trans-[4-(3-Phenyl-propenyl)-cyclohexyl]-(1H-pyrazolo[3,4-d]pyrimidin-4-yl)-amine

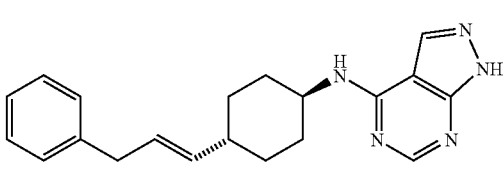

From trans-tert-butyloxy-carbonyl-4-amino-cyclohexane-carboxaldehyde (Albany Molecular Research) and 3-phenyl-ethyltriphenyl-phosphonium bromide in a manner similar to that described for Example 16: MS (m+1)=334.5

EXAMPLE 24 trans-[4-(3-Phenyl-propyl)-cyclohexyl]-(1H-pyrazolo[3,4-d]pyrimidin-4-yl)-amine

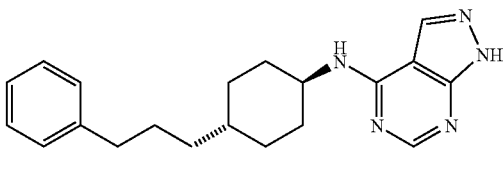

From trans, trans-[4-(3-phenyl-propenyl)-cyclohexyl]-(1H-pyrazolo[3,4-d]pyrimidin-4-yl)-amine (Example 24) in a manner similar to that described for Example 17: MS (m+1)=336.5

EXAMPLE 25

(R and S) trans-[4-(1-Methyl-2-phenyl-ethoxy)-cyclohexyl]-(1H-pyrazolo[3,4-d]pyrimidin-4-yl)-amine

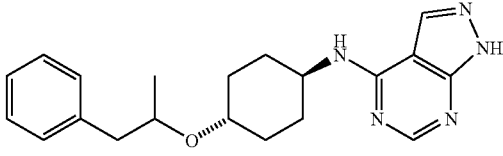

From trans-2-(4-(tert-butyl-dimethyl-silyloxy-cyclohexyl)-isoindole-1,3-dione and phenyl-acetone (P. L. Julian and J. J. Oliver, Organic Syntheses Coll. Vol. II, 391-393 (1943)) in the manner described for Example 1: MS (m+1)=352.2.

EXAMPLE 26

(R and S) {4-[2-(2-Fluoro-phenyl)-1-methyl-ethoxy]-cyclohexyl}-(1H-pyrazolo[3,4-d]pyrimidin-4-yl)-amine

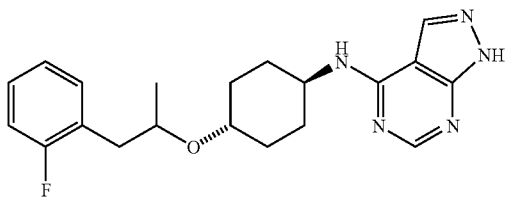

From trans-2-(4-(tert-butyl-dimethyl-silyloxy-cyclohexyl)-isoindole-1,3-dione and 2-fluorophenyl-acetone in the manner described for Example 1: MS (m+1)=370.1.

EXAMPLE 27

(R and S) {4-[2-(4-Fluoro-phenyl)-1-methyl-ethoxy]-cyclohexyl}-(1H-pyrazolo[3,4-d]pyrimidin-4-yl)-amine

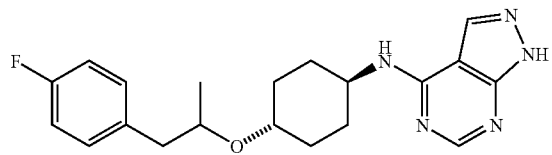

From trans-2-(4-(tert-butyl-dimethyl-silyloxy-cyclohexyl)-isoindole-1,3-dione and 4-fluorophenyl-acetone in the manner described for Example 1: MS (m+1)=370.1.

EXAMPLE 28

(R and S) [4-(1-Methyl-3-phenyl-propoxy)-cyclohexyl]-(1H-pyrazolo[3,4-d]pyrimidin-4-yl)-amine

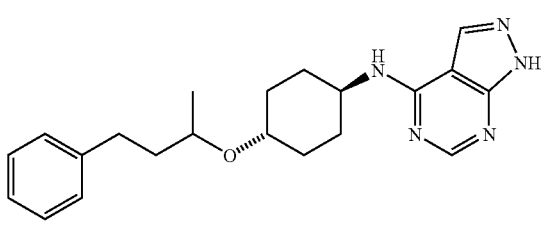

From trans-2-(4-(tert-butyl-dimethyl-silyloxy-cyclohexyl)-isoindole-1,3-dione and 4-phenyl-propan-2-one in the manner described for Example 1: MS (m+1)=366.1.

EXAMPLE 29

(R and S) [4-(2-Methyl-3-phenyl-propoxy)-cyclohexyl]-(1H-pyrazolo[3,4-d]pyrimidin-4-yl)-amine

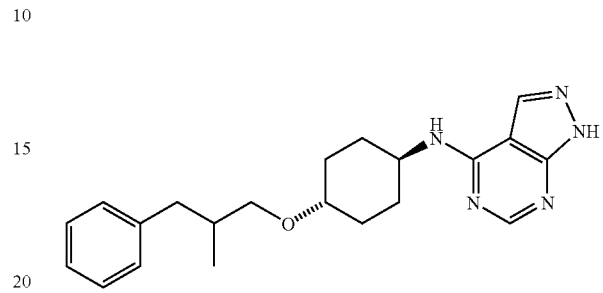

From trans-2-(4-(tert-butyl-dimethyl-silyloxy-cyclohexyl)-isoindole-1,3-dione and 2-methyl-3-phenylpropionaldehyde in the manner described for Example 1: MS (m+1)=366.1.

EXAMPLE 30

(R and S) trans-[4-(21-Methyl-2-phenyl-ethoxy)-cyclohexyl]-(1H-pyrazolo[3,4-d]pyrimidin-4-yl)-amine

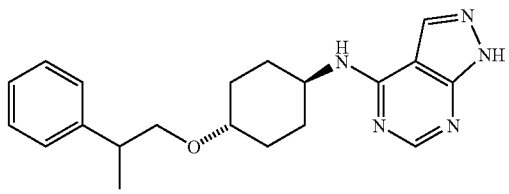

From trans-2-(4-(tert-butyl-dimethyl-silyloxy-cyclohexyl)-isoindole-1,3-dione and hydratropaldehyde in the manner described for Example 1: MS (m+1)=352.2.

EXAMPLE 31 trans-[4-(Indan-2-yloxy)-cyclohexyl]-(1H-pyrazolo[3,4-d]pyrimidin-4-yl)-amine

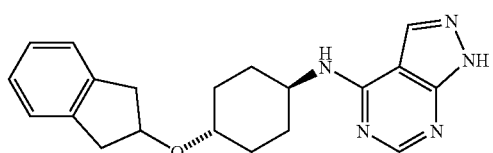

From trans-2-(4-(tert-butyl-dimethyl-silyloxy-cyclohexyl)-isoindole-1,3-dione and 2-indanone in the manner described for Example 1: MS (m+1)=350.1.

EXAMPLE 32 trans-{4-[2-(2-Trifluoromethylphenyl)ethoxy]cyclohexyl}-(1h-pyrazolo[3,4-d]pyrimidin-4-yl)amine (74)

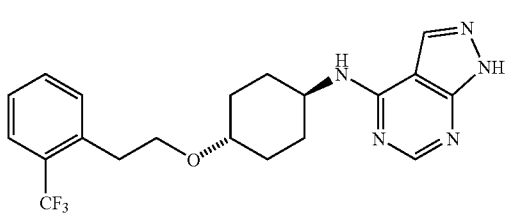

From trans-2-(4-(tert-butyl-dimethyl-silyloxy-cyclohexyl)-isoindole-1,3-dione and 2-indanone in the manner described for Example 1: MS (m+1)=406.4.

EXAMPLE 33 cis and trans [4-(4-Phenyl-cyclohexyloxy)-trans-cyclohexyl]-(1H-pyrazolo[3,4-d]pyrimidin-4-yl)-amine

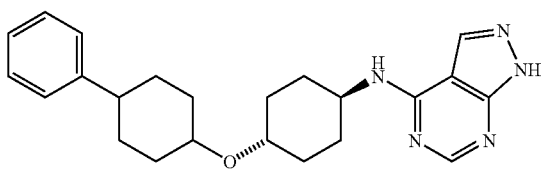

From trans-2-(4-(tert-butyl-dimethyl-silyloxy-cyclohexyl)-isoindole-1,3-dione and 4-phenyl acetone in the manner described for Example 1: MS (m+1)=392.2.

EXAMPLE 34

(R) [4-(2-Ethoxy-2-phenyl-ethoxy)-cyclohexyl]-(1h-pyrazolo[3,4-d]pyrimidin-4-yl)-amine

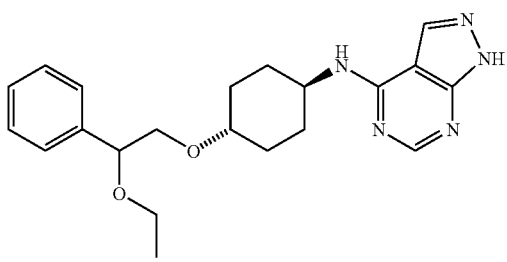

From trans-2-(4-(tert-butyl-dimethyl-silyloxy-cyclohexyl)-isoindole-1,3-dione and (R) O-ethyl mandelic acid ethyl ester in the manner described for Example 1: MS (m+1)= 382.3.

EXAMPLE 35

(S) [4-(2-Ethoxy-2-phenyl-ethoxy)-cyclohexyl]-(1h-pyrazolo[3,4-d]pyrimidin-4-yl)-amine

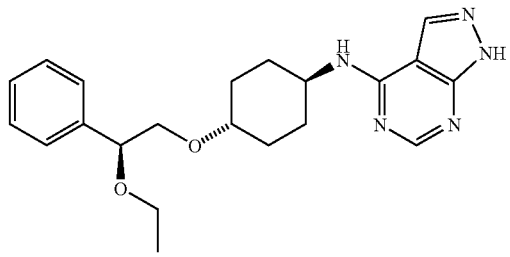

From trans-2-(4-(tert-butyl-dimethyl-silyloxy-cyclohexyl)-isoindole-1,3-dione and (S) O-ethyl mandelic acid ethyl ester in the manner described for Example 1: MS (m+1)=382.3.

EXAMPLE 36 trans-[2,2-Diphenyl-ethoxy)-cyclohexyl]-(1H-pyrazolo[3,4-d]pyrimidin-4-yl)-amine

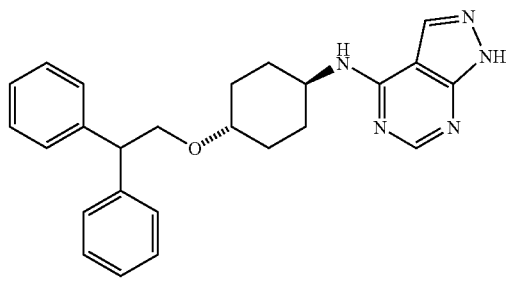

From trans-2-(4-(tert-butyl-dimethyl-silyloxy-cyclohexyl)-isoindole-1,3-dione and ethyl 2,2-diphenylacetate in the manner described for Example 1: MS (m+1)=414.4.

EXAMPLE 37 trans-[2-(2-Methoxy-phenyl)-ethoxy)-cyclohexyl]-(1H-pyrazolo[3,4-d]pyrimidin-4-yl)-amine

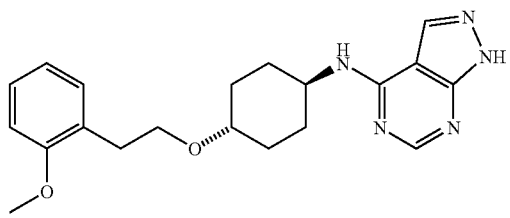

From trans-2-(4-(tert-butyl-dimethyl-silyloxy-cyclohexyl)-isoindole-1,3-dione and ethyl 2-methoxyphenylacetate in the manner described for Example 1: MS (m+1)=368.3.

EXAMPLE 38 trans-[2-Pentafluorophenyl-ethoxy)-cyclohexyl]-(1H-pyrazolo[3,4-d]pyrimidin-4-yl)-amine

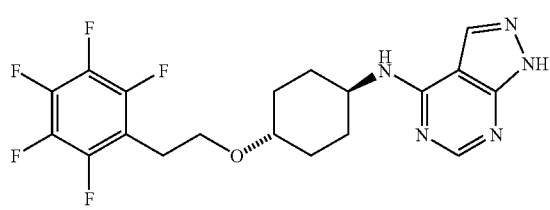

From trans-2-(4-(tert-butyl-dimethyl-silyloxy-cyclohexyl)-isoindole-1,3-dione and methyl 2,3,4,5,6-pentafluorophenylacetate in the manner described for Example 1: MS (m+1)=428.2.

EXAMPLE 39 trans-(4-Phenylmethyloxy-cyclohexyl)-(1h-pyrazolo[3,4-d]pyrimidin-4-yl)-amine

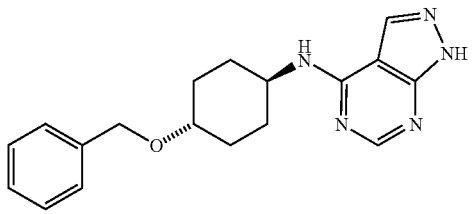

From trans-2-(4-(tert-butyl-dimethyl-silyloxy-cyclohexyl)-isoindole-1,3-dione and benzaldehyde in the manner described for Example 1: MS (m+1)=324.3.

EXAMPLE 40 trans-[4-(3-phenyl-1-hydroxy-propyl)-cyclohexyl]-(1H-pyrazolo[3,4-d]pyrimidin-4-yl)-amine

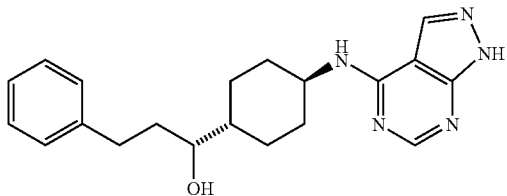

From trans-tert-butyloxy-carbonyl-4-amino-cyclohexane-carboxaldehyde (Albany Molecular Research) and phenethyl magnesium bromide in the manner described for Example 18: MS (m+1)=352.3.

EXAMPLE 41 trans-[4-(2-Phenoxy-ethoxy)-cyclohexyl]-(1H-pyrazolo[3,4-d]pyrimidin-4-yl)-amine

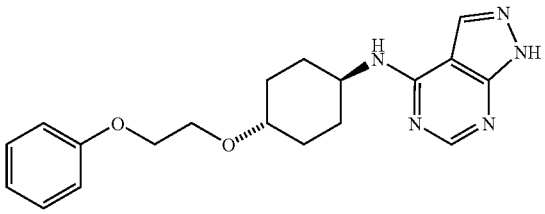

From trans-2-(4-(tert-butyl-dimethyl-silyloxy-cyclohexyl)-isoindole-1,3-dione (and ethyl phenoxyacetate in a manner similar to that described for Example 1: MS (m+1)=354.2.

EXAMPLE 42

(3R,1R and 3S,1S) (3-Phenylethyloxy-cyclopentyl)-(1H-pyrazolo[3,4-d]pyrimidin-4-yl)-amine

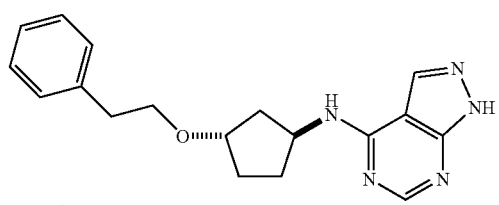

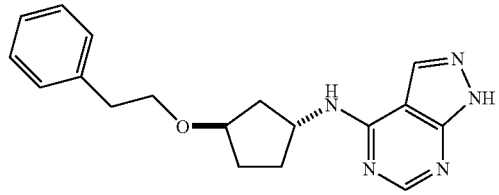

From racemic trans-3-aminocyclopentanol using the procedures described for Example 1: MS (m+1)=324.2.

EXAMPLE 43

(3S,1R and 3R,1S) (3-Phenylethyloxy-cyclopentyl)-(1H-pyrazolo[3,4-d]pyrimidin-4-yl)-amine

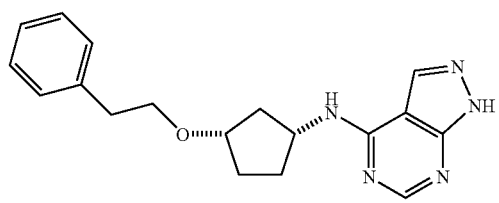

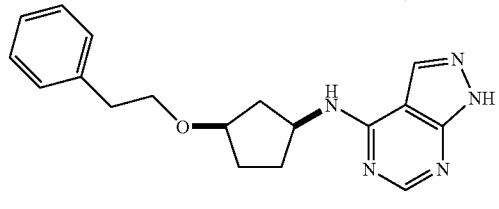

From racemic cis-3-aminocyclopentanol using the procedures described for Example 1: MS (m+1)=324.2.

EXAMPLE 44

(3R,1R, 2'R or 2'S and 3S,1S, 2'R or 2'S)-(3-(2'-Fluoro-2'-phenyl-ethoxy-cyclopentyl)-(1H-pyrazolo[3,4-d]pyrimidin-4-yl)-amine

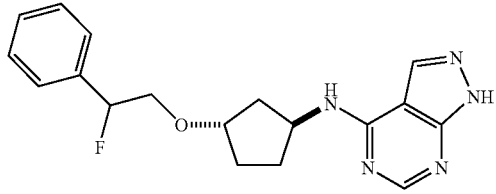

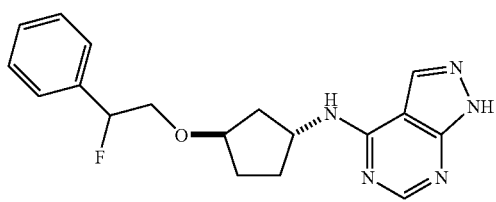

From racemic trans-3-aminocyclopentanol using the procedures described for Example 2: MS (m+1)=342.3.

EXAMPLE 45

(3R,1S, 2'R or 2'S and 3S,1R, 2'R or 2'S)-(3-(2'-Fluoro-2'-phenyl-ethoxy-cyclopentyl)-(1H-pyrazolo[3,4-d]pyrimidin-4-yl)-amine

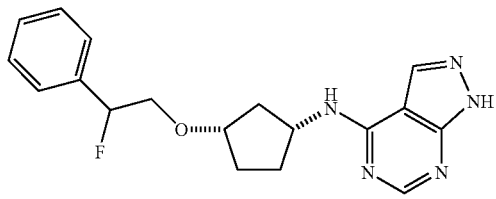

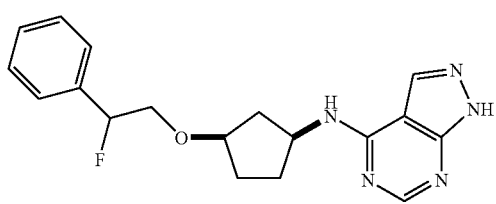

From racemic cis-3-aminocyclopentanol using the procedures described for Example 2: MS (m+1)=342.3.

EXAMPLE 46

(3R,1R and 3S,1S)-(3-(2',2'-difluoro-2'-phenyl-ethoxy-cyclopentyl)-(1H-pyrazolo[3,4-d]pyrimidin-4-yl)-amine

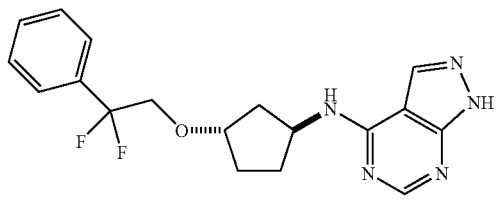

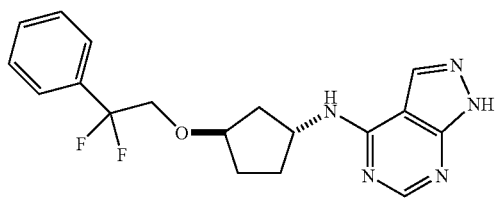

From racemic cis-3-aminocyclopentanol using the procedures described for Example 3: MS (m+1)=360.2.

EXAMPLE 47

(3R,1S and 3S,1R)-(3-(2',2'-difluoro-2'-phenyl-ethoxy-cyclopentyl)-(1H-pyrazolo[3,4-d]pyrimidin-4-yl)-amine (89)

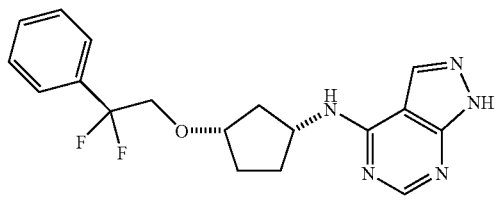

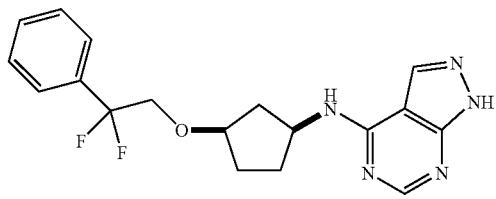

From racemic trans-3-aminocyclopentanol using the procedures described for Example 3: MS (m+1)=360.2.

EXAMPLE 48

(±)-3-Phenyl-1-{cis-4-[(1H-pyrazolo[3,4-d]pyrimi-din-4-ylamino)methyl]cyclohexyl}propan-1-ol

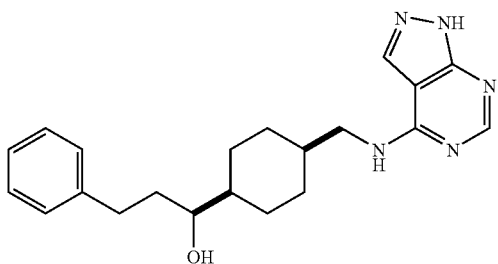

Step 1:
cis-4-(Butoxycarbonyl)cyclohexanecarboxylic acid

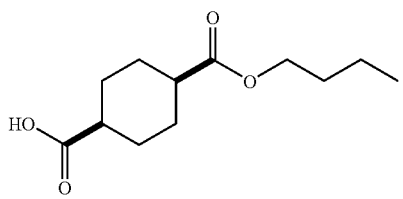

Step 1. (The procedure described for the trans isomer in *JCS Perkin I*, 1999, 25, 3023 was used.) A mixture of cis-cyclohexane-1,4-dicarboxylic acid (TCI) (24.1 g, 140 mmol), butyl formate (700 ml, 623 g, 6.10 mol, 43.5 equiv.), and Dowex 50W×2 resin (50-100 mesh, 140 g) in octane (700 ml) was stirred under nitrogen in a 110° C. oil bath for 24 hours. The mixture was cooled to ambient temperature. The supernatant solution was decanted away from the resin. The resin was washed with ethyl acetate: hexane (1:1, five 150 ml portions), and the washings were added to the supernatant. The solution was evaporated under reduced pressure, the resulting residue diluted with toluene (25 ml), evaporated under reduced pressure, and dried to give crude cis-4-(butoxycarbonyl)cyclohexanecarboxylic acid (36.5 g) as a yellow oil: $^1$H NMR (CDCl3) 4.08 (2H, m), 2.53 (1H, m), 2.46 (1H, m), 1.92 (4H, m), 1.70 (4H, m), 1.61 (2H, m), 1.38 (2H, m), 0.93 (3H, t, J 7 Hz).

Step 2: Butyl
cis-4-(hydroxymethyl)cyclohexanecarboxylate

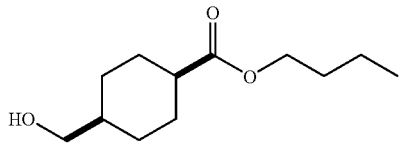

To a solution of crude cis-4-(butoxycarbonyl)cyclohexanecarboxylic acid (36.5 g) in dry tetrahydrofuran (300 ml) under nitrogen cooled in an ice-bath was added dropwise over 20 minutes 1.0M borane in tetrahydrofuran (150 ml, 150 mmol). The ice-bath was removed and the solution was stirred at ambient temperature for three hours. Water (200 ml) was added dropwise to the stirred solution, the mixture stirred an additional 15 minutes, and potassium carbonate (7.5 g) was added. The mixture was diluted with ether (500 ml) and the layers were separated. The organic layer was washed with brine (100 ml), dried (sodium sulfate), filtered, and the solvent was evaporated under reduced pressure to give crude product (32.38 g) as a pale yellow oil. The crude product was purified by flash column chromatography on silica gel, eluting with ethyl acetate/hexane (10:90 increasing to 50:50). The first compound to elute was dibutyl cis-cyclohexane-1,4-dicarboxylate (MS.: 285.3 (M+1), 3.92 g, 10%), followed by butyl cis-4-(hydroxymethyl)-cyclohexane carboxylate (23.97 g, 75%), as a pale yellow oil: $^1$H NMR (CDCl3) 4.08 (2H, t, J 7 Hz), 3.50 (1H, t, J 7 Hz), 2.56 (1H, m), 2.02 (2H, m), 1.52-1.65 (7H, m), 1.26-1.41 (5H, m), 0.94 (3H, t, J 7 Hz). MS.: 215.3 (M+1).

Step 3: Butyl cis-4-{[(methylsulfonyl)oxy]-methyl}-cyclohexane carboxylate

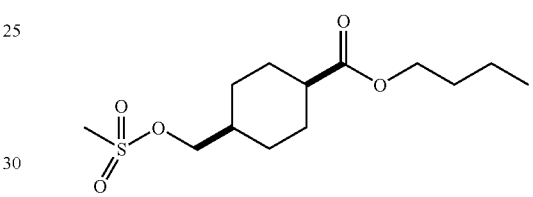

To a solution of butyl cis-4-(hydroxymethyl)cyclohexanecarboxylate (25.06 g, 117 mmol) and triethylamine (24.3 ml, 17.8 g, 176 mmol) in methylene chloride (600 ml) under nitrogen, cooled in an ice-bath, was added dropwise over 20 minutes methane-sulfonyl-chloride (13.6 ml, 16.1 g, 140 mmol). The solution was stirred 18 hours while warming from 0° C. to ambient temperature. Additional triethylamine (2 ml, 1.5 g, 14 mmol) and methane-sulfonyl-chloride (1 ml, 1.5 g, 13 mmol) were added and the mixture was stirred four hours at ambient temperature. The mixture was diluted with methylene chloride (300 ml), washed with 1N hydrochloric acid (300 ml), water (300 ml), and half-saturated sodium carbonate solution (300 ml), dried (sodium sulfate), filtered, and the solvent was evaporated under reduced pressure to give crude butyl cis-4-{[(methylsulfonyl)oxy] methyl}cyclohexanecarboxylate (35.31 g) as an orange oil: $^1$H NMR (CDCl3) 4.08 (4H, m), 3.00 (3H, s), 2.59 (1H, m), 2.05 (2H, m), 1.86 (1H, m) 1.52-1.69 (6H, m), 1.31-1.43 (4H, m), 0.94 (3H, m). MS.: 293.3 (M+1).

Step 4: Butyl
cis-4-(azidomethyl)cyclohexanecarboxylate

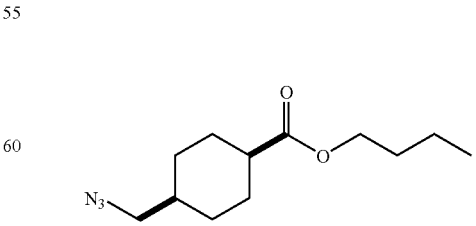

To a solution of crude butyl cis-4-{[(methylsulfonyl)oxy] methyl}-cyclohexane carboxylate (35.3 g, 117 mmol) in dimethylformamide (146 ml) was added sodium azide (30.4 g, 468 mmol, 4 equiv.). The mixture was stirred under nitrogen at 80° C. for eight hours. Approximately one-half of the dimethylformamide was distilled off (80° C. oil bath, 3.5 mm). The residue was diluted with water (750 ml) and extracted with ether (3×250 ml). The combined extract was washed with water (2×100 ml) and brine (100 ml), dried (sodium sulfate), filtered, and the solvent was evaporated under reduced pressure to give crude butyl cis-4-(azidomethyl)cyclohexanecarboxylate (26.80 g, 98%) as a yellow oil.

$^1$H NMR (CDCl3) 4.09 (2H, t, J 7 Hz), 3.17 (2H, d, J 7 Hz), 2.57 (1H, m), 2.02 (2H, m), 1.66-1.52 (7H, m), 1.41-1.26 (4H, m), 0.94 (3H, t, J 7 Hz). MS=240 (M+1).

Step 5: Butyl cis-4-(aminomethyl)cyclohexanecarboxylate

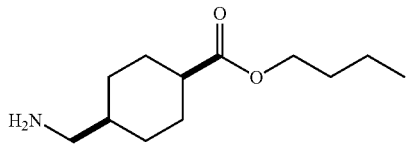

A mixture of butyl cis-4-(azidomethyl)cyclohexanecarboxylate (27.85 g, 116 mmol), 6N hydrochloric acid (39 ml, 234 mmol) and 10% palladium on carbon (3.78 g) in ethanol (500 ml) was hydrogenated (hydrogen balloon) for 2.5 days. The catalyst was removed by filtration through Celite. The filter cake was washed with ethanol (3×50 ml) and the filtrate was concentrated under reduced pressure to give a gum. The gum was taken up in water (250 ml) and washed with ether (250 ml). The aqueous layer was basified to pH 10 with 10N sodium hydroxide solution and extracted with ethyl acetate (3×250 ml). The ethyl acetate layer was washed with water (100 ml) and brine (100 ml), dried (sodium sulfate), filtered, and the solvent was evaporated under reduced pressure to give butyl cis-4-(aminomethyl)cyclohexanecarboxylate (15.25 g, 62%) as a gum: $^1$H NMR (CDCl3) 4.08 (2H, t, J 7 Hz), 2.57 (2H, d, J 8 Hz), 2.02 (2H, m), 1.66-1.51 (6H, m), 1.45-1.23 (5H, m), 0.94 (3H, t, J 7 Hz). MS: 214.2 (M+1).

Step 6: Butyl cis-4-{[(tert-butoxycarbonyl)amino]-methyl}-cyclohexane carboxylate

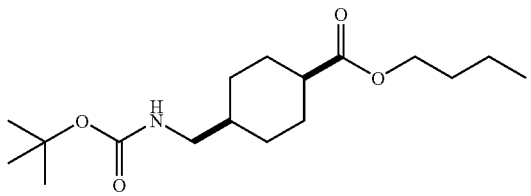

To a solution of butyl cis-4-(aminomethyl)cyclohexanecarboxylate (15.32 g, 71.8 mmol) in dichloromethane (600 ml) under an atmosphere of nitrogen was added dropwise over 20 minutes a solution of di-tert-butyl dicarbonate (17.2 ml. 16.4 g, 75.0 mmol) in dichloromethane (50 ml). The solution was stirred 18 hours at ambient temperature. The solution was diluted with dichloromethane (200 ml), washed with saturated sodium bicarbonate solution (200 ml), water (200 ml), and brine (200 ml), dried (sodium sulfate), filtered, and the solvent evaporated under reduced pressure to give crude product (26.0 g, theoretical yield 22.5 g) as a yellow oil. Mass spec.: 314.3 (M+1).

Step 7: cis-4-{[(tert-butoxycarbonyl)amino]-methyl}cyclohexane carboxylic acid

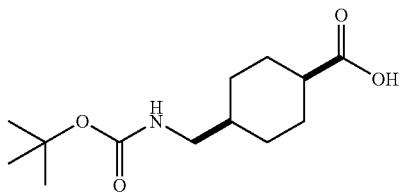

To a solution of crude butyl cis-4-{[(tert-butoxycarbonyl)amino]methyl}cyclohexanecarboxylate (28.4 g, approximately 79.3 mmol) in methanol (200 ml) was added dropwise over five minutes 2N sodium hydroxide solution (400 mmol). The mixture was stirred 18 hours at ambient temperature under nitrogen. The mixture was concentrated under reduced pressure to remove methanol. To the aqueous residue was added methyl orange (1 mg) and 3N hydrochloric acid was added to adjust the mixture to pH 4. The mixture was extracted with ethyl acetate (3×200 ml). The extract was washed with water (100 ml), and brine (100 ml), dried (sodium sulfate), filtered, and the solvent evaporated under reduced pressure to give cis-4-{[(tert-butoxycarbonyl)amino]methyl}cyclohexanecarboxylic acid (18.76 g, 92%) as an off-white solid. MS: 258.3 (M+1).

Step 8: tert-Butyl [(cis-4-{[methoxy(methyl)amino]-carbonyl}-cyclohexyl)-methyl]carbamate

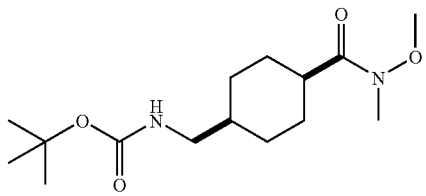

To a solution of cis-4-{[(tert-butoxycarbonyl)amino]methyl}-cyclohexanecarboxylic acid (18.53 g, 72.0 mmol) and N-methylpiperidine (21.9 ml, 17.8 g, 180 mmol) in methylene chloride (360 ml) under nitrogen cooled in an ice-bath was adde dropwise methyl chloroformate (6.13 ml, 7.48 g, 79.2 mmol). The solution was stirred 15 minutes with cooling, and O,N-dimethylhydroxylamine hydrochloride (8.43 g, 86.4 mmol) was added. The mixture was stirred 18 hours while warming from ice-bath temperature to ambient temperature. The mixture was washed with 10% citric acid solution (100 ml), saturated sodium carbonate solution (100 ml), water (100 ml), and brine (100 ml), dried (sodium sulfate), filtered, and the solvent evaporated under reduced pressure to give crude product (15.30 g, 71%) as a yellow oil. The crude product was purified by flash column chromatography on silica gel, eluting with a gradient of 50:50 to 75:25 ethyl acetate/hexane to give tert-butyl [(cis-4-{[methoxy(methyl) amino]carbonyl}cyclohexyl)methyl]carbamate (13.76 g, 64%) as a pale yellow oil. $^1$H NMR (CDCl3) 4.61 (1H, br s), 3.68 (3H, s), 3.17 (3H, s), 3.11 (2H, t, J 6.5 Hz), 2.79 (1H, m), 1.75 (3H, m), 1.68-1.52 (6H, m), 1.44 (9H, s).

Step 9: tert-Butyl {[cis-4-(3-phenylpropanoyl)cyclohexyl]-methyl}carbamate

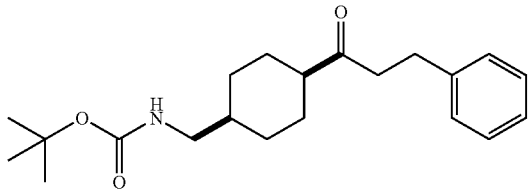

To a solution of tert-butyl [(cis-4-{[methoxy(methyl) amino]carbonyl}cyclohexyl)methyl]carbamate (4.51 g, 15.0 mmol) in dry tetrahydrofuran (15 ml) under nitrogen cooled in an ice-bath was added dropwise via syringe over five minutes a 1M solution of phenethyl magnesium bromide in tetrahydrofuran (60 ml, 60 mmol, 4 equivalents). The mixture was stirred 18 hours while warming from ice-bath temperature to ambient temperature. The reaction was quenched by addition of saturated ammonium chloride solution (60 ml). The mixture was diluted with ethyl acetate (240 ml) and the layers were separated. The organic layer was washed with water (60 ml), and brine (60 ml), dried (sodium sulfate), filtered, and the solvent evaporated under reduced pressure to give crude product (6.30 g) as a yellow oil. The crude product was purified by flash column chromatography on silica gel, eluting with ethyl acetate/hexane (16:84 increasing to 25:75) to give tert-butyl {[cis-4-(3-phenylpropanoyl)cyclohexyl] methyl}carbamate (3.50 g, 68%) as a white solid: $^1$H NMR (CDCl3) 7.27 (2H, m), 7.18 (3H, m), 4.55 (1H, br s), 2.99 (2H, t, J 6.5 Hz), 2.88 (2H, t, J 7.5 Hz), 2.75 (2H, t, J 7.5 Hz), 2.44 (1H, m), 1.88 (2H, m), 1.53 (4H, m), 1.43 (9H, s), 1.26 (3H, t, J 7 Hz): MS: 346.3 (M+1).

Step 10: (±)-tert-Butyl {[cis-4-(1-hydroxy-3-phenylpropyl)cyclohexyl]methyl}carbamate

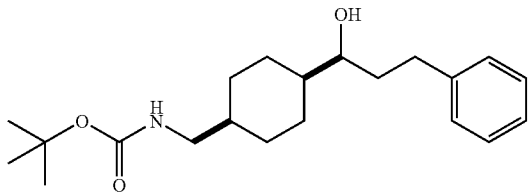

To a solution of tert-butyl {[cis-4-(3-phenylpropanoyl)cyclohexyl]-methyl]carbamate (3.45 g, 10.0 mmol) in ethanol (65 ml) under nitrogen cooled in an ice-bath was added sodium borohydride (0.78 g, 21 mmol). The mixture was stirred two hours at ice-bath temperature. The reaction was quenched by addition saturated sodium bicarbonate solution (30 ml). The mixture was concentrated under reduced pressure to remove ethanol. The aqueous residue was diluted with water (15 ml) and extracted with ethyl acetate (3×60 ml). The extract was washed with water (20 ml), and brine (20 ml), dried (sodium sulfate), filtered, and the solvent evaporated under reduced pressure to give crude (±)-tert-butyl {[cis-4-(1-hydroxy-3-phenylpropyl)cyclohexyl]methyl)carbamate (3.64 g, theoretical yield 3.48 g) as a colorless gum. MS: 348.3 (M+1).

Step 11: (±)-1-[cis-4-(Aminomethyl)cyclohexyl]-3-phenylpropan-1-ol

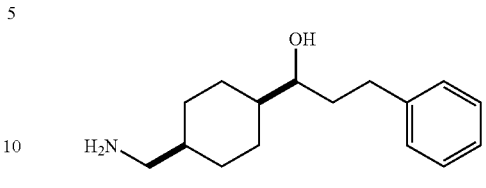

To a solution of (±)-tert-butyl {[cis-4-(1-hydroxy-3-phenylpropyl)cyclohexyl]methyl}carbamate (3.63 g, approximately 10 mmol) in dioxane (20 ml) cooled in an ice-bath was added dropwise 4M hydrogen choride in dioxane (20 ml, 80 mmol). The solution was stirred 2 hours at ice-bath temperature, one hour at ambient temperature, then concentrated at reduced pressure. The solid residue was taken up in methylene chloride (200 ml) and 10N sodium hydroxide (1.0 ml, 10 mmol) was added. The mixture was stirred 20 minutes at ambient temperature, dried (sodium carbonate and sodium sulfate), filtered, and the solvent evaporated under reduced pressure to give crude (+−)-1-[cis-4-(aminomethyl)cyclohexyl]-3-phenylpropan-1-ol (2.71 g, theoretical yield 2.47 g) as a yellow gum: $^1$H NMR (CDCl3) 7.28 (2H, m), 7.18 (3H, m), 3.51 (1H, m), 2.85 (1H, m), 2.64 (3H, m), 1.88 (1H, m), 1.69 (1H, m), 1.54-1.33 (3H, m). MS: 248.3 (M+1).

Step 12: (±)-3-Phenyl-1-{cis-4-[(1H-pyrazolo[3,4-d]pyrimidin-4-ylamino)methyl]cyclohexyl}propan-1-ol

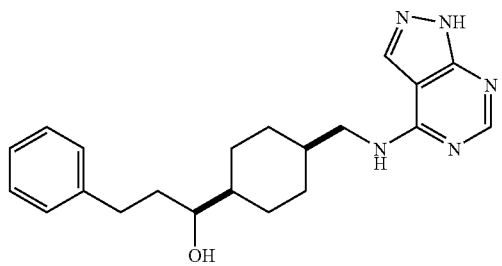

A solution of (±)-1-[cis-4-(aminomethyl)cyclohexyl]-3-phenylpropan-1-ol (124 mg, 0.50 mmol), 4-chloro-1H-pyrazolo[3,4-d]pyrimidine (116 mg, 0.75 mmol), and diisopropylethylamine (0.175 ml, 1.0 mmol) in 2-butanol (5 ml) was stirred at reflux for 18 hours. The mixture was concentrated under reduced pressure and the residue was taken up in ethyl acetate (25 ml). The mixture was washed with saturated sodium bicarbonate solution (10 ml), water (10 ml), and brine (10 ml), dried (sodium sulfate), filtered, and the solvent was evaporated under reduced pressure to give crude product (183 mg) as a yellow gum. The crude product was chromatographed on a 2 mm silica gel prep plate eluting with methanol: methylene chloride:ammonium hydroxide (10:90:1) to give a yellow foam (129 mg) The foam was crystallized from ethyl acetate, the precipitate filtered off and dried in vacuo to give (±)-3-Phenyl-1-{cis-4-[(1H-pyrazolo[3,4-d]pyrimidin-4-ylamino)methyl]-cyclohexyl}-propan-1-ol (123 mg, 67%) as a yellow solid.

$^1$H NMR (CDCl3) 11.5 (1H, br s), 8.40 (1H, s), 7.96 (1H, s), 7.29 (2H, m), 7.19 (3H, m), 5.3 (1H, br s), 3.63 (2H, br s), 3.54 (1H, m), 2.86 (1H, m), 2.69 (1H, m), 2.02 (1H, m), 1.89 (1H, m), 1.76-1.49 (11H, m). MS: 366.3 (M+1).

EXAMPLE 49

S-(−)-3-Phenyl-1-{cis-4-[(1H-pyrazolo[3,4-d]pyrimidin-4-ylamino)methyl]cyclohexyl}propan-1-ol

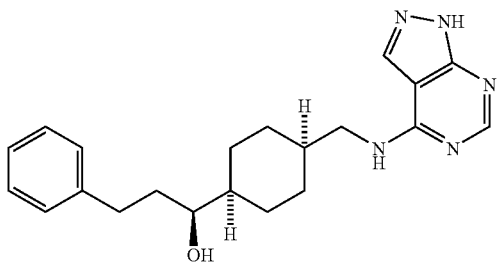

EXAMPLE 50

R-(+)-3-Phenyl-1-{cis-4-[(1H-pyrazolo[3,4-d]pyrimidin-4-ylamino)methyl]cyclohexyl}propan-1-ol

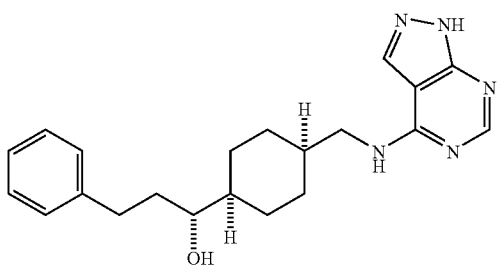

Racemic (±)-3-phenyl-1-{cis-4-[(1H-pyrazolo[3,4-d]pyrimidin-4-ylamino)methyl]cyclohexyl}propan-1-ol was resolved by preparative chiral HPLC (Chiralpak AD column, 5×50 mm, hexane: isopropanol: diethylamine (80:20:0.1 to 60:40:0.1 stepwise over 55 min.), 80 ml/min at 210 nm, rt(−) 46.1 min, rt(+) 53.7 min). The first enantiomer to elute was S-(−)-3-phenyl-1-{cis-4-[(1H-pyrazolo[3,4-d]pyrimidin-4-ylamino)methyl]cyclohexyl}propan-1-ol (36 mg) as an off-white solid, after crystallization from ethyl acetate: MS=366.3 (M+1).

$[\alpha]_D$=−20° (c=0.246, methanol). The second enantiomer to elute was R-(+)-3-phenyl-1-{cis-4-[(1H-pyrazolo[3,4-d]pyrimidin-4-ylamino)methyl]cyclohexyl}propan-1-ol (37 mg) as a pale yellow solid, after crystallization from ethyl acetate. MS=366.3 (M+1). $[\alpha]_D$=+19° (c=0.233, methanol).

EXAMPLE 51

(±)-1-{4-cis-[(6-Methyl-1H-pyrazolo[3,4-d]pyrimidin-4-ylamino)methyl]cyclohexyl}-3-phenylpropan-1-ol

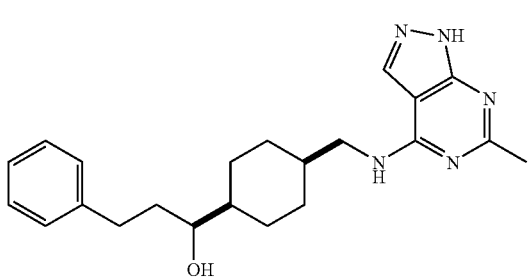

Employing the procedure substantially as described in Example 49 above but substituting 4-chloro-6-methyl-1H-pyrazolo[3,4-d]pyrimidine hydrochloride for 4-chloro-1H-pyrazolo[3,4-d]pyrimidine, the product (±)-1-{4-cis-[(6-methyl-1H-pyrazolo[3,4-d]pyrimidin-4-ylamino)methyl]cyclohexyl}-3-phenylpropan-1-ol (103 mg, 54%) was obtained as a pale yellow solid. $^1$H NMR (CDCl3) 11.6 (1H, br s), 7.91 (1H, s), 7.29 (2H, m), 7.19 (3H, m), 5.7 (1H, br s), 3.62 (2H, br s), 3.54 (1H, m), 2.86 (1H, m), 2.68 (1H, m), 2.59 (3H, s), 1.99 (1H, m), 1.89 (1H, m), 1.76-1.49 (11H, m). MS: 380.3 (M+1).

EXAMPLE 52

(±)-4-Phenyl-1-trans-[4-(1H-pyrazolo[3,4-d]pyrimidin-4-ylamino)cyclohexyl]butan-1-ol

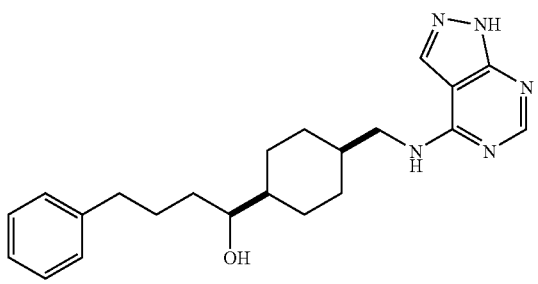

Step 1:
cis-(Tetrahydropyran-2-yloxy)cyclohexanecarboxylic acid tetrahydropyran-2-yl ester

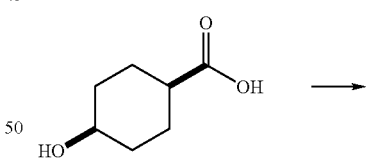

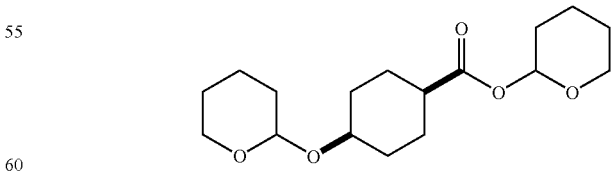

To a mixture of cis-4-hydroxycyclohexane carboxylic acid (2.88 g, 20.0 mmol) and 3,4-dihydro-2H-pyran (5.49 ml, 5.05 g, 60.0 mmol) in methylene chloride (100 ml) was added pyridinium p-toluenesulfonate (0.50 g, 2.0 mmol). The mixture was stirred 2.5 days at ambient temperature under nitrogen. The mixture was diluted with ether (300 ml), filtered, and the solvent was evaporated under reduced pressure to give crude product (6.68 g) as a yellow oil. The crude product was purified by flash column chromatography on silica gel, eluting with a gradient of 10:90 to 50:50 ethyl acetate/hexane to give 4-cis-(tetrahydropyran-2-yloxy)cyclohexanecarboxylic acid tetrahydropyran-2-yl ester (5.35 g, 86%) as a colorless oil: MS=313.1 (M+1).

Step 2: [4-cis-(Tetrahydropyran-2-yloxy)cyclohexyl]-methanol

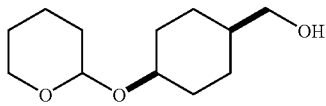

To a 1M solution of lithium aluminum hydride in tetrahydrofuran (19 ml, 19 mmol) under nitrogen was added dropwise over 10 minutes a solution of 4-cis-(tetrahydropyran-2-yloxy)cyclohexanecarboxylic acid tetrahydropyran-2-yl ester (5.94 g, 19.0 ml) in tetrahydrofuran. The mixture was stirred 30 minutes at ambient temperature. The reaction was quenched by careful dropwise addition of water (19 ml), followed by dropwise addition of 3N sodium hydroxide solution, and water (52 ml). The inorganic solids were remove by filtration and washed with tetrahydrofuran (20 ml) then with ether (50 ml). The layers of the filtrate were separated and the aqueous layer was extracted with ethyl acetate (3×200 ml). The combined organic layer was washed with water (50 ml), and brine (50 ml), dried (sodium sulfate), filtered, and the solvent evaporated under reduced pressure to give crude product (4.90 g) as a colorless oil. The crude product was filtered through a pad of silica gel eluting with ethyl acetate:hexane (50:50) to give [4-cis-(tetrahydropyran-2-yloxy)cyclohexyl]methanol (4.06 g, 100%) as a colorless oil: ¹H NMR (CDCl3) 4.66 (1H, m), 3.90 (2H, m), 3.50 (3H, m), 1.84 (3H, m), 1.70 (1H, m), 1.56-1.35 (12H, m).

Step 3: cis-4-(Tetrahydro-2H-pyran-2-yloxy)-cyclohexane carboxaldehyde

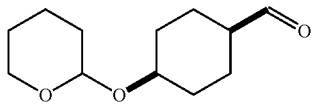

To a stirred mixture of pyridinium chlorochromate (6.60 g, 30.6 mmol) and powdered 4A molecular sieves (8.5 g) in methylene chloride (75 ml) cooled in an ambient temperature water bath was added dropwise a solution of [4-cis-(tetrahydropyran-2-yloxy)cyclohexyl]methanol (3.64 g, 17.0 mmol) in methylene chloride. The mixture was stirred 45 minutes at ambient temperature. Ether (600 ml) was added and the supernatant was decanted from a solid residue. The residue was washed with ether (3×100 ml). The combined supernatant was filtered through a short column of silica gel and the column was washed with ether. The filtrate was evaporated under reduced pressure to give crude cis-4-(tetrahydro-2H-pyran-2-yloxy)cyclohexanecarboxaldehyde (3.27 g, 91%) as a yellow oil: ¹H NMR (CDCl3) 9.64 (1H, s), 4.68 (1H, m), 3.85 (2H, m), 3.49 (1H, m), 2.27 (1H, m), 1.99-1.52 (14H, m).

Step 4: (±)-4-Phenyl-1-[4-cis-(tetrahydropyran-2-yloxy)cyclohexyl]butan-1-ol

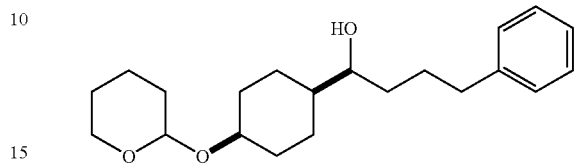

To a solution of cis-4-(tetrahydro-2H-pyran-2-yloxy)cyclohexanecarboxaldehyde (1.06 g, 5.0 mmol) in dry tetrahydrofuran (5 ml) under nitrogen cooled in an ice-bath was added dropwise via syringe over five minutes a 05M solution of phenylpropyl magnesium bromide in tetrahydrofuran (12 ml, 6 mmol). The mixture was stirred 2 hours at ice-bath temperature. The reaction was quenched by addition of saturated ammonium chloride solution (25 ml). The mixture was diluted with ethyl acetate (100 ml) and the layers were separated. The organic layer was washed with water (25 ml), and brine (25 ml), dried (sodium sulfate), filtered, and the solvent evaporated under reduced pressure to give crude product (1.56 g) as a yellow oil. The crude product was purified by flash column chromatography on silica gel, eluting with ethyl acetate/hexane (5:95 increasing to 50:50) to give (+−)-4-phenyl-1-[4-cis-(tetrahydropyran-2-yloxy)cyclohexyl]butan-1-ol 0.87 g, 52%) as a colorless oil: ¹H NMR (CDCl3 7.27 (2H, m), 7.19 (3H, m), 4.65δ) (1H, m), 3.90 (2H, m), 3.48 (2H, m), 2.63 (2H, m), 1.91 (4H, m), 1.69 (2H, m), 1.65-1.31 (14H, m).

Step 5: (±)-Acetic acid 4-phenyl-1-[4-cis-(tetrahydropyran-2-yloxy)cyclohexyl]-butyl ester

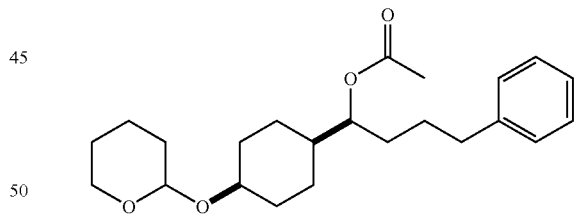

To a solution of (±)-4-phenyl-1-[4-cis-(tetrahydropyran-2-yloxy)cyclohexyl]butan-1-ol (0.83 g, 2.5 mmol), triethylamine (0.42 ml, 0.30 g, 3.0 mmol) and 4-dimethylaminopyridine (10 mg) in methylene chloride (15 ml) under nitrogen cooled in an ice-bath was added acetic anhydride (0.28 ml, 0.31 g, 3.0 mmol). The solution was stirred four hours at ice-bath temperature. The solution was diluted with methylene chloride (50 ml), washed with saturated sodium bicarbonate solution (20 ml), water (20 ml), and brine (20 ml), dried (sodium sulfate), filtered, and the solvent was evaporated under reduced pressure to give crude product (0.955 g) as a colorless oil. The crude product was purified by flash column chromatography on silica gel, eluting with ethyl acetate/hexane (10:90 increasing to 50:50) to give (±)-acetic acid 4-phenyl-1-[4-cis-(tetrahydropyran-2-yloxy)cyclohexyl]butyl ester (0.765 g, 82%) as a colorless oil: $^1$H NMR (CDCl3) 7.27 (2H, m), 7.17 (3H, m), 4.83 (1H, s), 4.64 (1H, m), 3.88 (2H, m), 3.48 (1H, m), 2.61 (2H, m), 2.05 (3H, s), 1.88 (3H, m), 1.71-1.30 (16H, m).

Step 6: (±)-Acetic acid
1-(4-cis-hydroxycyclohexyl)-4-phenylbutyl ester

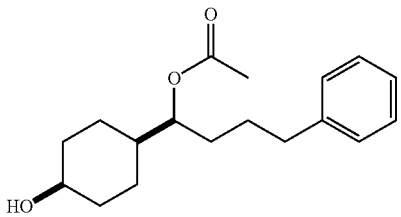

To a solution of (±)-acetic acid 4-phenyl-1-[4-cis-(tetrahydropyran-2-yloxy)cyclohexyl]butyl ester (0.712 g, 1.90 mmol) in ethanol (15 ml) was added pyridinium p-toluenesulfonate (0.050g, 0.20 mmol) and the mixture was stirred under nitrogen at 55° C. for four hours. The mixture was concentrated under reduced pressure and the residue was purified by flash column chromatography on silica gel, eluting with ethyl acetate/hexane (10:90 increasing to 75:25) to give (±)-acetic acid 1-(4-cis-hydroxycyclohexyl)-4-phenyl-butyl ester (0.40 g, 72%) as a colorless oil: $^1$H NMR (CDCl3) s7.27 (2H, m), 7.18 (3H, m), 4.84 (1H, d, J 4 Hz), 4.01 (1H, s), 2.61 (2H, m), 2.05 (3H, s), 1.76 (2H, m), 1.66-1.47 (11H, m), 1.21 (1H, m).

Step 7: (±)-Acetic acid 1-(4-cis-methanesulfonyloxy-cyclohexyl)-4-phenylbutyl ester

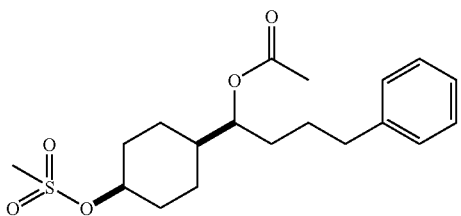

To a solution of (±)-acetic acid 1-(4-cis-hydroxycyclohexyl)-4-phenylbutyl ester (0.363 g, 1.25 mmol) in pyridine (3 ml) under nitrogen was added methanesulfonyl chloride (0.118 ml, 0.175 g, 1.52 mmol). The mixture was stirred 3 hours at ambient temperature. The solvent was removed under reduced pressure. The residue was partitioned between ethyl acetate (30 ml) and 1N sodium hydroxide solution (10 ml) and the layers were separated. The organic layer was washed with water (10 ml), and brine (10 ml), dried (sodium sulfate), filtered, and the solvent evaporated under reduced pressure to give crude product (0.447 g) as a colorless oil. The crude product was filtered through a pad of silica gel eluting with ethyl acetate: hexane (33:67) to give (±)-acetic acid 1-(4-cis-methanesulfonyloxycyclohexyl)-4-phenylbutyl ester (0.447 g, 97%) as a colorless oil: $^1$H NMR (CDCl3) 7.27 (2H, m), 7.17 (3H, m), 4.97 (1H, s), 4.83 (1H, m), 3.00 (3H, s), 2.61 (2H, m), 2.10 (2H, m), 2.05 (3H, s), 1.67-1.53 (9H, m), 1.45 (2H, m).

Step 8: (±)-Acetic acid
1-(4-trans-azidocyclohexyl)-4-phenylbutyl ester

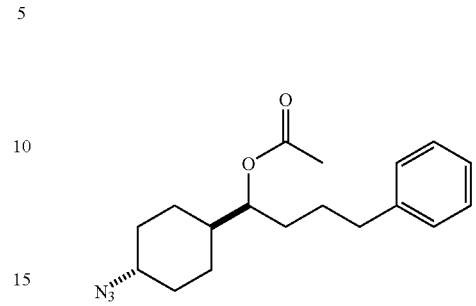

To a solution of (±)-acetic acid 1-(4-cis-methanesulfonyloxycyclohexyl)-4-phenylbutyl ester (405 mg, 1.1 mmol) in dimethylformamide (1.5 ml) was added sodium azide (215 mg, 3.3 mmol). The mixture was stirred under nitrogen at 80° C. for two hours. The mixture was diluted with water (15 ml) and extracted with ether (3×25 ml). The extract was washed with water (15 ml), and brine (15 ml), dried (sodium sulfate), filtered, and the solvent evaporated under reduced pressure to give crude product (341 mg) as a yellow oil. The crude product was purified by flash column chromatography on silica gel, eluting with ethyl acetate/hexane (5:95 increasing to 20:80) to give (±)-acetic acid 1-(4-trans-azidocyclohexyl)-4-phenylbutyl ester (276 mg, 80%) as a colorless oil: $^1$H NMR (CDCl3) 7.27 (2H, m), 7.16 (3H, m), 4.80 (1H, m), 3.19 (1H, m), 2.60 (2H, m), 2.05 (3H, s), 2.03 (2H, m), 1.77 (2H, m), 1.55 (4H, m), 1.48 (1H, m), 1.29 (2H, m), 1.09 (2H, m).

Step 9: (±)-1-(4-trans-Azidocyclohexyl)-4-phenylbutan-1-ol

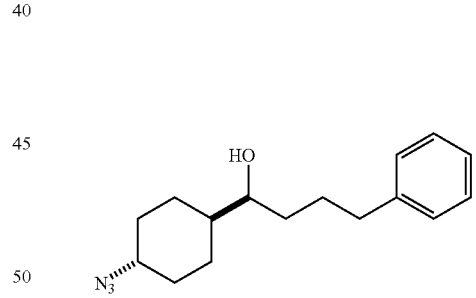

A solution of (±)-acetic acid 1-(4-trans-azidocyclohexyl)-4-phenylbutyl ester (240 mg, 0.76 mmol) in methanol (2 ml) and 3N sodium hydroxide solution (1.3 ml, 3.9 mmol) was stirred under nitrogen at 70° C. for eighteen hours. The mixture was partially concentrated under reduced pressure. The aqueous residue was partitioned between ethyl acetate (40 ml) and water (10 ml) and the layers were separated. The organic layer was washed with water (10 ml), and brine (10 ml), dried (sodium sulfate), filtered, and the solvent evaporated under reduced pressure to give crude (±)-1-(4-trans-azidocyclohexyl)-4-phenylbutan-1-ol (201 mg 97%) as a colorless oil: $^1$H NMR (CDCl3) 7.27 (2H, m), 7.19 (3H, m), 3.41 (1H, m), 3.20 (1H, m), 2.64 (2H, m), 2.05 (2H, s), 1.91 (1H, m), 1.82 (1H, m), 1.73 (1H, m), 1.65 (1H, m), 1.54-1.40 (3H, m), 1.34-1.09 (5H, m).

Step 10: (±)-1-(4-trans-Aminocyclohexyl)-4-phenylbutan-1-ol

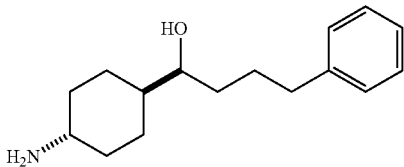

A mixture of (±)-1-(4-trans-azidocyclohexyl)-4-phenylbutan-1-ol (164 mg, 0.60 mmol), and 10% palladium on carbon (60 mg) in ethanol (6 ml) was hydrogenated (hydrogen balloon) for 18 hours. The catalyst was removed by filtration through diatomaceous earth. The filter cake was washed with ethanol (3×5 ml) and the filtrate was concentrated under reduced pressure to give white solid (151 mg). The solid was chromatographed on a 2 mm silica gel prep plate eluting with methanol:methylene chloride:ammonium hydroxide (20:80:2) to give a white solid (124 mg). The solid was triturated with ethyl acetate (2 ml), filtered off, and dried to give (±)-1-(4-trans-aminocyclohexyl)4-phenylbutan-1-ol (124 mg, 84%) as a white solid: MS=248.2 (M+1).

Step 11: (±)-4-Phenyl-1-trans-[4-(1H-pyrazolo[3,4-d]pyrimidin-4-ylamino)cyclohexyl]butan-1-ol

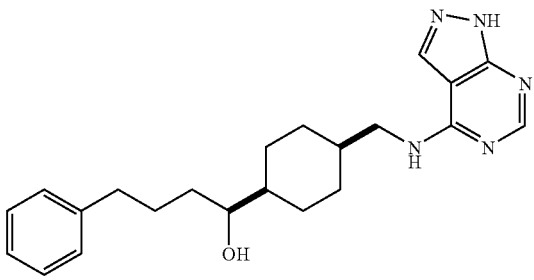

Employing the procedure substantially as described in Example 49 above but substituting (±)-1-(4-trans-aminocyclohexyl)-4-phenylbutan-1-ol for (±)-1-[cis-4-(aminomethyl)cyclohexyl]-3-phenylpropan-1-ol, the product (±)-4-phenyl-1-trans-[4-(1H-pyrazolo[3,4-d]pyrimidin-4-ylamino)cyclohexyl]butan-1-ol (14 mg, 39%) was obtained as a pale yellow solid: ¹H NMR (CDCl3) 9.2 (1H, br s), 8.33 (1H, s), 7.95 (1H, s), 7.29 (2H, m), 7.20 (3H, m), 5.2 (1H, br s), 3.7 (1H, br s), 3.47 (1H, m), 2.67 (2H, m), 2.25 (2H, m), 1.99 (1H, m), 1.82 (2H, m), 1.68-1.24 (9H, m). MS=366.1 (M+1).

EXAMPLE 53 trans-{4-[2-(2-Chlorophenyl)ethoxy]cyclohexyl}-(1H-pyrazolo[3,4-d]pyrimidin-4-yl)amine

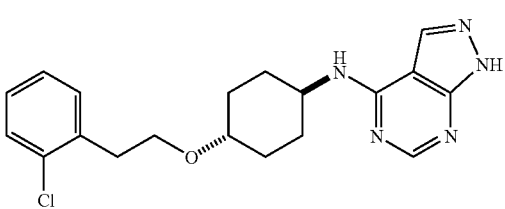

Employing the procedure substantially as described in Example 1 above but using 2-chlorophenyl acetaldehyde, the product (12 mg, 32%) was obtained as a white solid: ¹H NMR (CDCl3) 11.5 (1H, br s), 8.40 (1H, s), 7.92 (1H, s), 7.30 (1H, m), 7.28 (1H, m), 7.18 (2H, m), 6.0 (1H, br s), 4.1 (1H, br s), 3.71 (2H, t, J 7 Hz), 3.34 (1H, m), 3.03 (2H, t, J 7 Hz), 2.22 (2H, d, J 11 Hz), 2.10 (2H, d, J 11 Hz), 1.49 (2H, m), 1.40 (2H, m), MS: 372.2 (M+1).

EXAMPLE 54 trans-{4-[2-(2-Chloro-6-fluorophenyl)ethoxy]cyclohexyl}-(1H-pyrazolo[3,4-d]pyrimidin-4-yl)amine

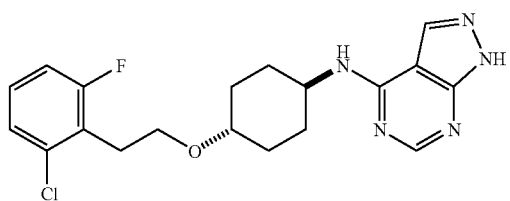

Employing the procedure substantially as described in Example 1 above but using 2-chloro-6-fluorophenylacetaldehyde, the product (15 mg, 38%) was obtained as a white solid: ¹H NMR (CDCl3) 11.7 (1H, br s), 8.41 (1H, s), 7.92 (1H, s), 7.15 (2H, m), 6.97 (1H, m), 5.9 (1H, br s), 4.1 (1H, br s), 3.66 (2H, t, J7.5 Hz), 3.38 (1H, m), 3.09 (2H, m), 2.21 (2H, d, J 13 Hz), 2.09 (2H, d, J 11 Hz), 1.49 (2H, m), 1.40 (2H, m), MS: 390.2 (M+1).

EXAMPLE 55 trans-{4-[2-(2,6-Dichlorophenyl)ethoxy]cyclohexyl)-(1H-pyrazolo[3,4-d]pyrimidin-4-yl)amine

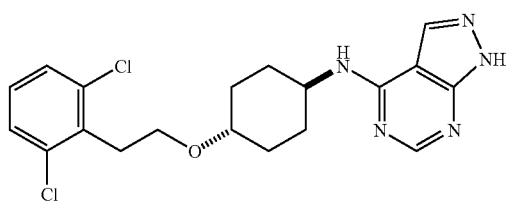

Employing the procedure substantially as described in Example 1 above but using 2,6-dichlorophenylacetaldehyde, the product (12 mg, 29%) was obtained as a light yellow solid: ¹H NMR (CDCl3) 11.4 (1H, br s), 8.40 (1H, s), 7.93 (1H, s), 7.28 (2H, m), 7.10 (1H, t, J 8 Hz), 5.9 (1H, br s), 4.1 (1H, br s), 3.67 (2H, t, J 8 Hz), 3.39 (1H, m), 3.26 (2H, t, J 8 Hz), 2.23 (2H, d, J 13 Hz), 2.12 (2H, d, J 10 Hz), 1.52 (2H, m), 1.40 (2H, m), MS: 407.2 (M+1).

EXAMPLE 56 trans-{4-[2-(2-Bromophenyl)ethoxy]cyclohexyl}-(1H-pyrazolo[3,4-d]pyrimidin-4-yl)amine

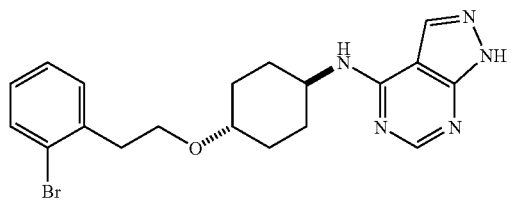

Employing the procedure substantially as described in Example 1 above but using 2-bromophenylacetaldehyde, the product (19.5 mg, 46%) was obtained as an off-white solid: ¹H NMR (CDCl3) 11.5 (1H, br s), 8.41 (1H, s), 7.92 (1H, s), 7.54 (1H, d, J 8 Hz), 7.26 (2H, m), 7.10 (1H, m), 5.9 (1H, br s), 4.1 (1H, br s), 3.71 (2H, t, J 7 Hz), 3.34 (1H, m), 3.04 (2H, t, J 7 Hz), 2.22 (2H, d, J 11 Hz), 2.10 (2H, d, J 10 Hz), 1.49 (2H, m), 1.39 (2H, m). MS: 417.2 (M+1).

EXAMPLE 57

(3R,1R and 3S,1S) [3-(2,2-Difluoro-2-p-tolyl-ethoxy)-cyclopentyl]-(1H-pyrazolo[3,4-d]pyrimidin-4-yl)-amine

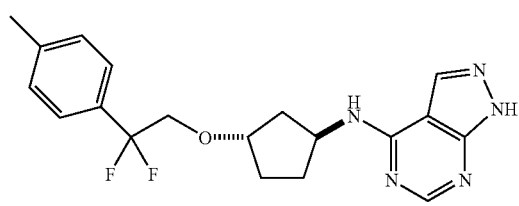

Step 1: trans [3-(2-Bromo-3-phenyl-allyloxy)-cyclopentyl]-carbamic acid benzyl ester

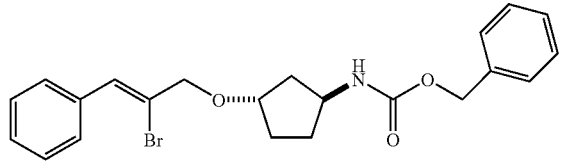

To a stirred solution of 12 g of racemic [3-(tert-butyl-dimethyl-silyloxy)-cyclopentyl]-carbamic acid benzyl ester [prepared from racemic trans 1-amino cyclopentanol using the procedures described for Example 11, Steps 1 and 2], 10 g of 2-bromocinnamaldehyde and 200 mL of anhydrous acetonitrile was added 1 g of bismuth bromide followed by 10 mL of triethylsilane over 30 min. After stirring for an additional 45 min at room temperature, the reaction was quenched with 200 mL of saturated sodium carbonate. The mixture was extracted with 3×100 mL portions of ethyl acetate, the combined extracts dried over magnesium sulfate and concentrated under reduced pressure. Chromatography using a gradient of 0% to 25% ethyl acetate in hexane gave 14 g of product as a crystalline solid: MS (m+2)=432.2; 1H NMR (400 MHz, CDCl3) 7.6 (d, 2H), 7.3 (m, 8H), 7.0 (s, 1H), 5.1 (s, 2H), 4.7 (br s, 1H), 4.2 (s, 2H), 4.1 (m, 1H), 2.2 (m, 2H), 2.0 (m, 1H), 1.8 (m, 1H), 1.62 (m, 1H), 1.4 (m, 1H).

Step 2: trans [3-(3-Phenyl-2-p-tolyl-allyloxy)-cyclopentyl]-carbamic acid benzyl ester

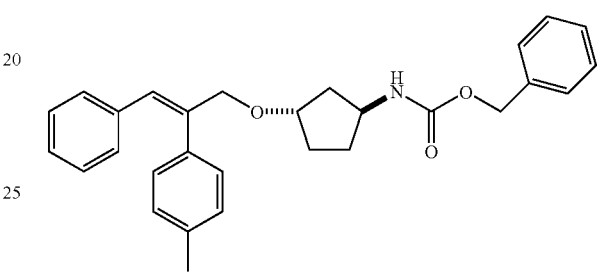

A stirred mixture of 10 g of racemic trans [3-(2-bromo-3-phenyl-allyloxy)-cyclopentyl]-carbamic acid benzyl ester, 4.7 g of p-tolylboronic acid, 160 mg of o-biphenyl dicyclohexylphosphine, 52 mg of palladium acetate, 4 g of potassium fluoride and 25 mL of anhydrous tetrahydrofuran was stirred at room temperature for 1 h then heated to 50° C. for 3h under nitrogen atmosphere. The mixture was cooled diluted with 50 mL of sodium carbonate and extracted with 3×100 mL portions of ethyl acetate. The combined extracts were dried over magnesium sulfate and concentrated under reduced pressure. Chromatography using a gradient of 0% to 25% ethyl acetate in hexane gave 10.8 g of product as a crystalline solid: MS (m+1)=442.3; 1H NMR (400 MHz, CDCl3) 7.35 (m, 4H), 7.1 (m, 8H), 7.0 (d, 2H), 6.6 (s, 1H), 5.1 (s, 2H), 4.7 (br s, 1H), 4.2 (s, 2H), 4.1 (m, 1H), 2.37 (s, 3H), 2.2 (m, 2H), 1.986 (m, 1H), 1.78 (m, 1H), 1.62 (m, 1H), 1.4 (m, 1H).

Step 3: trans [3-(2-Oxo-2-p-tolyl-ethoxy)-cyclopentyl]-carbamic acid benzyl ester

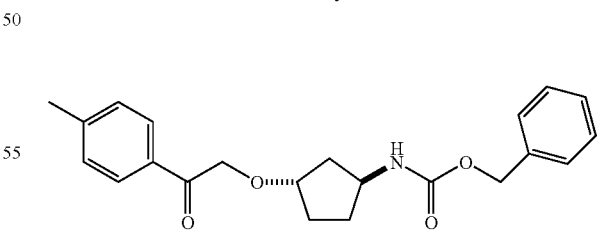

To a stirred solution of 10 g of trans [3-(3-phenyl-2-p-tolyl-allyloxy)-cyclopentyl]-carbamic acid benzyl ester in 500 mL of dichloromethane cooled to −78° C. was dispersed a stream of ozone from an ozone generator until a blue color persisted. The excess ozone was purged with nitrogen until the blue color dissipated, and 20 mL of methyl sulfide was added. After warming to room temperature over 30 min, the solution was concentrated under reduced pressure. Chromatography over silica gel eluting with a gradient of 5%-45% ethyl acetate in hexane gave 6.5 g of product as a white crystalline solid: MS (m+1)=368.3; 1H NMR (400 MHz, CDCl3) 7.35 (m, 2H), 7.1 (m, 5H), 7.0 (m, 2H), 5.1 (s, 2H), 4.7 (m, 1H), 4.2 (s, 2H), 4.1 (m, 1H), 2.35 (s,3H), 2.2 (m, 2H), 1.95 (m, 1H), 1.74 (m, 1H), 1.6 (m, 1H), 1.4 (m, 1H).

Resolution on a Chiacel OJ HPLC column gave the enantiomers: $[\alpha]_D^{25}$=+3.5°, (c=1, MeOH) and: $[\alpha]_D^*$=−3.5°, (c=1, MeOH).

Step 4: trans [3-(2,2-Difluoro-2-p-tolyl-ethoxy)-cyclopentyl]-carbamic acid benzyl ester

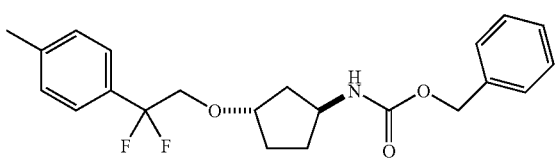

A mixture of 7 g trans [3-(2-oxo-2-p-tolyl-ethoxy)-cyclopentyl]-carbamic acid benzyl ester and 20 mL of diethylamino sulfur-trifluoride was heated under a nitrogen atmosphere to 60° C. for 5 h. The mixture was cooled in an ice bath and quenched with 50 mL of saturated sodium bicarbonate. After stirring for 1 h, the black mixture was extracted with 2×100 mL of dichloromethane and extracts dried over magnesium sulfate and concentrated under reduced pressure. Chromatography over silica gel eluting with a gradient of 0%-25% ethyl acetate in hexane and crystallization with hexane containing 2% ether gave 5.2 g of product as a crystalline solid: MS (m−18)=371.3; 1H NMR (400 MHz, CDCl3) 7.42 (dd, 21), 7.4 (m, 5H), 7.26 (dd, 2H), 5.17 (s, 2H), 5.0 (m, 1H), 4.2 (m, 1H), 4.07 (m, 1H), 3.8 (t, J=14 Hz, 2H), 2.42 (s, 3H), 2.17 (m, 2H), 1.95 (m, 1H), 1.72 (m, 1H), 1.6 (m, 1H), 1.4 (m, 1H).

Step 5: trans 3-(2,2-Difluoro-2-p-tolyl-ethoxy)-cyclopentylamine

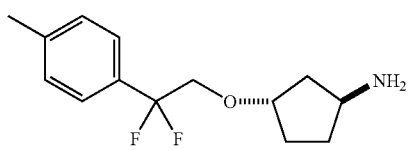

A mixture of 600 mg of trans [3-(2,2-Difluoro-2-p-tolyl-ethoxy)-cyclopentyl]-carbamic acid benzyl ester and 500 mg of 10% palladium on carbon in 25 mL of ethanol was stirred under an atmosphere of hydrogen for 2 h. Removal of the catalyst by filtration and concentration under reduced pressure gave 400 mg of product as an oil: MS (m+1)=256.3; 1H NMR (400 MHz, CDCl3) 7.4 (dd, 2H), 7.22 (dd, 2H), 4.05 (m, 1H), 3.75 (t, J=14 Hz, 2H), 3.5 (m, 1H), 2.4 (s, 3H), 2.2 (m, 2H), 2.0 (m, 2H), 1.62 (m, 1H), 1.5 (m, 1H), 1.24 (m, 1H).

Step 6: (3R,1R and 3S,1S) [3-(2,2-Difluoro-2-p-tolyl-ethoxy)-cyclopentyl]-(1H-pyrazolo[3,4-d]pyrimidin-4-yl)-amine

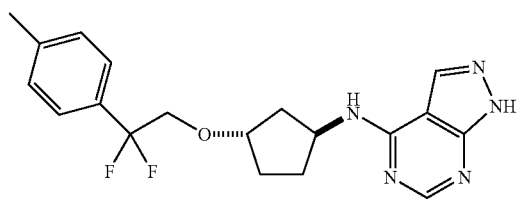

A mixture of 400 mg of trans 3-(2,2-Difluoro-2-p-tolyl-ethoxy)-cyclopentylamine, 0.40 g of 4-chloro-1-(tetrahydropyran-2-yl)-1H-pyrazolo[3,4-d]pyrimidine, and 0.2 mL of N,N-diisopropylethylamine in 25 mL of 2-propanol was heated to 80° C. under nitrogen overnight. The mixture was cooled, and concentrated under reduced pressure. Chromatography over silica gel eluting with a gradient of 0%-75% ethyl acetate in hexane gave 0.75 g of product as a white solid: MS (m+1)=458.28. The solid was heated in 25 mL of 2-propanol and 2 mL of 12N HCl to 90° C. for 1 h, cooled and concentrated under reduced pressure to dryness. The solid residue was triturated with 50 mL of ether and filtered. The solid hydrochloride salt was dissolved in 100 mL of methanol and 2 mL of concentrated aqueous ammonia and again concentrated to dryness. The resulting residue was extracted with 100 mL of 5% methanol in chloroform filtered and concentrated to dryness under reduced pressure. Chromatography over silica gel eluting with a gradient of 0%-10% methanol in ethyl acetate gave 0.58 g of product as a white solid: MS (m+1)=374.4; 1H NMR 8.3 (s, 1H), 7.98 (s, 1H), 7.42 (d, 2H), 7.26 (d, 2H), 4.6 (br s, 1H), 4.18 (s, 1H), 3.82 (t, J=14 Hz, 2H), 2.4 (s, 3H), 2.35 (m, 2H), 2.05 (m, 1H), 1.82 (m, 1H), 1.65 (m, 1H), 1.6 (m, 1H).

Resolution into the pure enantiomers could be performed by isocratic elution on Chiralcel OJ at 1 mL/min, eluting with 25% ethanol in hexane with 0.1% diethylamine.

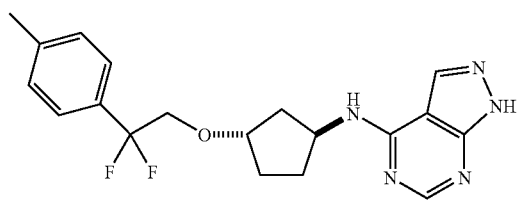

(3S,1S) [3-(2,2-Difluoro-2-p-tolyl-ethoxy)-cyclopentyl]-(1H-pyrazolo[3,4-d]pyrimidin-4-yl)-amine:
$[\alpha]_D^{25° C.}$=+24.8° (c=1, MeOH); MS (m+1)=374.4; 1H NMR 8.3 (s, 1H), 7.98 (s, 1H), 7.42 (d, 2H), 7.26 (d, 2H), 4.6 (br s, 1H), 4.18 (s, 1H), 3.82 (t, J=14 Hz, 2H), 2.4 (s, 3H), 2.35 (m, 2H), 2.05 (m, 1H), 1.82 (m, 1H), 1.65 (m, 1H), 1.6 (m, 1H).

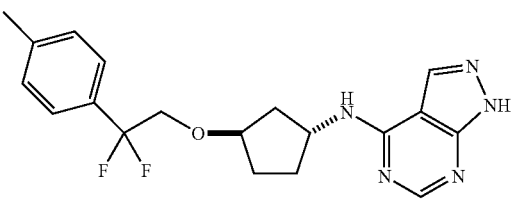

(3R,1R) [3-(2,2-Difluoro-2-p-tolyl-ethoxy)-cyclopentyl]-(1H-pyrazolo[3,4-d]pyrimidin-4-yl)-amine:
$[\alpha]_D^{25°\,C.}=-24.9°$ (c=1, MeOH); MS (m+1)=374.4; 1H NMR 8.3 (s, 1H), 7.98 (s, 1H), 7.42 (d, 2H), 7.26 (d, 2H), 4.6 (br s, 1H), 4.18 (s, 1H), 3.82 (t, J=14 Hz, 2H), 2.4 (s, 3H), 2.35 (m, 2H), 2.05 (m, 1H), 1.82 (m, 1H), 1.65 (m, 1H), 1.6 (m, 1H).

EXAMPLE 58

N-{(1R,3R,4R)-3-[2,2-difluoro-2-(4-methylphenyl)ethoxy]-4-fluorocyclopentyl}-1H-pyrazolo[3,4-d]pyrimidin-4-amine

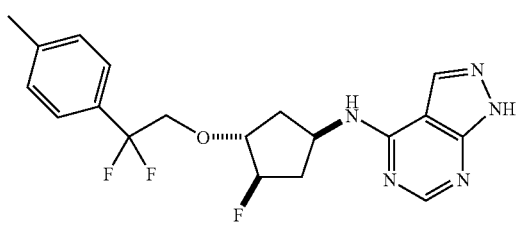

Step 1: 1-[(1R,3R,4R and 1S,3S,4S)-3-fluoro-4-hydroxycyclopentyl]-3-[(1Z)-prop-1-en-1-yl]-4-vinyl-1H-pyrrole-2,5-dione

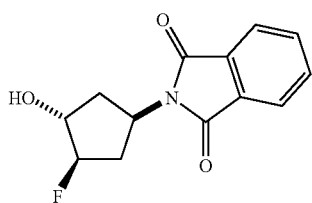

To a stirred solution of 3.2 g of trans 4-(phthalimidocyclopentene oxide [prepared from cyclopenten-3-ol as described by S. Barrett, P. O'Brien, H. Christian Steffens, T. D. Towers and M. Voth, Tetrahedron, 56 (2000) 9633-9640.] in 100 mL of dichloromethane cooled in an ice bath to 0° C. was added 2 mL of hydrogen fluoride-pyridine. After stirring for an additional 2 h at 0° C., the reaction was quenched with 200 mL of water. The aqueous layer was extracted with 100 mL of dichloromethane, the combined extracts dried over magnesium sulfate and concentrated under reduced pressure. Chromatography using a gradient of 25% to 80% ethyl acetate in hexane gave 3.5 g of product as a white crystalline solid: MS (m)=249.4; 1H NMR (400 MHz, CDCl3) 7.82 (m, 2H), 7.72 (m, 2H), 5.05 (m, 1H), 4.36 (m, 1H), 4.07 (m, 1H), 2.7 (m, 1H), 2.4 (m, 1H), 2.08 (m, 1H), 1.94 (m, 1H), 1.6 (m, 1H).

Step 2: benzyl-[(1R,3R,4R and 1S,3S,4S)-3-fluoro-4-hydroxycyclopentyl]carbamate

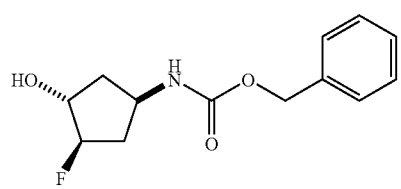

A mixture of 3.5 g of 1-[(1R,3R,4R and 1S,3S,4S)-3-fluoro-4-hydroxycyclopentyl]-3-[(1Z)-prop-1-en-1-yl]-4-vinyl-1H-pyrrole-2,5-dione, 100 mL of ethanol and 1 mL of hydrazine hydrate cooled was heated to reflux for 2 h. After cooling 10 mL of 6N HCl was added and the mixture again heated to reflux for 1 h, cooled, filtered and concentrated under reduced pressure to dryness. The solid residue was stirred overnight in a mixture of 100 mL of anhydrous acetonitrile, 4.5 g of benzyl succinimidyl carbonate and 5 mL of triethylamine. The mixture was concentrated under reduced pressure, and partitioned between 50 mL of 1N HCl and 3×50 mL portions of ethyl acetate. The combined extracts dried over magnesium sulfate and concentrated under reduced pressure. Chromatography using a gradient of 0% to 50% ethyl acetate in hexane gave 3.5 g of product as a white crystalline solid: MS (m+1)=254.3.

Steps 3-9: N-{(1R,3R,4R)-3-[2,2-difluoro-2-(4-methylphenyl)ethoxy]-4-fluorocyclopentyl}-1H-pyrazolo[3,4-d]pyrimidin-4-amine

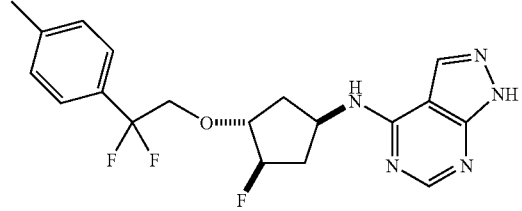

From benzyl -[(1R,3R,4R and 1S,3S,4S)-3-fluoro-4-hydroxycyclopentyl]carbamate using the procedures described for Example 57: MS (m+1)=342.3.

EXAMPLE 59

N-{(1S,3S)-3-[(2R)-2-fluoro-2-(4-methylphenyl)ethoxy]cyclopentyl}-1H-pyrazolo[3,4-d]pyrimidin-4-amine

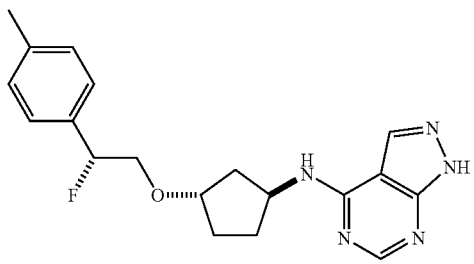

MS (m+1)=356.3

EXAMPLE 60

N-{(1S,3S)-3-[(2S)-2-fluoro-2-(4-methylphenyl)ethoxy]cyclopentyl}-1H-pyrazolo[3,4-d]pyrimidin-4-amine

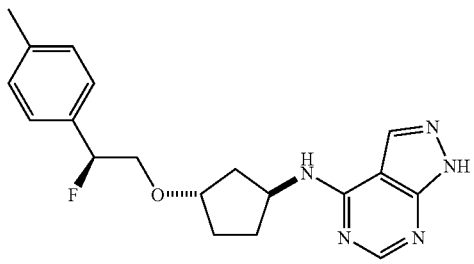

MS (m+1)=356.3

EXAMPLE 61

N-{(1S,3S)-3-[(2R)-2-fluoro-2-phenylethoxy]cyclopentyl}-1H-pyrazolo[3,4-d]pyrimidin-4-amine

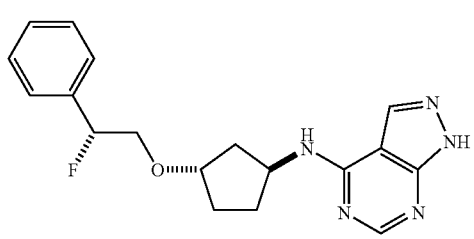

MS (m+1)=342.3

EXAMPLE 62

N-{(1S,3S)-3-[(2S)-2-fluoro-2-phenylethoxy]cyclopentyl}-1H-pyrazolo[3,4-d]pyrimidin-4-amine

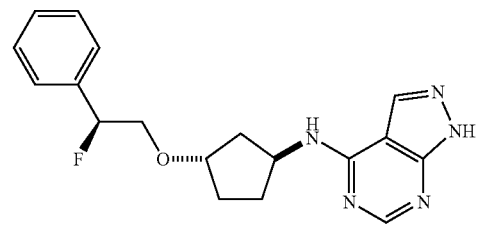

MS (m+1)=342.3

EXAMPLE 63

N-{(1R,3R,4R)-3-fluoro-4-[2-(4-methylphenyl)ethoxy]cyclopentyl}-1H-pyrazolo[3,4-d]pyrimidin-4-amine

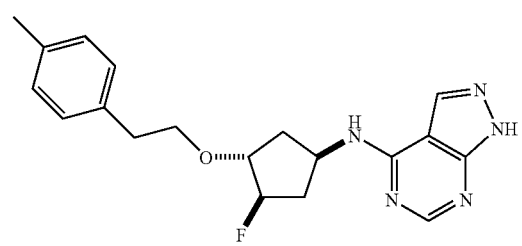

MS (m+1)=356.3

EXAMPLE 64

N-{(1R,3S,4R)-3-fluoro-4-[2-(4-methylphenyl)ethoxy]cyclopentyl}-1H-pyrazolo[3,4-d]pyrimidin-4-amine

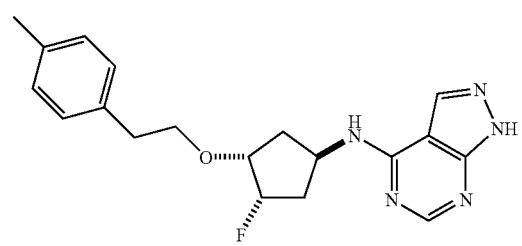

MS (m+1)=356.3

EXAMPLE 65

N-{(1R,3R,4S)-3-[2,2-difluoro-2-(4-methylphenyl)ethoxy]4-fluorocyclopentyl}-1H-pyrazolo[3,4-d]pyrimidin-4-amine

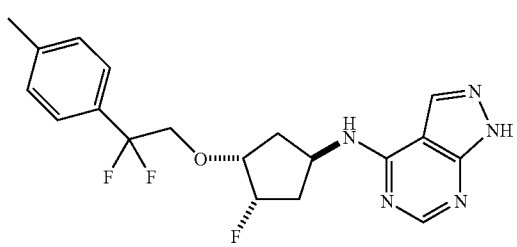

MS (m+1)=392.3

EXAMPLE 66

N-{(1S,2S,3S)-3-[2,2-difluoro-2-(4-methylphenyl)ethoxy]-2-fluorocyclopentyl}-1H-pyrazolo[3,4-d]pyrimidin-4-amine

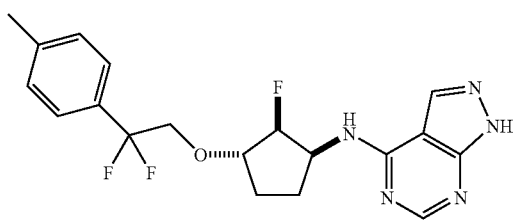

MS (m+1)=392.3

EXAMPLE 67

N-{(1S,2R,3S)-3-[2,2-difluoro-2-(4-methylphenyl)ethoxy]-2-fluorocyclopentyl}-1H-pyrazolo[3,4-d]pyrimidin-4-amine

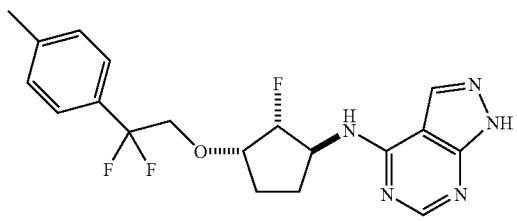

MS (m+1)=392.3

EXAMPLE 68

(1R)-1-(4-methylphenyl)-2-{[(1S,3S)-3-(1H-pyrazolo[3,4-d]pyrimidin-4-ylamino)cyclopentyl]oxy}ethanol

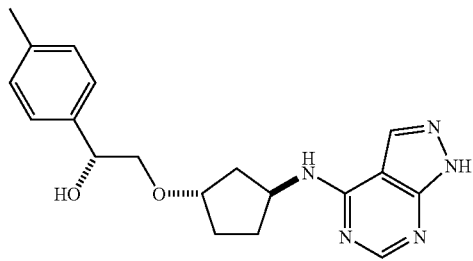

MS (m+1)=354.4

EXAMPLE 69

(1S)-1-(4-methylphenyl)-2-{[(1S,3S)-3-(1H-pyrazolo[3,4-d]pyrimidin-4-ylamino)cyclopentyl]oxy}ethanol

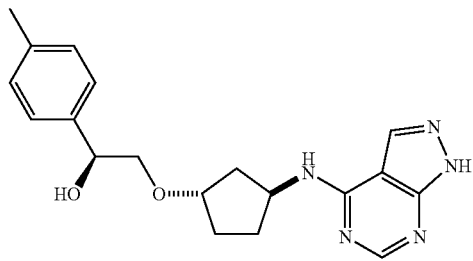

MS (m+1)=354.4

EXAMPLE 70

(1R)-1-(2-fluorophenyl)-2-{[trans-4-(1H-pyrazolo[3,4-d]pyrimidin-4-ylamino)cyclohexyl]oxy}ethanol

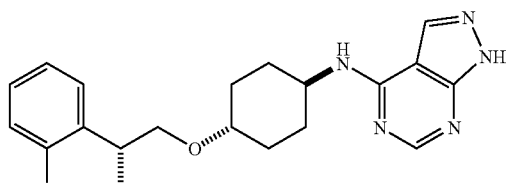

MS (m+1)=372.4; 1H NMR (400 MHz, CDCl$_3$) 8.35 (s, 1H), 7.94 (s, 1H), 7.56 (t, 1H), 7.29 (m, 1H), 7.25 (t, 1H), 7.05 (t, 1H), 5.20 (d, J=7 Hz, 1H), 4.0 (m, 2H), 3.76 (d, 1H), 3.48 (t, 2H), 3.45 (m, 2H), 2.22 (d, 2H), 2.15 (d, 2H), 2.05 (br s, 1H), 1.55 (q, 2H), 1.45 (br m, 2H).

EXAMPLE 71

(1S)-1-(2-fluorophenyl)-2-{[trans-4-(1H-pyrazolo[3,4-d]pyrimidin-4-ylamino)cyclohexyl]oxy}ethanol

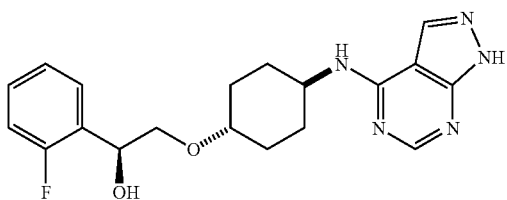

MS (m+1)=372.4; 1H NMR (400 MHz, CDCl₃) 8.35 (s, 1H), 7.94 (s, 1H), 7.56 (t, 1H), 7.29 (m, 1H), 7.25 (t, 1H), 7.05 (t, 1H), 5.20 (d, J=7 Hz, 1H), 4.0 (m, 2H), 3.76 (d, 1H), 3.48 (t, 2H), 3.45 (m, 2H), 2.22 (d, 2H), 2.15 (d, 2H), 2.05 (br s, 1H), 1.55 (q, 2H), 1.45 (br m, 2H).

EXAMPLE 72

N-{trans-4-[(2R,S)-2-(2,6-difluorophenyl)-2-fluoroethoxy]cyclohexyl}-1H-pyrazolo[3,4-d]pyrimidin-4-amine

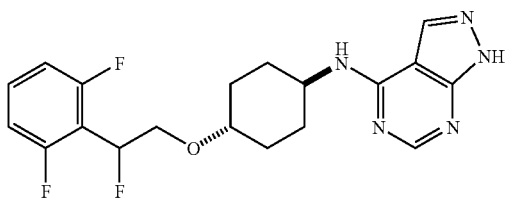

Step 1: trans-[4-(2-(2,6-Difluorophenyl)-3-phenyl-allyloxy)-cyclohexyl]-carbamic acid benzyl ester

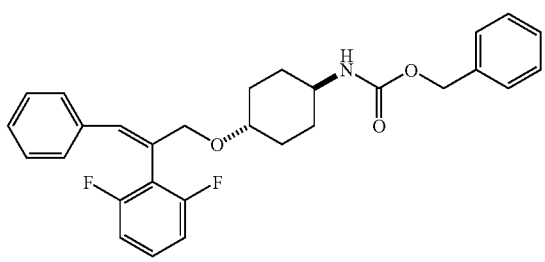

A stirred mixture of 1.8 g of trans-[4-(2-bromo-3-phenyl-allyloxy)-cyclohexyl]-carbamic acid benzyl ester, 0.9 g of potassium 2,6-difluorophenyltrifluoroborate (G. A. Molander and B. Biolatto, Journal of Organic Chemistry, (2003), 68, 4302-4314), 1.8 mL of triethylamine, 0.30 g of PdCl2(dppf). CH₂Cl₂, 50 mL of ethanol was heated to reflux for 12 h. The mixture was cooled and partitioned between 10 mL of water and 50 mL of chloroform The chloroform extract was washed with 50 mL of saturated sodium carbonate, 50 mL of saturated brine, dried over magnesium sulfate and concentrated under reduced pressure. Chromatography over silica gel eluting with a gradient of 10%-25% ethyl acetate in hexane gave 1.1 g of product as a white crystalline solid: MS (m+1)= 478.3.

Steps 2-7: N-{trans-4-[(2R,S)-2-(2,6-difluorophenyl)-2-fluoroethoxy]cyclohexyl}-1H-pyrazolo[3,4-d]pyrimidin-4-amine

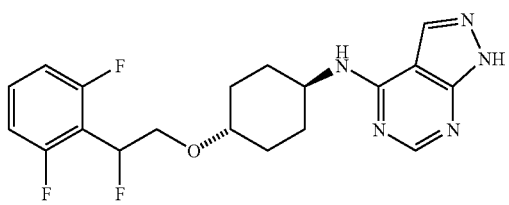

From trans-[4-(2-(2,6-difluorophenyl)-3-phenyl-allyloxy)-cyclohexyl]-carbamic acid benzyl ester using the procedures described for Example 11: MS (m+1)=374.4; MS (m+1)=374.4; 1H NMR (400 MHz, CDCl₃) 8.4 (s, 1H), 7.96 (s, 1H), 7.45 (t, 1H), 7.38 (m, 1H), 7.23 (m, 1H), 7.08 (t, 1H), 5.90 (dd, 1H), 5.3 (br s, 1H), 4.2 (m, 1H), 3.85 (m, 2H), 3.75 (br s, 1H), 2.2 (dd, 4H), 1.55 (m, 5H).

Resolution into the pure enantiomers could be performed by isocratic elution on ChiralPak AD at 1 mL/min, eluting with 30% 2-propanol in hexane: N-{trans-4-[(2S)-2-(2,6-difluorophenyl)-2-fluoroethoxy]cyclohexyl}-1H-pyrazolo[3,4-d]pyrimidin-4-amine

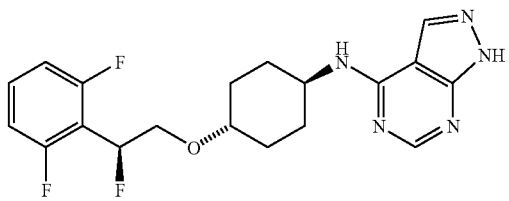

$[\alpha]_D^{25°\ C.}$=+12° (c=1, MeOH); MS (m+1)=374.4; 1H NMR (400 MHz, CDCl₃); 1H NMR (400 MHz, CDCl₃) 8.4 (s, 1H), 7.96 (s, 1H), 7.45 (t, 1H), 7.38 (m, 1H), 7.23 (m, 1H), 7.08 (t, 1H), 5.90 (dd, 1H), 5.3 (br s, 1H), 4.2 (m, 1H), 3.85 (m, 2H), 3.75 (br s, 1H), 2.2 (dd, 4H), 1.55 (m, 5H).

N-{trans-4-[(2R)-2-(2,6-difluorophenyl)-2-fluoroethoxy]cyclohexyl}-1H-pyrazolo[3,4-d]pyrimidin-4-amine

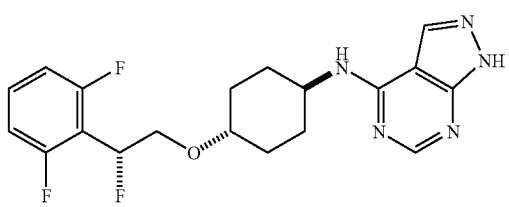

$[\alpha]_D^{25°\ C.}$=−12° (c=1, MeOH); MS (m+1)=374.4; 1H NMR (400 MHz, CDCl₃) 8.4 (s, 1H), 7.96 (s, 1H), 7.45 (t, 1H), 7.38

(m, 1H), 7.23 (m, 1H), 7.08 (t, 1H), 5.90 (dd, 1H), 5.3 (br s, 1H), 4.2 (m, 1H), 3.85 (m, 2H), 3.75 (br s, 1H), 2.2 (dd, 4H), 1.55 (m, 5H).

EXAMPLE 73

N-(cis-3-{[(2S,R)-2-fluoro-2-(2-fluorophenyl)ethoxy]methyl}cyclobutyl)-1H-pyrazolo[3,4-d]pyrimidin-4-amine

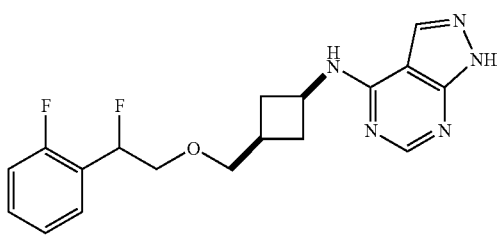

Step 1: {cis-3-[(benzyloxy)methyl]cyclobutyl}amine

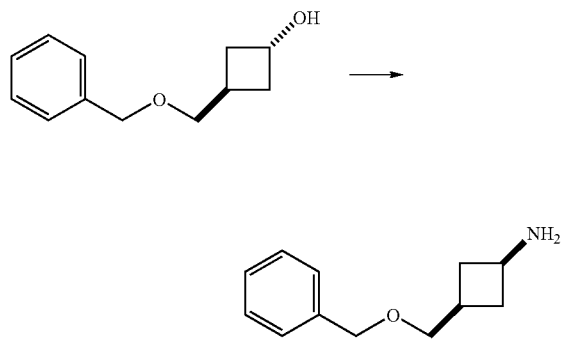

To a stirred solution of 7.1 g of trans-3-(benzyloxymethyl)cyclobutanol [prepared as described by V. Kaiwar, C. B. Reese, E. J. Gray, S. Neidle, J. Chem. Soc. Perkin Trans, 1, (1995), 2281-2287.], and 10.3 mL of triethylamine in 200 mL of dry dichloromethane cooled in an ice bath to 0° C. was added 3.5 mL of methanesulfonyl chloride over 45 min. After stirring for an additional 30 min in the cold, the reaction was quenched with 20 mL of water and allowed to stir at room temperature for 30 min. The organic layer was washed with 50 mL of 2N HCl, then 50 mL of saturated sodium bicarbonate, dried over magnesium sulfate and concentrated under reduced pressure. Drying under vacuum gave 10.21 g of the mesylate as an oil. The crude mesylate was heated to 95° C. with 24 g of sodium azide in 50 mL of anhydrous DMF for 12 h, the reaction mixture cooled and partitioned between 500 mL of water and 3×50 mL of diethyl ether. The combined extracts were washed with 100 mL of water, dried over magnesium sulfate and concentrated under reduced pressure. Drying under vacuum gave 8.2 g of cis-azide as an oil. To an ice cold solution of 6.4 g of the cis-azide in 250 mL of ethanol was added 1.3 g of sodium borohydride followed by 8.7 g of nickel (II) chloride hexahydrate. The mixture turned black with gas evolution. When the vigorous reaction subsided, the mixture was allowed to warm to room temperature and stir for 3 h, diluted with 200 mL of saturated sodium bicarbonate and filtered through diatomaceous earth. The filtrate was extracted 3×200 mL of ethyl acetate, the combined extracts dried over magnesium sulfate and concentrated under reduced pressure. Drying under vacuum gave 6.0 g of product as an oil: MS (m+2)=192.3; 1H NMR (400 MHz, CDCl3) 7.3 (m, 5H), 4.5 (s, 2H), 3.4 (d, 2H), 3.3 (m, 1H), 2.4 (dd, 2H), 2.08 (m, 1H), 1.8 (br s, —NH₂, 2H), 1.4 (dd, 2H).

Step 2: Benzyl [cis-3-(hydroxymethyl)cyclobutyl]carbamate

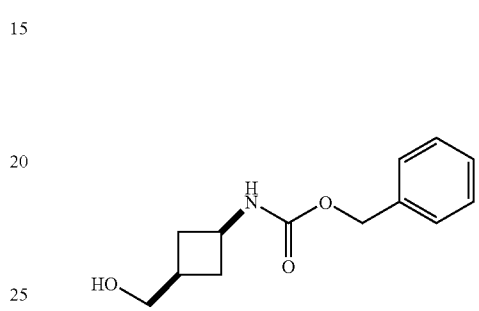

A mixture of 6.0 g of {cis-3-[(benzyloxy)methyl]cyclobutyl}amine, 2 g of 20% palladium hydroxide on carbon, 200 mL of methanol and 20 mL of acetic acid was stirred at room temperature under an atmosphere of hydrogen (balloon) for 24 h. The mixture was filtered to remove catalyst and concentrated under reduced pressure. Further drying under vacuum gave 6.5 g of the acetate salt of (cis-3-aminocyclobutyl)methanol as a thick resin. A mixture of 6.5 g of the acetate salt of (cis-3-aminocyclobutyl)methanol, 8 g of benzyl succinimidyl carbonate, 150 mL of anhydrous acetonitrile 15 mL of 2-propanol and 20 mL of triethylamine was stirred overnight at room temperature. The mixture was concentrated under reduced pressure and partitioned between 2×150 mL of ethyl acetate and 50 mL of water. The combined extracts were dried over magnesium sulfate and concentrated to dryness. Chromatography using a gradient of 25% to 75% ethyl acetate in hexane gave 10.8 g of product as a crystalline solid: MS (m+1)=236.3; 1H NMR (400 MHz, CDCl3) 7.37 (m, 5H), 5.18 (s, 2H), 4.92 (br s, 1H), 4.1 (m, 1H), 3.58 (s, 2H), 2.42 (dd, 2H), 2.1 (m, 1H), 1.7 (dd, 2H).

Steps 3-11: N-(cis-3-{[(2R,S)-2-fluoro-2-(2-fluorophenyl)ethoxy]methyl}cyclobutyl)-1H-pyrazolo[3,4-d]pyrimidin-4-amine

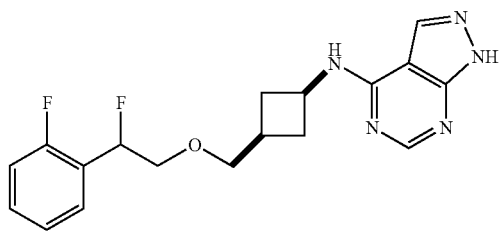

From benzyl [cis-3-(hydroxymethyl)cyclobutyl]carbamate using the procedures described for Example 11. MS (m+1)=360.3; 1H NMR 8.42 (s, 1H), 8.0 (s, 1H), 7.45 (t, 1H), 7.34 (t, 1H), 7.2 (t, 1H), 7.05 (t, 1H), 5.95 (dd, $J_{HF}$=47 Hz, 1H), 4.7 (br s, 1H), 3.82 (complex m, 2H), 3.58 (m, 2H), 2.65 (dd, 2H), 1.9 (dd, 2H).

Resolution into the pure enantiomers could be performed by isocratic elution on Chiralcel OJ at 1 mL/min, eluting with 30% ethanol in hexane with 0.1% diethylamine.

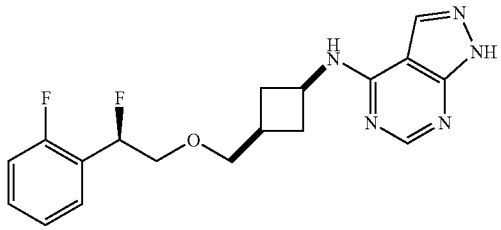

N-(cis-3-{[(2R)-2-fluoro-2-(2-fluorophenyl)ethoxy]methyl}cyclobutyl)-1H-pyrazolo[3,4-d]pyrimidin-4-amine: $[\alpha]^{D25°\ C.}$=−12° (c=1, MeOH);. MS (m+1)=360.3; 1H NMR 8.42 (s, 1H), 8.0 (s, 1H), 7.45 (t, 1H), 7.34 (t, 1H), 7.2 (t, 1H), 7.05 (t, 1H), 5.95 (dd, $J_{HF}$=47 Hz, 1H), 4.7 (br s, 1H), 3.82 (complex m, 2H), 3.58 (m, 2H), 2.65 (dd, 2H), 1.9 (dd, 2H).

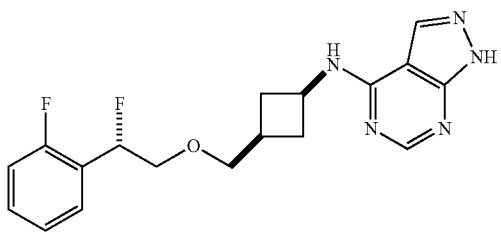

N-(cis-3-{[(2S)-2-fluoro-2-(2-fluorophenyl)ethoxy]methyl}cyclobutyl)-1H-pyrazolo[3,4-d]pyrimidin-4-amine: $[\alpha]^{D25°\ C.}$=+11° (c=1, MeOH); MS (m+1)=360.3; 1H NMR 8.42 (s, 1H), 8.0 (s, 1H), 7.45 (t, 1H), 7.34 (t, 1H), 7.2 (t, 1H), 7.05 (t, 1H), 5.95 (dd, $J_{HF}$=47 Hz, 1H), 4.7 (br s, 1H), 3.82 (complex m, 2H), 3.58 (m, 2H), 2.65 (dd, 2H), 1.9 (dd, 2H).

EXAMPLE 74

N-[trans-3-[2-(4-Methylphenyl)ethoxy]cyclopentyl}-1H-pyrazolo[3,4-d]pyrimidin-4-amine

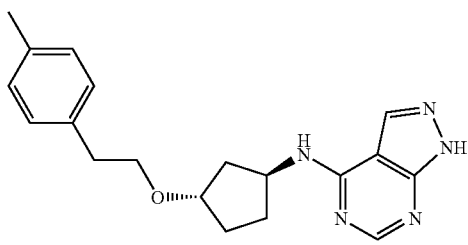

Step 1: tert-butyl (3-oxocyclopentyl)carbamate

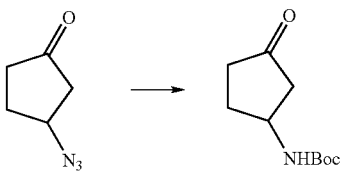

A mixture of 3-azidocyclopentanone (*Org. Lett.*, 1999, 1, 1107-1109) (3.25 g, 26.0 mmol), di-t-butyl dicarbonate (6.81 g, 31.2 mmol, 2.1 equiv.) and 10% palladium on carbon (0.43 g) in ethyl acetate (33 ml) was hydrogenated (hydrogen balloon) for 18 hours. The catalyst was removed by filtration through Celite. The filter cake was washed with ethyl acetate (3×10 ml) and the filtrate was concentrated under reduced pressure to give mixed oil and solid. The mixed oil and solid was triturated with ether: hexane (1:1, 12 ml) in an ice-bath. The resulting solid was filtered off and dried to give tert-butyl (3-oxocyclopentyl)carbamate (3.16 g, 61%), as a white solid. The mother liquor was chromatographed on silica gel, eluting with ethyl acetate:hexane (10:90 increasing to 50:50) to give additional tert-butyl (3-oxocyclopentyl)carbamate (0.40 g, 8%), as a white solid.

$^1$H NMR (CDCl3) 4.58 (1H, br s), 4.23 (1H, d, J 5 Hz), 2.63 (1H, dd, J 19, 7.5 Hz), 2.36 (2H, m), 2.25 (1H, m), 2.11 (1H, dd, J 19, 7.5 Hz), 1.85 (1H, m), 1.45 (9H).

MS.: 200.4 (M+1).

Step 2: tert-Butyl (trans-3-hydroxycyclopentyl)carbamate and (+−)-tert-Butyl (cis-3-hydroxycyclopentyl)carbamate

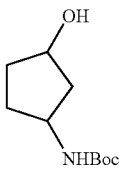

To a solution of tert-butyl (3-oxocyclopentyl)carbamate (1.99 g, 10.0 mmol) in ethanol (50 ml) under nitrogen cooled in an ice-bath was added sodium borohydride (0.79 g, 21 mmol). The mixture was stirred 2.5 hours at ice-bath temperature. The reaction was quenched by addition of saturated sodium bicarbonate solution (40 ml). The mixture was concentrated under reduced pressure to remove ethanol. The aqueous residue was diluted with water (10 ml) and extracted with ethyl acetate (2×100 ml). The extract was washed with water (10 ml), and brine (10 ml), dried (sodium sulfate), filtered, and the solvent evaporated under reduced pressure to give crude a white gum. The gum was chromatographed on silica gel, eluting with ethyl acetate:hexane (10:90 increasing to 75:25). The first isomer to elute was tert-butyl (cis-3-hydroxycyclopentyl)carbamate (0.92 g, 44%), solid white foam.

$^1$H NMR (CDCl3) 4.37 (1H, br s), 4.04 (1H, br s), 1.97-2.09 (3H, m), 1.77 (3H, m), 1.62 (1H, d, J 14 Hz), 1.44 (10H).

MS.: 202.3 (M+1).

The second isomer to elute was tert-butyl (trans-3-hydroxycyclopentyl)carbamate (0.93 g, 44%), white solid. $^1$H NMR (CDCl3) 4.47 (1H, br s), 4.40 (1H, m), 4.17 (1H, d, J 5 Hz), 2.21 (1H, m), 2.04 (2H, m), 1.57-1.68 (2H, m), 1.44 (9H), 1.41 (2H, m).

MS: 202.4 (M+1).

Step 3: Benzyl (trans-3-hydroxycyclopentyl)carbamate

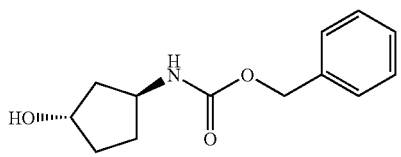

To a solution of tert-butyl (trans-3-hydroxycyclopentyl) carbamate (0.89 g, 4.4 mmol) in dioxane (9 ml) under nitrogen cooled in an ice-bath was added 4M hydrogen chloride in dioxane (9 ml, 36 mmol). The mixture was stirred at ice-bath temperature for 1.5 hours, then at ambient temperature for three hours. The mixture was concentrated under reduced pressure to give a residual gum. The gum was suspended in methylene chloride (100 ml) and treated with 10N sodium hydroxide solution (0.45 ml). The mixture was stirred 20 minutes, dried (sodium carbonate and sodium sulfate), filtered, and the solvent evaporated under reduced pressure to give crude (+−)-trans-3-hydroxycyclopentanamine (0.43 g, 97%), colorless oil.

A solution of crude trans-3-hydroxycyclopentanamine (0.42 g, 4.2 mmol) and N-(benzyloxycarbonyl)succinimide (1.05 g, 0.42 mmol) in acetonitrile (40 ml) was stirred at ambient temperature under nitrogen for 18 hours. The mixture was concentrated under reduced pressure. The residue was taken up in ethyl acetate (150 ml), washed with water (3×75 ml), and brine (50 ml), dried (sodium sulfate), filtered, and the solvent evaporated under reduced pressure to give benzyl (trans-3-hydroxycyclopentyl)carbamate (0.97 g, 98%), as a white solid.

$^1$H NMR (CDCl3) 7.35 (5H, m), 5.09 (2H, s), 4.66 (1H, br s), 4.41 (1H, m), 4.25 (1H, m), 2.24 (1H, m), 2.05 (2H, m), 1.56-1.70 (2H, m), 1.32-1.45 (2H, m).

MS.: 236.3 (M+1).

Step 4: Benzyl (trans-3-{[tert-butyl(dimethyl)silyl]oxy}cyclopentyl)carbamate

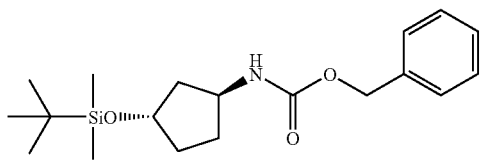

To a mixture of benzyl (trans-3-hydroxycyclopentyl)carbamate (0.95 g, 4.0 mmol) and diisopropylethylamine (1.05 ml, 0.78 g, 6.0 mmol) in methylene chloride (2.5 ml) under nitrogen was added tert-butyldimethylsilyl chloride (0.72 g, 4.8 mmol). The mixture was stirred at ambient temperature under nitrogen for 18 hours. The mixture was diluted with saturated sodium bicarbonate solution (5 ml), stirred 20 minutes, diluted with methylene chloride (5 ml), and the layers were separated. The aqueous layer was extracted with methylene chloride (5 ml). The combined organic layer was dried (sodium sulfate), filtered, and the solvent evaporated under reduced pressure to give a yellow oil (1.53 g). The oil was filtered through a pad of silica gel eluting with ethyl acetate:hexane (50:50) and the filtrate was concentrated to give benzyl (trans-3-{[tert-butyl(dimethyl)silyl]oxy}cyclopentyl)carbamate (1.35 g, 96%), as a pale yellow oil.

$^1$H NMR (CDCl3) 7.35 (5H, m), 5.09 (2H, s), 4.64 (1H, br s), 4.30 (1H, m), 4.21 (1H, m), 2.21 (1H, m), 2.00 (1H, m), 1.93 (1H, m), 1.57 (2H, m), 1.35 (1H, m), 0.86 (9H, s), 0.03 (6H, s).

MS.: 350.4 (M+1).

Step 5: Benzyl {trans-3-[2-(4-methylphenyl)ethoxy]cyclopentyl}carbamate

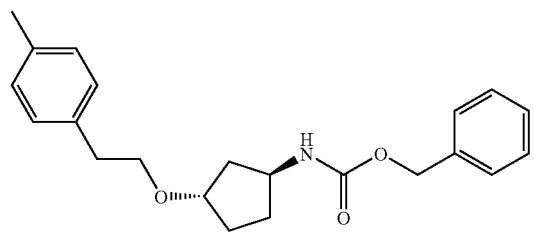

To a solution of ethyl 4-methylphenylacetate (0.89 g, 5.0 mmol) in dry methylene chloride (5 ml) cooled to −78° C. under nitrogen was added drop-wise 1.1 M di-isobutyl-aluminum hydride in toluene (4.5 ml, 5 mmol), keeping the internal temperature below −68° C. When the addition was complete, the reaction was quenched by drop-wise addition of methanol (5 ml), saturated potassium sodium tartrate solution (5 ml), and water (5 ml). The mixture was filtered through filter aid, the pad was washed with ethyl acetate (40 ml), and the filtrate layers were separated. The aqueous layer was extracted with ethyl acetate (40 ml). The combined ethyl acetate layers were washed with water (20 ml), and brine (20 ml), dried (sodium sulfate), filtered, and the solvent evaporated under reduced pressure to give 7.1 g of 4-methylphenylacetaldehyde as a volatile liquid: 1H NMR (CDCl3) 9.73 (1H, t, J 2.5 Hz), 7.17 (2H, m), 7.12 (2H, m), 3.64 (2H, d, J 2.5 Hz), 2.35 (3H, s). To a stirred mixture of benzyl (trans-3-{[tert-butyl(dimethyl)silyl]oxy}cyclopentyl)carbamate (524 mg, 1.5 mmol), triethylsilane (0.36 ml, 260 mg, 2.25 mmol), and bismuth tribromide (45 mg, 0.10 mmol), in anhydrous acetonitrile (7.5 ml), was added the freshly prepared 4-methylphenylacetaldehyde (460 mg, approx. 2.2 mmol) slowly, keeping the temperature at or below 25° C. After stirring for 4 h, the reaction was quenched with half-saturated sodium bicarbonate (30 ml) and ethyl acetate (25 ml). The mixture was filtered through filter aid, the pad was washed with ethyl acetate (3×8 ml), and the filtrate layers were separated. The organic layer was washed with one-fifth saturated brine (8 ml) and water (8 ml), dried (sodium sulfate), filtered, and the solvent evaporated under reduced pressure to give a heterogeneous oil (1.19 g). The oil was chromatographed on silica gel, eluting with ethyl acetate:hexane (5:95 increasing to 25:75) to give a white solid. The solid was triturated with ethyl acetate:hexane (20:80), filtered off and dried to give benzyl {trans-3-[2-(4-methylphenyl)ethoxy]cyclopentyl}carbamate (291 mg, 55%) as a white solid. A second crop was obtained from the mother liquor (34 mg, 6%).

¹H NMR (CDCl3) 7.35 (5H, m), 7.09 (4H, s), 5.08 (2H, s), 4.63 (1H, br s), 4.15 (1H, m), 3.95 (1H, m), 3.52 (2H, t, J 7 Hz), 2.84 (2H, t, J 7 Hz), 2.31 (3H, s), 2.12 (2H, m), 1.92 (1H, m), 1.68 (1H, m), 1.58 (1H, m), 1.36 (1H, m).

MS.: 354.4 (M+1).

Step 6:
trans-3-[2-(4-Methylphenyl)ethoxy]cyclopentanamine

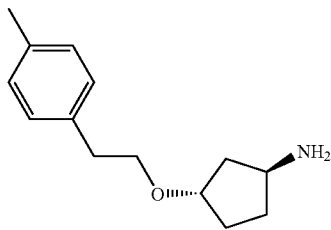

A mixture of benzyl {trans-3-[2-(4-methylphenyl)ethoxy]cyclopentyl}carbamate (291 mg, 0.82 g) and 5% palladium on carbon (150 mg) in ethanol (8 ml) was hydrogenated (hydrogen balloon) for three hours. The catalyst was removed by filtration through Celite. The filter cake was washed with ethanol (3×10 ml) and the filtrate was concentrated under reduced pressure to give an oil. The oil was filtered through a pad of silica gel eluting first with methanol: methylene chloride (10:90) to remove impurities, then with methanol: methylene chloride: conc. ammonium hydroxide (20:80:2), and the filtrate concentrated to give trans-3-[2-(4-methylphenyl)ethoxy]cyclopentanamine (154 mg, 86%), as a colorless oil.

¹H NMR (CDCl3) 7.09 (4H, s), 4.01 (1H, m), 3.53 (3H, m), 2.82 (2H, m), 2.31 (3H, s), 1.99 (3H, m), 1.61 (1H, m), 1.57 (2H, br s), 1.26 (1H, m).

MS.: 220.4 (M+1).

Step 7: N-[trans-3-[2-(4-Methylphenyl)ethoxy]cyclopentyl}-1H-pyrazolo[3,4-d]pyrimidin-4-amine

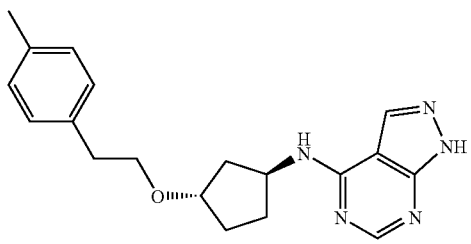

A mixture of trans-3-[2-(4-methylphenyl)ethoxy]cyclopentanamine (131 mg, 0.60 mmol), 4-chloro-1-(tetrahydropyran-2-yl)-1H-pyrazolo[3,4-d]pyrimidine (143 mg, 0.60 mmol), and N,N-diisopropylethylamine (0.21 ml, 1.20 mmol) in 2-propanol (6 ml) was heated to reflux under nitrogen overnight. The mixture was cooled and concentrated under reduced pressure. The residue was taken up in ethyl acetate (36 ml), washed with saturated sodium bicarbonate solution (12 ml), water (12 ml), and brine (12 ml), dried (sodium sulfate), and concentrated under reduced pressure. Chromatography over silica gel eluting with a gradient of 30%-80% ethyl acetate in hexane gave product (216 mg, 85%) as a white solid. The solid was taken up in methanol (4.5 ml) and 6N HCl (5 drops) and heated at reflux for 1.5 hours. The solution was cooled, diluted with 6N HCl (15 drops), and concentrated under reduced pressure to dryness to give product as the hydrochloride salt (172 mg, 100%), as a white solid.

1H NMR (DMSO-d6) 9.1-9.9 (1H, br s), 8.45 (2H, br s), 7.13 (2H, d, J 8 Hz), 7.08 (2H, d, J 8 Hz), 4.6 (1H, m), 4.07 (1H, m), 3.4-3.9 (2H, br s), 3.54 (2H, d, J 7 Hz), 2.75 (2H, d, J 7 Hz), 2.26 (3H, s), 2.14 (2H, m), 2.00 (1H, m), 1.88 (1H, m), 1.63 (2H, m).

MS.: 338.3 (M+1).

Racemic N-[trans-3-[2-(4-methylphenyl)ethoxy]cyclopentyl}-1H-pyrazolo[3,4-d]pyrimidin-4-amine hydrochloride was resolved by preparative chiral HPLC (Chiralcel OJ column, 5×50 mm, hexane: 2-propanol: diethylamine (40:60:0.1), 70 ml/min. The first enantiomer to elute was (+)-N-[trans-3-[2-(4-methylphenyl)ethoxy]cyclopentyl}-1H-pyrazolo[3,4-d]pyrimidin-4-amine (74 mg) as a white solid. Mass spec.: 338.3 (M+1). $[\alpha]_D$=+16° (c=0.214, methanol).

The second enantiomer to elute was (−)-N-[trans-3-[2-(4-methylphenyl)ethoxy]cyclopentyl}-1H-pyrazolo[3,4-d]pyrimidin-4-amine (70 mg) as a white solid. Mass spec.: 338.3 (M+1). $[\alpha]_D$=−17° (c=0.235, methanol).

EXAMPLE 75

N-[3-Fluoro-4-(2-phenylethoxy)cyclohexyl]-1H-pyrazolo [3,4-d]pyrimidin-4-amine hydrochloride The synthesis of N-[3-Fluoro-4-(2-phenylethoxy)cyclohexyl]-1H-pyrazolo[3,4-d]pyrimidin-4-amine hydrochloride is summarized below:

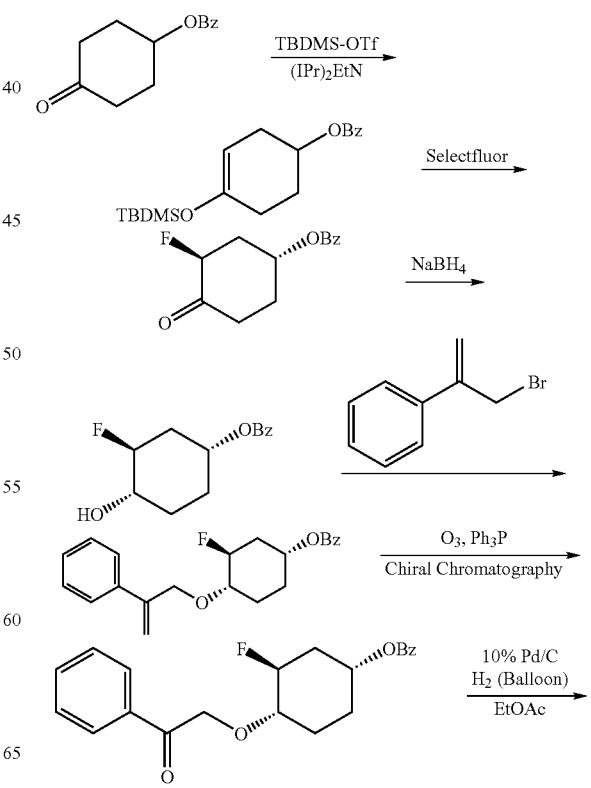

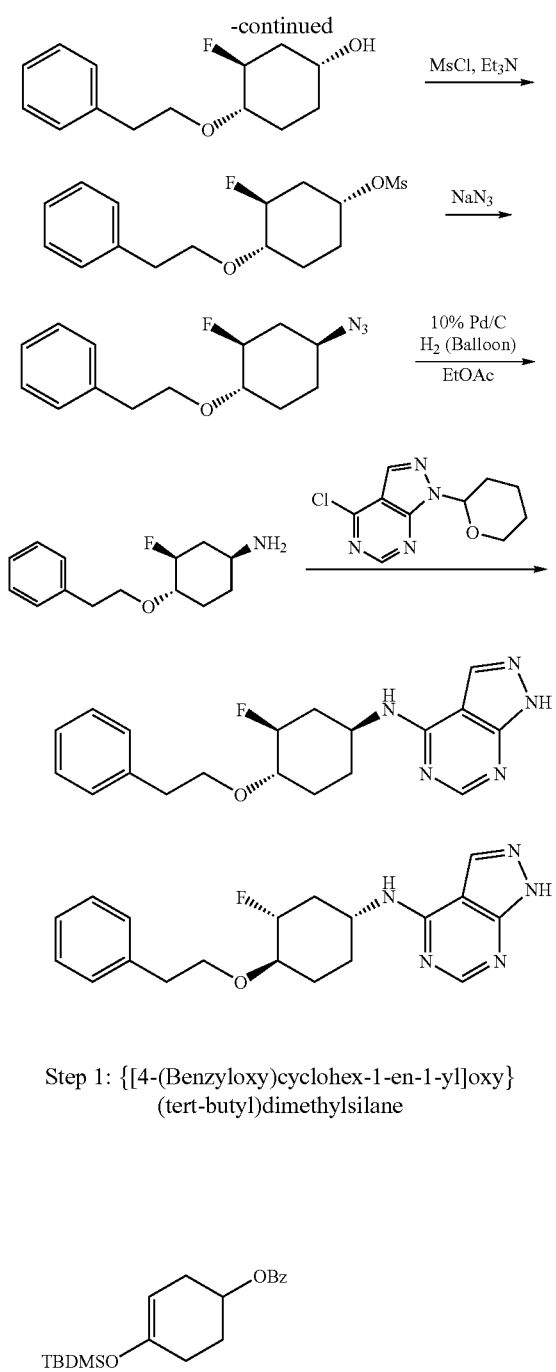

Step 1: {[4-(Benzyloxy)cyclohex-1-en-1-yl]oxy}(tert-butyl)dimethylsilane

A methylene chloride (200 mL) solution of 4-oxocyclohexyl benzoate [*Macromolecules* 2000, 33, 4619] (17.2 g, 84.5 mmol) in N,N-diisopropylethylamine (29.4 mL, 169 mmol) was cooled in an ice bath under nitrogen. A methylene chloride (50 mL) solution of tert-butyldimethylsilyl trifluormethanesulfonate (20.3 mL, 88.7 mmol) was added dropwise over 0.5 h. After warming to room temperature the contents of the reaction flask were poured into water. The organic layer was separated, dried with anhydrous magnesium sulfate, filtered and concentrated under reduced pressure. Flash column chromatography (hexane:ethyl acetate, 95:5) gave a pale oil (23.2 g, 86% yield).

Step 2: 4-(Benzyloxy)-2-fluorocyclohexanone

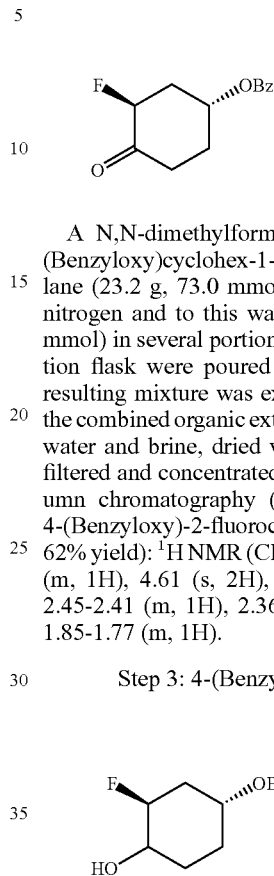

A N,N-dimethylformamide (150 mL) solution of {[4-(Benzyloxy)cyclohex-1-en-1-yl]oxy}(tert-butyl)dimethylsilane (23.2 g, 73.0 mmol) was cooled in an ice bath under nitrogen and to this was added Selectfluor™ (51.6 g, 146 mmol) in several portions. After 1 h the contents of the reaction flask were poured into 5% sodium bicarbonate. The resulting mixture was extracted with ethyl acetate (4×) and the combined organic extracts were washed successively with water and brine, dried with anhydrous magnesium sulfate, filtered and concentrated under reduced pressure. Flash column chromatography (hexane:ethyl acetate, 80:20) gave 4-(Benzyloxy)-2-fluorocyclohexanone as a pale oil (10.0 g, 62% yield): $^1$H NMR (CDCl$_3$) δ 7.39-7.30 (m, 5H), 5.36-5.19 (m, 1H), 4.61 (s, 2H), 4.02 (m, 1H), 2.81-2.73 (m, 2H), 2.45-2.41 (m, 1H), 2.36-2.30 (m, 1H), 2.05-1.88 (m, 1H), 1.85-1.77 (m, 1H).

Step 3: 4-(Benzyloxy)-2-fluorocyclohexanol

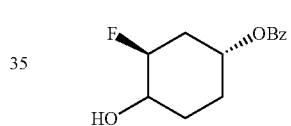

A methanol (200 mL) solution of 4-(Benzyloxy)-2-fluorocyclohexanone (6.46 g, 29.1 mmol) was cooled in and ice bath under nitrogen. Sodium borohydride (1.66 g, 43.6 mmol) was added and the reaction aged 0.5 h. Hydrochloric acid (1 N) was slowly added after which methanol was removed under reduced pressure. Water was added and the resulting mixture was extracted with ethyl acetate (4×) and the combined organic extracts were washed with brine, dried with anhydrous magnesium sulfate, filtered and concentrated under reduced pressure to give 4-(Benzyloxy)-2-fluorocyclohexanol as a pale oil (6.05 g, 93% yield).

Step 4: [1-({[4-(Benzyloxy)-2-fluorocyclohexyl]oxy}methyl)vinyl]benzene

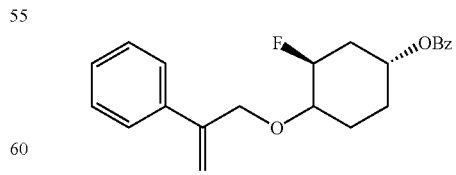

To a N,N-dimethylformamide (30 mL), tetrahydrofuran (30 mL) solution of 4-(Benzyloxy)-2-fluorocyclohexanol (4.28 g, 19.1 mmol) under nitrogen was added 60% sodium hydride (1.5 g, 37.5 mmol). The resulting mixture was heated at 60° C. for 0.5 h then [1-bromoethyl)vinyl]benzene [*J. Am.*

*Chem. Soc.* 1954, 76, 2705.] (4.88 g, 24.8 mmol) was added. After 0.5 h the contents of the reaction flask were poured into 5% sodium bicarbonate. The resulting mixture was extracted with ethyl acetate (3x) and the combined organic extracts were washed with brine, dried with anhydrous magnesium sulfate, filtered and concentrated under reduced pressure. Flash column chromatography (hexane:ethyl acetate, 95:5) gave [1-({[4-(Benzyloxy)-2-fluorocyclohexyl]oxy}methyl)vinyl]benzene as a pale oil (1.65 g, 25% yield): $^1$H NMR (CDCl$_3$) δ 7.50-7.44 (m, 2H), 7.36-7.24 (m, 8H), 5.52 (s, 1H), 5.38 (s, 1H), 4.87-4.72 (m, 1H), 4.55-4.45 (m, 4H), 3.75-3.73 (m, 1H), 3.56-3.52 (m, 1H), 2.30-2.15 (m, 1H), 1.90-1.75 (m, 4H), 1.58-1.49 (m, 1H).

Step 5: 2-{[4-(Benzyloxy)-2-fluorocyclohexyl]oxy}-1-phenylethanone (−) and (+)

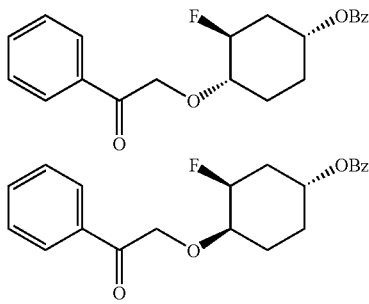

A methanol (300 mL) solution of [1-({[4-(Benzyloxy)-2-fluorocyclohexyl]oxy}methyl)vinyl]benzene (2.02 g, 5.95 mmol) was cooled to −70° C. Ozone gas was bubbled through the solution until a blue color appeared. The solution was purged with nitrogen then a solution of triphenylphosphine (2.34 g, 8.92 mmol) in methylene chloride (100 mL) was added. Contents of the reaction flask were warmed to room temperature and the solvent was removed under reduced pressure. The remaining residue was subjected to flash column chromatography (hexane:ethyl acetate, 90:10) to give 2-{[4-(Benzyloxy)-2-fluorocyclohexyl]oxy}-1-phenylethanone as a colorless oil (1.68 g, 83% yield).

Chiral preparative chromatography of 2-{[4-(Benzyloxy)-2-fluorocyclohexyl]oxy}-1-phenylethanone (6.75 g):

| Column: | Chiralcel OD |
|---|---|
| Size: | 5 x 50 cm, 20µ |
| Method: | Isocratic, hexane isopropanol 40:60 with 0.1% N,N-diisopropylamine |
| Detector: | 235 nm |

Fractions containing the first eluting enantiomer were evaporated under reduced pressure to give the (−) enantiomer (2.70 g, 40% yield).

$[\alpha]_D$ (MeOH)−8.1°, (c=0.037)

Fractions containing the second eluting enantiomer were evaporated under reduced pressure to give the (+) enantiomer (3.17 g, 47% yield).

$[\alpha]_D$ (MeOH)+9.8°, (c=0.035)

Step 6: 3-Fluoro-4-(2-phenylethoxy)cyclohexanol

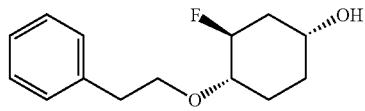

To an ethyl acetate (100 mL) solution of (−) 2-{[4-(Benzyloxy)-2-fluorocyclohexyl]oxy}-1-phenylethanone (1.44 g, 4.18 mmol) was added 10% palladium on carbon (0.200 g). The resulting mixture was hydrogenated using a balloon. After 20 h the contents of the reaction flask were filtered through celite® and the filtrate evaporated under reduced pressure. Flash column chromatography (hexane:ethyl acetate, 60:40) gave 3-Fluoro-4-(2-phenylethoxy)cyclohexanol as a colorless oil (0.918 g, 92% yield).

Step 7: 3-Fluoro-4-(2-phenylethoxy)cyclohexyl methanesulfonate

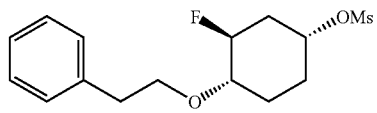

A methylene chloride (10 mL) solution of 3-Fluoro-4-(2-phenylethoxy)cyclohexanol (0.450 g, 1.89 mmol) in N,N-diisopropylethylamine (0.688 mL, 3.96 mmol) was cooled in an ice bath under nitrogen. Methanesulfonyl chloride (0.154 mL, 1.98 mmol) was added dropwise to the reaction solution. After 0.5 h the contents of the reaction flask were washed with 5% potassium bisulfate. The aqueous layer was extracted (2x) with methylene chloride and the combined organic portions dried with anhydrous magnesium sulfate, filtered and evaporated under reduced pressure. Flash column chromatography (hexane:ethyl acetate, 60:40) gave 3-Fluoro-4-(2-phenylethoxy)cyclohexyl methanesulfonate as a colorless oil (0.597 g, 100% yield).

Step 8: 4-Azido-2-fluorocyclohexyl 2-phenylethyl ether

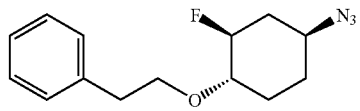

Sodium azide (0.500 g, 7.69 mmol) was added to a N,N-dimethylformamide (10 mL) solution of 3-Fluoro-4-(2-phenylethoxy)cyclohexyl methanesulfonate (0.597 g, 1.89 mmol) under nitrogen. The resulting mixture was heated at 50° C. for 24 h, then cooled and poured into saturated sodium bicarbonate. The aqueous mixture was extracted with ethyl acetate (3x) and the combined organic extracts were washed with brine, dried with anhydrous magnesium sulfate, filtered and concentrated under reduced pressure. Flash column chromatography (hexane:ethyl acetate, e 90:10) gave 4-Azido-2-fluorocyclohexyl 2-phenylethyl ether as a colorless oil (0.355 g, 71% yield).

Step 9:
[3-Fluoro-4-(2-phenylethoxy)cyclohexyl]amine

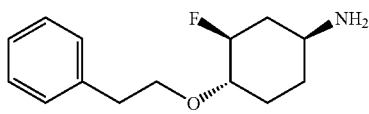

To an ethyl acetate (80 mL) solution of 4-Azido-2-fluorocyclohexyl 2-phenylethyl ether (0.677 g, 2.57 mmol) was added 10% palladium on carbon (0.200 g). The resulting mixture was hydrogenated using a balloon. After 1 h the contents of the reaction flask were filtered through Celite® and the filtrate evaporated under reduced pressure. Flash column chromatography (methylene chloride:methanol:ammonium hydroxide, 90:10:1) gave [3-Fluoro-4-(2-phenylethoxy)cyclohexyl]amine as a waxy oil (0.519 g, 85% yield).

Step 10: N-[3-Fluoro-4-(2-phenylethoxy)cyclohexyl]-1H-pyrazolo[3,4-d]pyrimidin-4-amine hydrochloride

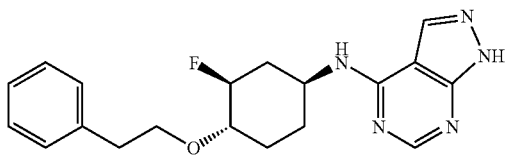

A 2-propanol (15 mL) solution of [3-Fluoro-4-(2-phenylethoxy)cyclohexyl]amine (0.776 g, 3.27 mmol), pyran-protected chloropyrazolopyrimidine, (0.856 g, 3.59 mmol) and diisopropylethylamine (4.50 mL, 26.2 mmol) was heated at reflux under nitrogen for 24 h. Contents of the reaction flask were cooled to room temperature and 6 N hydrochloric acid (6 mL) was added and the solution heated to reflux for 0.25 h, cooled and the organic solvent removed under reduced pressure. Water was added and the pH of the solution adjusted to 7. The aqueous solution was extracted with ethyl acetate (5×), and the combined organics dried with anhydrous magnesium sulfate, filtered and evaporated under reduced pressure. Flash column chromatography (methylene chloride:methanol:ammonium hydroxide, 97:3:0.3) gave the title compound N-[3-Fluoro-4-(2-phenylethoxy)cyclohexyl]-1H-pyrazolo[3,4-d]pyrimidin-4-amine hydrochloride (0.984 g, 85% yield) as a white solid (free base). Treatment of an ice cooled 2-propanol solution of the free base with hydrogen chloride/2-propanol afforded after isolation by filtration, the hydrochloride salt of N-[3-Fluoro-4-(2-phenylethoxy)cyclohexyl]-1H-pyrazolo[3,4-d]pyrimidin-4-amine hydrochloride: mp =275-285° C. (decomposes); $^1$H NMR (CD$_3$OD) δ 8.51 (s, br, 2H), 7.25-7.18 (m, 5H), 4.48 (m, 1H), 4.35 (m, 1H), 3.85 (m, 2H), 3.48 (m, 1H), 2.88 (m, 2H), 2.48 (m, 1H), 2.10-2.00 (m, 2H), 1.75 (m, 1H), 1.53 (m, 1H), 1.38 (m, 1H); HRMS (ESI) m/z 356.1882 [(M+H)$^+$; calcd for C$_{19}$H$_{23}$FN$_5$O: 356.1881].

Step 11: N-[3-Fluoro-4-(2-phenylethoxy)cyclohexyl]-1H-pyrazolo[3,4-d]pyrimidin-4-amine hydrochloride

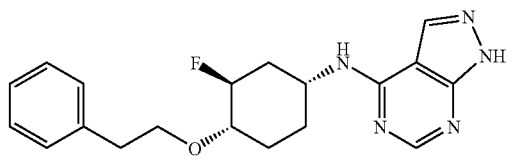

The title compound (the enantiomer of the compound made in Step 10), was prepared from ketone 2-{[4-(Benzyloxy)-2-fluorocyclohexyl]oxy}-1-phenylethanone (+) following the identical reaction sequence described in the above Steps, to give N-[3-Fluoro-4-(2-phenylethoxy)cyclohexyl]-1H-pyrazolo[3,4-d]pyrimidin-4-amine hydrochloride. mp=275-285° C. (decomposes); $^1$H NMR (CD$_3$OD) δ 8.24 (s, 1H), 8.09 (s, 1H), 7.30-7.16 (m, 5H), 4.60-4.37 (m, 1 H), 4.23 (m, 1H), 3.92-3.78 (m, 2H), 3.48-3.38 (m, 1H), 2.88 (m, 2H), 2.52-2.40 (m, 1H), 2.13-2.05 (m, 2H), 1.70-1.57 (m, 1H), 1.50-1.29 (m, 2H); HRMS (ESI) m/z 356.1887 [(M+H)$^+$; calcd for C$_{19}$H$_{23}$FN$_5$O: 356.1881].

EXAMPLE 76

N-{3-fluoro-4-[2-fluoro-2-phenylethoxy]cyclohexyl}-1H-pyrazolo[3,4-d]pyrimidin-4-amine The synthesis of N-{3-fluoro-4-[2-fluoro-2-phenylethoxy]cyclohexyl}-1H-pyrazolo[3,4-d]pyrimidin-4-amine is summarized below:

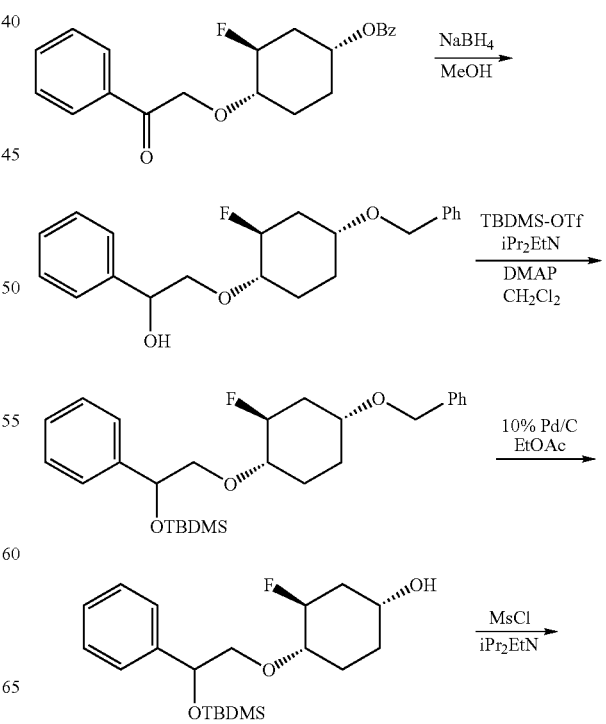

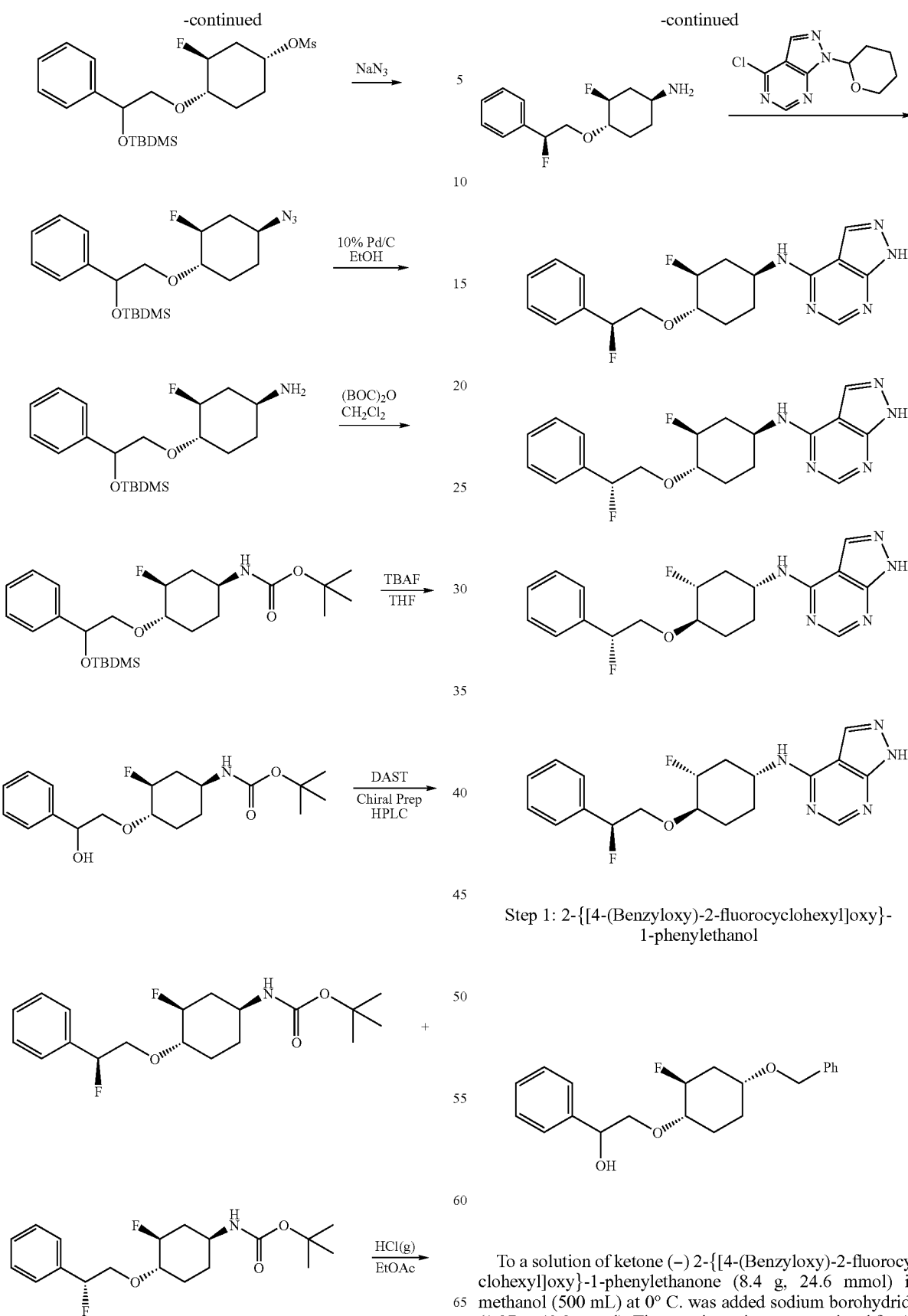
Step 1: 2-{[4-(Benzyloxy)-2-fluorocyclohexyl]oxy}-1-phenylethanol
To a solution of ketone (−) 2-{[4-(Benzyloxy)-2-fluorocyclohexyl]oxy}-1-phenylethanone (8.4 g, 24.6 mmol) in methanol (500 mL) at 0° C. was added sodium borohydride (1.87 g, 49.2 mmol). The reaction mixture was stirred for 15 min and then carefully quenched by the dropwise addition of 1 M HCl (20 mL). The mixture was concentrated to remove the methanol and then diluted with dichloromethane and water. The layers were separated and the aqueous was extracted twice with dichloromethane. The combined organic layers were dried over anhydrous magnesium sulfate, filtered and concentrated to give 2-{[4-(Benzyloxy)-2-fluorocyclohexyl]oxy}-1-phenylethanol (8.46 g, 100%) as a clear oil which was used with no further purification.

Step 2: (2-{[4-(Benzyloxy)-2-fluorocyclohexyl]oxy}-1-phenylethoxy)(tert-butyl)dimethylsilane

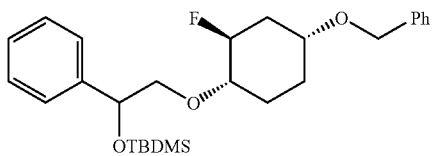

To a solution of 2-{[4-(Benzyloxy)-2-fluorocyclohexyl]oxy}-1-phenylethanol (8.46 g, 24.6 mmol) in dichloromethane (100 mL) at 0° C. was added diisopropylethylamine (17.1 mL, 98.8 mmol) and TBSOTf (13.0 mL, 49.4 mmol). The reaction mixture was stirred for 5 min and then poured into water. The layers were separated and the aqueous extracted with dichloromethane (3×). The combined organic layers were washed with water and brine, dried over Na$_2$SO$_4$, filtered and concentrated. Purification by flash column chromatography (5% ethyl acetate in hexanes) gave (2-{[4-(Benzyloxy)-2-fluorocyclohexyl]oxy}-1-phenylethoxy)(tert-butyl)dimethylsilane (11.3 g, 100% yield) as a clear oil.

Step 3: 4-(2-{[tert-Butyl(dimethyl)silyl]oxy}-2-phenylethoxy)-3-fluorocyclohexanol

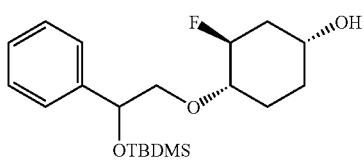

To a solution of (2-{[4-(Benzyloxy)-2-fluorocyclohexyl]oxy}-1-phenylethoxy)(tert-butyl)dimethylsilane (11.3 g, 24.7 mmol) in ethyl acetate (200 mL) was added 10% Pd/C (1.0 g) at room temperature. The reaction mixture was stirred under balloon pressure hydrogen for 4 h, filtered and concentrated. Purification by silica gel chromatography (hexane: ethyl acetate 60:40) gave 4-(2-{[tert-Butyl(dimethyl)silyl]oxy}-2-phenylethoxy)-3-fluorocyclohexanol (8.46 g, 93% yield) as a clear oil.

Step 4: 4-(2-{[tert-Butyl(dimethyl)silyl]oxy}-2-phenylethoxy)-3-fluorocyclohexyl methanesulfonate

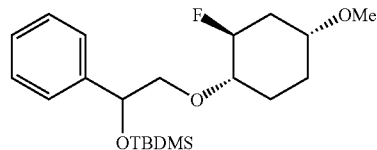

To a solution of 4-(2-{[tert-Butyl(dimethyl)silyl]oxy}-2-phenylethoxy)-3-fluorocyclohexanol (8.46 g, 22.9 mmol) in dichloromethane (100 mL) at 0° C. was added methanesulfonyl chloride (2.49 mL, 32.1 mmol) and diisopropylethylamine (11.1 mL, 64.1 mmol). The reaction mixture was stirred for 1 min, diluted with dichloromethane and washed with 5% potassium bisulfate. The layers were separated and the aqueous extracted with dichloromethane (3×). The combined organic layers were washed with water and brine, dried over Na$_2$SO$_4$, filtered and concentrated. Purification by flash column chromatography (hexane: ethyl acetate 70:30) gave 4-(2-{[tert-Butyl(dimethyl)silyl]oxy}-2-phenylethoxy)-3-fluorocyclohexyl methanesulfonate (9.77 g, 100% yield) as a clear oil.

Step 5: (2-{[4-Azido-2-fluorocyclohexyl]oxy}-1-phenylethoxy)(tert-butyl)dimethylsilane

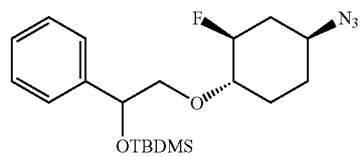

To a solution of mesylates 4-(2-{[tert-Butyl(dimethyl)silyl]oxy}-2-phenylethoxy)-3-fluorocyclohexyl methanesulfonate (9.77 g, 21.9 mmol) in dimethylformamide (100 mL) was added sodium azide (6.93 g, 110 mmol). The reaction mixture was heated to 90° C. and stirred for 2 h. After cooling, the reaction mixture was poured into saturated NaHCO$_3$ (aq). The mixture was extracted with ethyl acetate (4×), dried over anhydrous magnesium sulfate, filtered and concentrated. Purification by flash column chromatography (gradient elution: hexanes to 20% ethyl acetate in hexanes) gave (2-{[4-Azido-2-fluorocyclohexyl]oxy}-1-phenylethoxy)(tert-butyl)dimethylsilane (6.0 g) as a clear oil.

Step 6: 4-(2-{[tert-Butyl(dimethyl)silyl]oxy}-2-phenylethoxy)-3-fluorocyclohexanamine

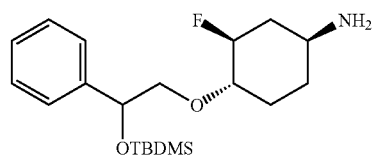

An ethanol (50 mL) solution of (2-{[4-Azido-2-fluorocyclohexyl]oxy}-1-phenylethoxy)(tert-butyl)dimethylsilane (6.0 g, 15.3 mmol) was treated with 10% palladium on carbon and hydrogenated using a balloon. After 1 h the contents of the reaction flask were filtered through Celite® and the filtrate evaporated under reduced pressure. Flash column chromatography (methylene chloride:methanol:ammonium hydroxide 92:8:0.8) gave 4-(2-{[tert-Butyl(dimethyl)silyl]oxy}-2-phenylethoxy)-3-fluorocyclohexanamine as a pale oil (4.54 g, 57% over two steps).

Step 7: tert-butyl 4-(2-{[tert-butyl(dimethyl)silyl]oxy}-2-phenylethoxy)-3-fluorocyclohexylcarbamate

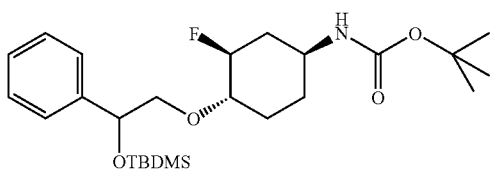

To a solution of amines 4-(2-{[tert-Butyl(dimethyl)silyl]oxy}-2-phenylethoxy)-3-fluorocyclohexanamine (4.60 g, 12.5 mmol) in dichloromethane (50 mL) at 0° C. was added di-tert-butyl dicarbonate (3.27 g, 15.0 mmol). The reaction mixture was stirred for 1 h, diluted with dichloromethane and washed with 5% potassium bisulfate. The layers were separated and the aqueous extracted with dichloromethane (3×). The combined organic layers were dried over anhydrous magnesium sulfate, filtered and concentrated. Purification by flash column chromatography (hexane: ethyl acetate 90:10) gave tert-butyl 4-(2-{[tert-butyl(dimethyl)silyl]oxy}-2-phenylethoxy)-3-fluorocyclohexylcarbamate (5.83 g, 100% yield) as a clear oil.

Step 8: tert-Butyl 3-fluoro-4-(2-hydroxy-2-phenylethoxy)cyclohexylcarbamate

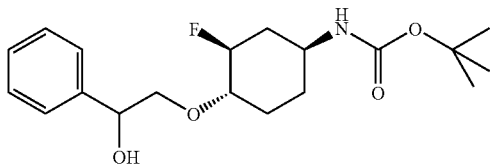

To a solution of tert-butyl 4-(2-{[tert-butyl(dimethyl)silyl]oxy}-2-phenylethoxy)-3-fluorocyclohexylcarbamate (5.83 g, 12.5 mmol) in THF (100 mL) was added tetrabutylammonium fluoride (25 mL, 25 mmol, 1M in THF) and the reaction mixture was stirred at room temperature for 8 h. The mixture was extracted with ethyl acetate (4×), and the combined organics washed with brine, dried over anhydrous magnesium sulfate, filtered and concentrated. Purification by flash column chromatography (hexane: ethyl acetate 80:20 then 60:40) gave tert-Butyl 3-fluoro-4-(2-hydroxy-2-phenylethoxy)cyclohexylcarbamate (4.33 g) as a white solid.

Step 9: tert-butyl {3-fluoro-4-[2-fluoro-2-phenylethoxy]cyclohexyl}carbamate (2 enantiomers)

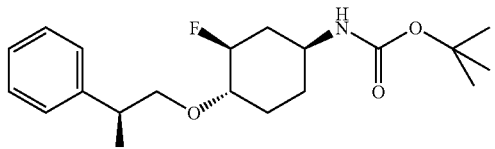

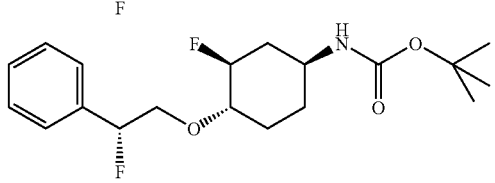

A methylene chloride (20 mL) solution of (diethylamino)sulfur trifluoride (0.198 mL, 1.50 mmol) was cooled under nitrogen to −70 C. A solution of tert-Butyl 3-fluoro-4-(2-hydroxy-2-phenylethoxy)cyclohexylcarbamate (0.408 g, 1.15 mmol) in methylene chloride (10 mL) was added in a fast stream. After 5 min. the reaction was quenched with water and warmed to room temperature. The mixture was extracted with dichloromethane (3×), the combined organic layers dried over anhydrous magnesium sulfate, filtered and concentrated. Purification by flash column chromatography (hexane: ethyl acetate 80:20) gave a white solid, which was a diastereomeric mixture of tert-butyl {3-fluoro-4-[2-fluoro-2-phenylethoxy]cyclohexyl}carbamate and tert-butyl {3-fluoro-4-[2-fluoro-2-phenylethoxy]cyclohexyl}carbamate (0.330 g, 77% yield).

Chiral preparative chromatography for separation of diasteromers (0.320 g):

| | |
|---|---|
| Column: | Chiralcel OJ |
| Size: | 5 × 50 cm, 20μ |
| Method: | Isocratic, hexane isopropanol 80:20 with 0.1% N,N-diisopropylamine |
| Detector: | 220 nm |

Fractions containing the second eluting diastereomer were evaporated under reduced pressure to give tert-butyl {3-fluoro-4-[2-fluoro-2-phenylethoxy]cyclohexyl}carbamate (0.155 g, 48% yield): $^1$H NMR (CDCl$_3$) δ 7.40 (m, 5H), 5.70-5.50 (m, 1H), 4.62-4.40 (m, 2H), 4.05-3.72 (m, 1H), 3.84-3.73 (m, 1H), 3.65-3.39 (m, 2H), 2.43-2.29 (m, 1H), 2.05-1.90 (m, 2H), 1.55-1.33 (m, 11H), 1.30-1.15 (m, 1H); HRMS (ESI) m/z 378.1842 [(M+Na)$^+$; calcd for C$_{19}$H$_{27}$F$_2$NNaO$_3$: 378.1851].

Fractions containing the first eluting diastereomer were evaporated under reduced pressure to give tert-butyl {3-fluoro-4-[2-fluoro-2-phenylethoxy]cyclohexyl}carbamate (0.150 g, 47%): $^1$H NMR (CDCl$_3$) δ 7.40 (m, 5H), 5.68-5.53 (m, 1H), 4.60-4.40 (m, 2H), 3.95-3.84 (m, 2H), 3.65-3.52 (m, 1H), 3.48-3.39 (m, 1H), 2.45-2.32 (m, 1H), 2.11-1.93 (m, 2H), 1.50-1.35 (m, 11H), 1.30-1.15 (m, 1H); HRMS (ESI) m/z 378.1840 [(M+Na)$^+$; calcd for C$_{19}$H$_{27}$F$_2$NNaO$_3$: 378.1851].

Step 10: {3-fluoro-4-[2-fluoro-2-phenylethoxy]cyclohexyl}amine hydrochloride

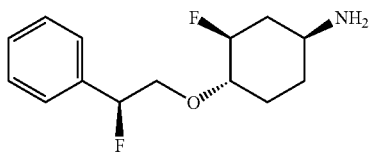

tert-butyl {3-fluoro-4-[2-fluoro-2-phenylethoxy]cyclohexyl}carbamate (first enantiomer) (0.150 g, 47%) was dissolved in ethyl acetate (15 mL) and the solution was cooled to 0° C. Hydrogen chloride (g) was bubbled through the solution for 2 min. After 1 h the contents of the reaction flask were concentrated to provide {3-fluoro-4-[2-fluoro-2-phenylethoxy]cyclohexyl}amine hydrochloride, which was used with no further purification. HRMS (ESI) m/z 256.1507 [(M+H)$^+$; calcd for $C_{14}H_{20}F_2NO$: 256.1507].

Step 11: N-{3-fluoro-4-[2-fluoro-2-phenylethoxy]cyclohexyl}-1H-pyrazolo[3,4-d]pyrimidin-4-amine

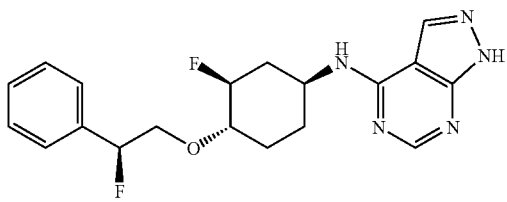

Using {3-fluoro-4-[2-fluoro-2-phenylethoxy]cyclohexyl}amine hydrochloride (0.085 g, 0.292 mmol), the title compound was prepared using a procedure like that described in Step 10, Example 75, to give N-{3-fluoro-4-[2-fluoro-2-phenylethoxy]cyclohexyl}-1H-pyrazolo[3,4-d]pyrimidin-4-amine (0.080 g, 74%): mp=207-208° C.; $^1$H NMR (CD$_3$OD) δ 8.23 (s, 1H), 8.09 (s, 1H), 7.44-7.30 (m, 5H), 5.66-5.51 (m, 1H), 4.64-4.42 (m, 1H), 4.23 (m, 1H), 4.12-4.01 (m, 1H), 3.90-3.79 (m, 1H), 3.60-3.48 (m, 1H), 2.47 (m, 1H), 2.10 (m, 2H), 1.72-1.58 (m, 1H), 1.52-1.36 (m, 2H); HRMS (ESI) m/z 374.1769 [(M+H)$^+$; calcd for $C_{19}H_{22}F_2N_5O$: 374.1787].

Step 12: N-{3-fluoro-4-[2-fluoro-2-phenylethoxy]cyclohexyl}-1H-pyrazolo[3,4-d]pyrimidin-4-amine

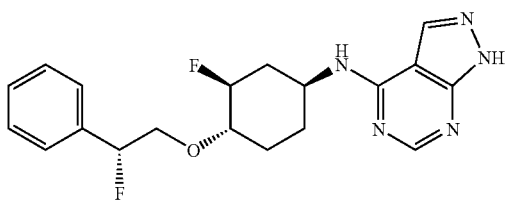

Beginning with tert-butyl {3-fluoro-4-[2-fluoro-2-phenylethoxy]cyclohexyl}carbamate (second enantiomer) and using a sequence like that described in Step 11, the title compound (0.051 g, 46% for two steps) was prepared: $^1$H NMR (CD$_3$OD) δ 8.24 (s, 1H), 8.09 (s, 1H), 7.44-7.30 (m, 5H), 5.67-5.52 (m, 1H), 4.64-4.42 (m, 1H), 4.24 (m, 1H), 3.99-3.85 (m, 2H), 3.58-3.48 (m, 1H), 2.52-2.43 (m, 1H), 2.19-2.05 (m, 2H), 1.72-1.58 (m, 1H), 1.52-1.36 (m, 2H): mp=204-205° C.; HRMS (ESI) m/z 374.1779 [(M+H)$^+$; calcd for $C_{19}H_{22}F_2N_5O$: 374.1787].

Step 13: N-{3-fluoro-4-[2-fluoro-2-phenylethoxy]cyclohexyl}-1H-pyrazolo[3,4-d]pyrimidin-4-amine

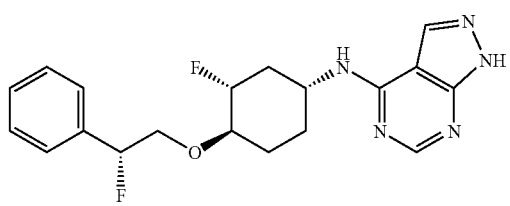

Prepared from (+) 2-{[4-(Benzyloxy)-2-fluorocyclohexyl]oxy}-1-phenylethanone according to the procedure in Step 11. mp=213-215° C.; MS m/z 374.4 [(M+H)$^+$; calcd for $C_{19}H_{22}F_2N_5O$: 374].

Step 14: N-{(3-fluoro-4-[2-fluoro-2-phenylethoxy]cyclohexyl}-1H-pyrazolo[3,4-d]pyrimidin-4-amine

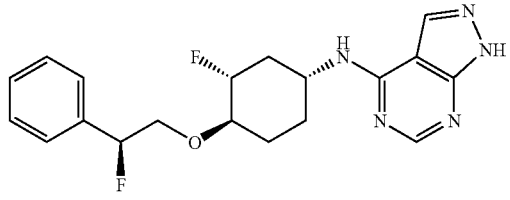

Prepared from (+) 2-{[4-(Benzyloxy)-2-fluorocyclohexyl]oxy}-1-phenylethanone according to the procedure in Step 12. mp=209-211° C.; MS m/z 374.4 [(M+H)$^+$; calcd for $C_{19}H_{22}F_2N_5O$: 374].

EXAMPLE 77

N-[4-(2,2-difluoro-2-phenylethoxy)-3-fluorocyclohexyl]-1H-pyrazolo[3,4-d]pyrimidin-4-amine The preparation N-[4-(2,2-difluoro-2-phenylethoxy)-3-fluorocyclohexyl]-1H-pyrazolo[3,4-d]pyrimidin-4-amine of is summarized below:

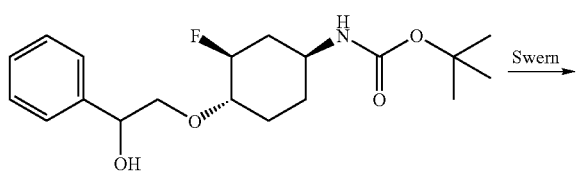

-continued

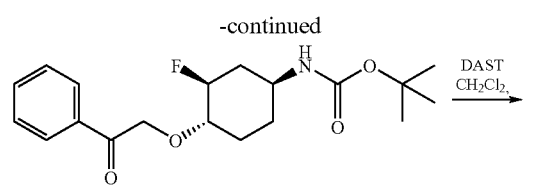

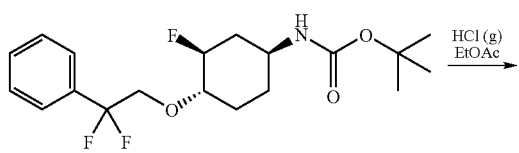

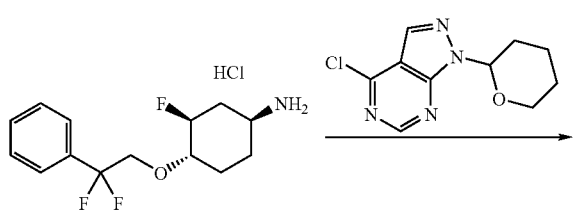

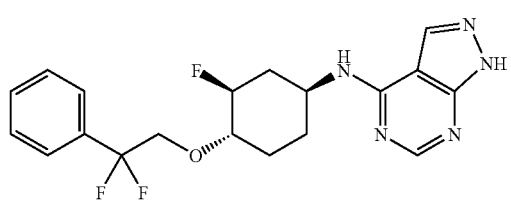

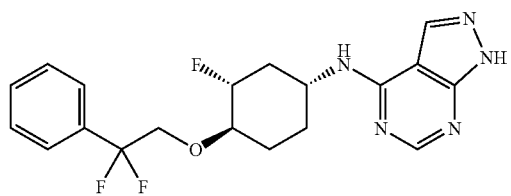

Step 1: tert-Butyl 3-fluoro-4-(2-oxo-2-phenylethoxy) cyclohexylcarbamate

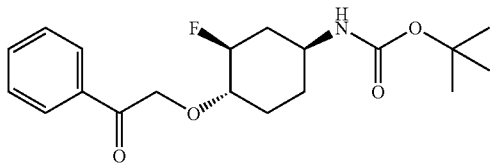

A solution of oxalyl chloride (0.054 mL, 0.623 mmol) in dichloromethane (10 mL) was cooled to −78° C. Dimethylsulfoxide (0.088 mL, 1.36 mmol) was added dropwise and the reaction mixture was stirred for 5 min. (−) tert-Butyl 3-fluoro-4-(2-hydroxy-2-phenylethoxy)cyclohexylcarbamate (200 mg, 0.567 mmol) was then added as a solution in dichloromethane (1 mL). After 5 min of stirring, diisopropylethylamine (0.494 mL, 2.84 mmol) was added in one portion, the reaction mixture was warmed to room temperature and stirred for 2 h. The reaction mixture was then poured saturated sodium bicarbonate, the layers were separated and the aqueous extracted (4×) with dichloromethane. The combined organic layers were dried with anhydrous magnesium sulfate, filtered and concentrated. Purification by flash column chromatography (hexane: ethyl acetate) gave tert-Butyl 3-fluoro-4-(2-oxo-2-phenylethoxy)cyclohexylcarbamate (175 mg, 88% yield) as a white solid.

Step 2: tert-Butyl 4-(2,2-difluoro-2-phenylethoxy)-3-fluorocyclohexylcarbamate

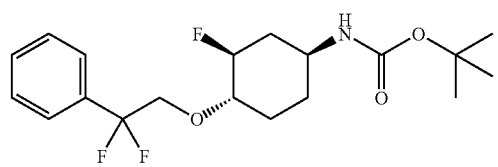

tert-Butyl 3-fluoro-4-(2-oxo-2-phenylethoxy)cyclohexylcarbamate (175 mg, 0.498 mmol) was dissolved in dichloromethane (0.500 mL) and the solution was cooled to 0° C. Diethylaminosulfur trifluoride (0.500 mL) was added, the reaction mixture was warmed to room temperature and stirred to 24 h. The reaction mixture was then carefully added to ice, diluted with water and extracted three times with dichloromethane. The combined organics were dried over anhydrous magnesium sulfate, filtered and concentrated. Purification by flash chromatography (hexane: ethyl acetate 95:5 then 90:10 then 80:20) gave tert-Butyl 4-(2,2-difluoro-2-phenylethoxy)-3-fluorocyclohexylcarbamate (85 mg, 46% yield) as a white solid.

Step 3: 4-(2,2-Difluoro-2-phenylethoxy)-3-fluorocyclohexanamine hydrochloride

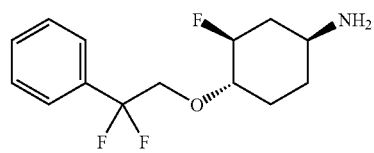

Protected amine tert-Butyl 4-(2,2-difluoro-2-phenylethoxy)-3-fluorocyclohexylcarbamate (85 mg, 0.228 mmol) was dissolved in ethyl acetate (15 mL) and the solution was cooled to 0° C. Hydrogen chloride (g) was bubbled through the solution for 2 min. After 1 h the contents of the reaction flask were concentrated to provide 4-(2,2-Difluoro-2-phenylethoxy)-3-fluorocyclohexanamine hydrochloride which was used with no further purification.

Step 4: N-[4-(2,2-difluoro-2-phenylethoxy)-3-fluoro-cyclohexyl]-1H-pyrazolo[3,4-d]pyrimidin-4-amine

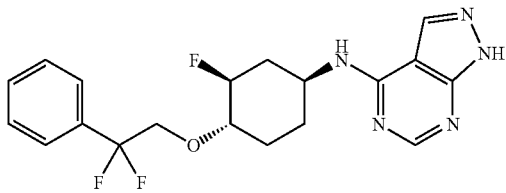

To a solution of 4-(2,2-Difluoro-2-phenylethoxy)-3-fluorocyclohexanamine hydrochloride (70 mg, 0.228 mmol) in 2-propanol (10 mL) was added sodium carbonate (109 mg, 1.02 mmol) and protected chloro-pyrazolopyrimidine (65 mg, 0.274 mmol). The reaction mixture was heated to 90° C. and stirred for 24 h. The reaction mixture was cooled, evaporated under reduced pressure and water was added. The layers were separated and the aqueous extracted (3×) with ethyl acetate. The combined organic layers were dried with anhydrous magnesium sulfate, filtered and concentrated and used with no further purification.

The crude protected material was dissolved in ethyl acetate (15 mL) and HCl (g) was bubbled through the solution for 2 min. The reaction mixture was purged with nitrogen and poured onto a mixture of ethyl acetate and water. The layers were separated and the aqueous extracted (3×) with ethyl acetate. The combined organic layers were dried with anhydrous magnesium sulfate, filtered and concentrated. Purification by flash column chromatography (methylene chloride:methanol:ammonium hydroxide 97:3:0.3) gave N-[4-(2,2-difluoro-2-phenylethoxy)-3-fluorocyclohexyl]-1H-pyrazolo[3,4-d]pyrimidin-4-amine (67 mg, 75% yield) as a white solid: mp=184-185° C.; $^1$H NMR (400 MHz, CDCl$_3$) δ 12.13 (s, br, 1H), 8.44 (s, 1H), 7.91 (s, 1H), 7.54-7.2 (m, 2H), 7.47-7.41 (m, 3H), 5.48 (br s, 1H), 4.61 (d of multiplets, J=48.8 Hz, 1H), 4.35 (br s, 1H), 4.11 (dd, J=26.3, 12.8 Hz, 1H), 4.01 (dd, J=25.1, 12.6 Hz, 1H), 3.65-3.55 (m, 1H), 2.51-2.42 (m, 1H), 2.07 (m, 2H), 1.73 (m, 1H) 1.62-1.42 (m, 3H) ppm; HRMS (APCI) m/z 392.1713 [(M+H)$^+$; calcd for C$_{19}$H$_{21}$F$_3$N$_5$O: 392.1693].

Step 5: N-[4-(2,2-difluoro-2-phenylethoxy)-3-fluoro-cyclohexyl]-1H-pyrazolo[3,4-d]pyrimidin-4-amine

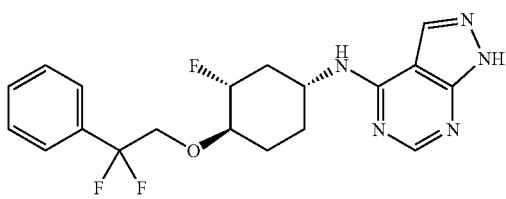

The (+) enantiomer of N-[4-(2,2-difluoro-2-phenylethoxy)-3-fluorocyclohexyl]-1H-pyrazolo[3,4-d]pyrimidin-4-amine, was prepared from (+) 2-{[4-(Benzyloxy)-2-fluorocyclohexyl]oxy}-1-phenylethanone, following the identical reaction sequence described with respect to the (−) enantiomer to give N-[4-(2,2-difluoro-2-phenylethoxy)-3-fluorocyclohexyl]-1H-pyrazolo[3,4-d]pyrimidin-4-amine as a white solid: mp=178-179° C.; $^1$H NMR (400 MHz, CDCl$_3$) δ 8.40 (s, 1H), 7.88 (s, 1H), 7.49 (m, 2H), 7.41 (m, 3H), 5.45 (br s, 1H), 4.61 (d of multiplets, J=46.5 Hz, 1H), 4.31 (br s, 1H), 4.08 (dd, J=25.2, 12.6 Hz, 1H), 3.96 (dd, J=25.2, 12.6 Hz, 1H), 3.56 (m, 1H), 2.44 (m, 1H), 2.01 (m, 2H), 1.69-1.22 (m, 4H) ppm; HRMS (APCI) m/z 392.1682 [(M+H)$^+$; calcd for C$_{19}$H$_{21}$F$_3$N$_5$O: 392.1693].

EXAMPLE 78

(1S,3S)-N-[2,2-difluoro-2-(4-methylphenyl)ethyl]-N'-1H-pyrazolo[3,4-d]pyrimidin-4-ylcyclopentane-1,3-diamine

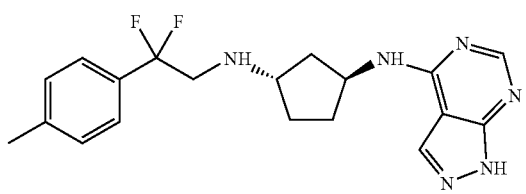

Step 1: benzyl tert-butyl (1S,3S)-cyclopentane-1,3-diylbiscarbamate

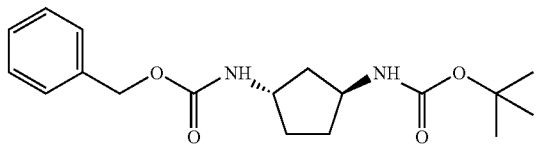

Diphenylphosphoryl azide (1.90 mL, 8.82 mmol) was added to a stirred mixture of (1S,3S)-3-[(tert-butoxycarbonyl)amino]cyclopentanecarboxylic acid (1.359 g, 5.93 mmol) and Et$_3$N (1.65 mL, 11.84 mmol) in dry toluene (27.5 mL) and the resulting mixture was heated to 90° C. for 3 h. Benzyl alcohol (3.4 mL, 32.8 mmol) and DMAP (67 mg, 0.55 mmol) were added and the mixture was heated for an additional 16 h. The mixture was cooled and the solids were collected by filtration, rinsing with 1:1 toluene:hexane (4 mL), and dried to give the title compound as a white solid (1.649 g). The mother liquors were purified by silica gel chromatography (5% CH$_2$Cl$_2$, 10-80% EtOAc/hexane gradient), to give additional product (0.386 g). The combined solids are 88 area % pure at 215 nm; MS=235.3 (M+1-isobutylene and CO$_2$).

Step 2: tert-butyl [(1S,3S)-3-aminocyclopentyl]carbamate

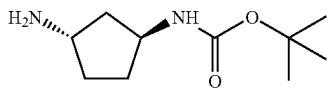

A mixture of benzyl tert-butyl (1S,3S)-cyclopentane-1,3-diylbiscarbamate (2.02 g, 6.04 mmol) and 10% Pd/C (142 mg) in EtOH (200 mL) was shaken on a Parr apparatus under hydrogen (36 psi) for 1 hr. The reaction mixture was filtered through celite and concentrated to give the title compound (1.37 g) as an opaque paste.

Step 3: ethyl difluoro(4-methylphenyl)acetate

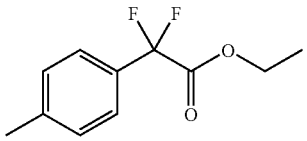

The compound was prepared by modification to the procedure of Sato, K.; Kawata, R.; Ama, F.; Omote, M.; Ando, A. Chemical & Pharmaceutical Bulletin 47(7), 1013-1016 (1999). To a solution of 1-iodo-4-methylbenzene (25.1 g, 115 mmol) in DMSO (125 mL) was added ethyl bromo(difluoro)acetate (24.7 g, 122 mmol) and copper (16.8 g, 264 mmol), and the resulting solution was heated to 55° C. After 14 h the reaction was cooled to room temperature and diluted with isopropyl acetate, then cooled to 0° C. and treated with a solution of potassium hydrogen phosphate (23.3 g) in water (250 mL). The mixture was filtered through a pad of Celite, rinsing with isopropyl acetate. The phases were separated and the aqueous layer was washed with isopropyl acetate. The combined organic layers were washed with brine, dried (sodium sulfate), filtered and concentrated. The residue was purified by silica gel chromatography (5% methylene chloride, 1-8% ethyl acetate/hexanes gradient) gave the title compound (17.2 g) as an oil.

Step 4: tert-butyl (1S,3S)-3-{[difluoro(4-methylphenyl)acetyl]amino}cyclopentylcarbamate

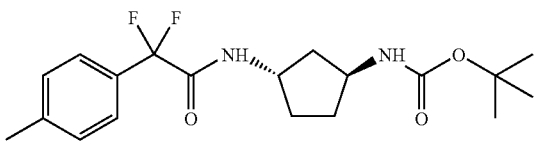

A solution of tert-butyl [(1S,3S)-3-aminocyclopentyl]carbamate (1.36 g, 6.8 mmol) and ethyl difluoro(4-methylphenyl)acetate (1.45 g, 6.8 mmol) in EtOH (5 mL) was stirred at reflux for 16 h. The solution was cooled to rt. whereupon it solidified. Et$_2$O (6 mL) and hexane (3 mL) were added and the mixture was stirred for 3 h and the solids collected by filtration, rinsing with Et$_2$O (2 mL), and dried to give the title compound (1.051 g) as a solid; MS=313.4 (M+1-isobutylene).

Step 5: N-[(1S,3S)-3-aminocyclopentyl]-2,2-difluoro-2-(4-methylphenyl)acetamide

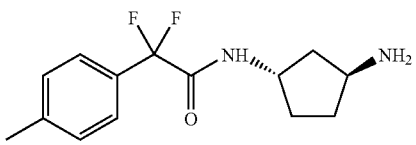

A saturated solution of HCl in EtOAc (10 mL) was added to a stirred solution of tert-butyl (1S,3S)-3-{[difluoro(4-methylphenyl)acetyl]amino}cyclopentylcarbamate (1.05 g, 2.85 mmol) in EtOAc (10 mL). After 1 h the solution was concentrated to dryness. The residue was dissolved in 1:1 CH$_3$CN/H$_2$O (18 mL) and loaded onto SCX ion exchange resin (10 g, 60 mL, 6.9 meq), rinsing with CH$_3$CN (15 mL), and then eluting with EtOH/NH$_3$ (25 mL). The eluent was concentrated to give the title compound (774 mg) as a solid: MS=252.4 (M+1-ammonia).

Step 6: (1S,3S)-N-[2,2-difluoro-2-(4-methylphenyl)ethyl]cyclopentane-1,3-diamine

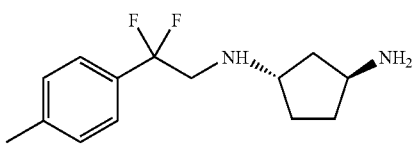

1M borane in THF (20 mL, 20 mmol) was added slowly to a stirred solution of N-[(1S,3S)-3-aminocyclopentyl]-2,2-difluoro-2-(4-methylphenyl)acetamide (1.006 g, 3.749 mmol) in dry THF (20 mL) at 0° C. The reaction mixture was warmed to rt. and then was heated to 70° C. for 1 h. The reaction mixture was cooled, quenched with 6N HCl (2.5 mL, 15 mmol) and stirred at rt for 16 h. Aqueous sodium carbonate was added to pH=11, and the mixture was extracted with EtOAc, dried (MgSO$_4$), filtered and concentrated. The resulting oil was purified by silica gel chromatography (eluting with 1.2% NH$_4$OH/10.8% MeOH/CHCl$_3$) to give the title compound as a pale yellow oil (627 mg): MS=255.4 (M+1).

Step 7: (1S,3S)-N-[2,2-difluoro-2-(4-methylphenyl)ethyl]-N'-[2-(tetrahydro-2H-pyran-2-yl)-2H-pyrazolo[3,4-d]pyrimidin-4-yl]cyclopentane-1,3-diamine

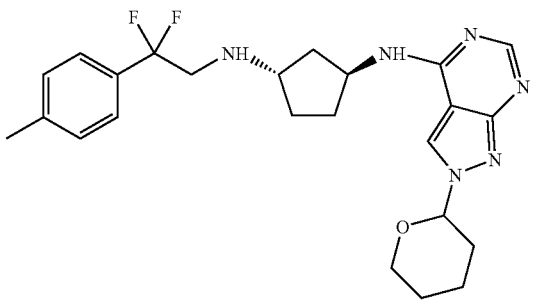

A mixture of (1S,3S)-N-[2,2-difluoro-2-(4-methylphenyl)ethyl]cyclopentane-1,3-diamine (627 mg, 2.46 mmol), 4-chloro-2-(tetrahydro-2H-pyran-2-yl)-2H-pyrazolo[3,4-d]pyrimidine (588 mg, 2.46 mmol), n-butanol (1.6 mL) and diisopropylethylamine (1.6 mL) was heated in microwave for 15 min at 150° C. The reaction mixture was concentrated in vacuo to a viscous brown oil, which was purified by silica gel chromatography (CH$_2$Cl$_2$/MeOH gradient) to give the title compound (0.982 g) as a cream colored foam: MS=457.4 (M+1).

Step 8: (1S,3S)-N-[2,2-difluoro-2-(4-methylphenyl)ethyl]-N'-1H-pyrazolo[3,4-d]pyrimidin-4-ylcyclopentane-1,3-diamine

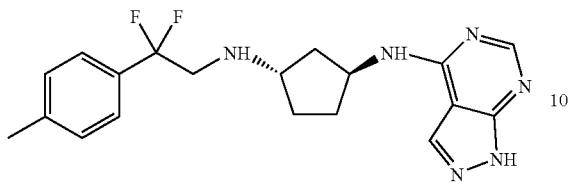

A saturated solution of HCl in EtOAc (4 mL) was added to a stirred solution of (1S,3S)-N-[2,2-difluoro-2-(4-methylphenyl)ethyl]-N'-[2-(tetrahydro-2H-pyran-2-yl)-2H-pyrazolo[3,4-d]pyrimidin-4-yl]cyclopentane-1,3-diamine (0.665 g, 1.46 mmol) in EtOAc (8 mL). After 20 min the mixture was concentrated to dryness and the residue was purified by reverse phase HPLC ($C_8$, eluting with 0.1% TFA, acetonitrile/water gradient) to give the TFA salt of the title compound (179 mg) as a hygroscopic foam: MS=373.4 (M+1); $^1$H NMR (400 MHz, $CD_3OD$) δ 1.91 (m, 2H), 2.36-2.50 (m, 4H), 2.42 (s, 3H), 3.91 (t, J=15.7 Hz, 2H), 4.00 (m, 1H), 4.99 (m, 1H), 7.38 (d, J=8.0 Hz, 2H), 7.53 (d, J=8.0 Hz, 2H), 8.59 (s, 1H), 8.62 (s, 1H).

EXAMPLE 79

4-({trans-4-[(2R)-2-fluoro-2-(2-fluorophenyl)ethoxy]cyclohexyl}amino)-1H-pyrazolo[3,4-d]pyrimidin-6-ol

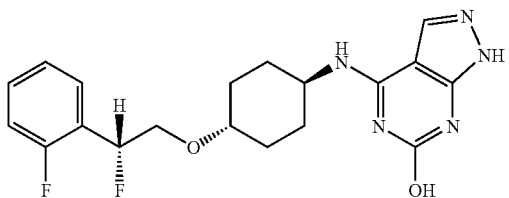

From trans-4-[(2R)-2-fluoro-2-(2-fluorophenyl)ethoxy]cyclohexanamine, the resolved product of Example 11, Step 8, and 4-(methylthio)-1H-pyrazolo[3,4-d]pyrimidin-6-ol [R. K. Robins, J. Am. Chem. Soc. 79, (1957), 6407-15] in refluxing 2-propanol/water for several days: MS (m+1)=390.4; 1H NMR (400 MHz, CDCl3-CD3OD) 8.2 (s, 1H), 8.0 (s, 1H), 7.5 (m, 1H), 7.4 (dd, 1H), 7.2 (t, 1H), 7.1 (t, 1H), 5.85 (dd, JHF=47 Hz, 1H), 4.2 (m, 1H), 3.75 (m, 2H), 3.4 (m, 1H), 2.7 (m, 1H), 2.1 (m, 2H), 1.4 (m, 2H).

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound having the formula (I):

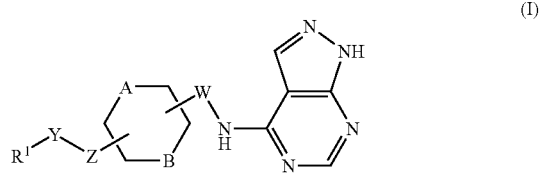

(I)

wherein:

$R^1$ is selected from:

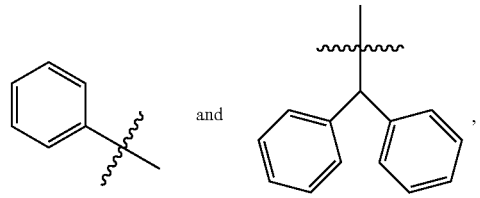

and unsubstituted or substituted with one or more substituents selected from: halogen, —$R^2$, —O—$R^2$, —CN, —N($R^2$)$_2$, Y is selected from:

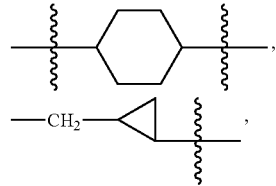

wherein the $CH_2$ moiety is bound to Z and the cyclopropyl moiety is bound to $R^1$,

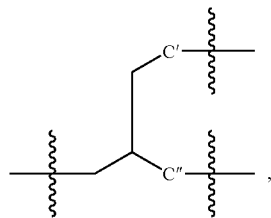

—$R^3$— and —$R^3$—O—$R^3$—, where C' and C" are each independently directly or indirectly bound to an $R^1$ phenyl ring to form a 5 to 7 member fused ring;

Z is absent or is selected from O, $C_{1-6}$alkylene, $C_{1-6}$alkenylene, C(O), S, SO, $SO_2$, $NR^4$, where $R^4$ is hydrogen, $C_{0-6}$alkyl or $C_{0-6}$alkenyl, where said alkyl, alkenyl, alkylene or alkenylene is unsubstituted or is substituted with one or more substituents selected from: halogen, —R⁵, —O—R⁵, —CN, —N(R⁵)₂;

A and B are each independently $C_{0-4}$alkyl, where a ring is formed comprising A and B, where each member of said ring is independently unsubstituted or substituted with one or more substituents selected from halogen, —R⁶, —O—R⁶, —CN, —N(R⁶)₂;

W is absent or is selected from O, $C_{0-6}$alkylene, $C_{0-6}$alkenylene, C(O), S, SO, SO₂, NR⁷, where said alkyl, alkenyl, alkylene or alkenylene is unsubstituted or is substituted with one or more substituents selected from halogen, —R⁸, —O—R⁸, —CN, —N(R⁸)₂;

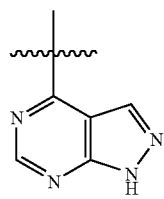

is unsubstituted or is substituted with one or more substituents selected from halogen, —R⁹, —O—R⁹, —CN, —N(R⁹)₂;

R², R³, R⁴, R⁵, R⁶, R⁷, R⁸ and R⁹ are each independently hydrogen, $C_{0-6}$alkyl, $C_{0-6}$alkenyl unsubstituted or substituted with one or more halogen;

or a pharmaceutically acceptable salt thereof, or an individual diastereomer thereof.

2. A compound of claim 1, wherein:

R¹ is

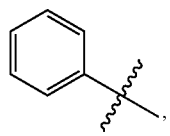

unsubstituted or substituted with halogen or —R², where R² is $C_{1-6}$alkyl;

Y is —$C_{1-6}$alkyl, independently unsubstituted or substituted with one or more halogen;

Z is O;

A and B are each independently $C_{0-4}$alkyl;

W is absent;

or a pharmaceutically acceptable salt thereof or an enantiomer or diastereomer thereof.

3. A compound having the formula (Ia):

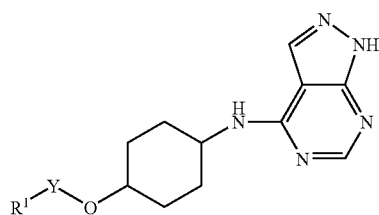

(Ia)

wherein:

R¹ is

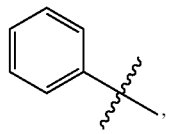

unsubstituted or substituted with halogen or —R², where R² is $C_{1-6}$alkyl, independently unsubstituted or substituted with one or more halogen;

Y is —$C_{1-6}$alkyl, independently unsubstituted or substituted with one or more halogen;

or a pharmaceutically acceptable salt thereof or an enantiomer or diastereomer thereof.

4. A compound having the formula (Ib):

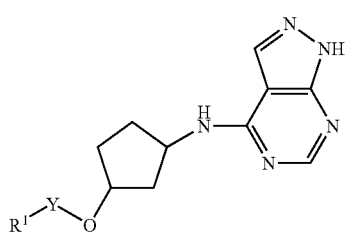

(Ib)

wherein:

R¹ is

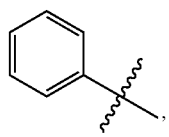

unsubstituted or substituted with halogen or —R², where R² is $C_{1-6}$alkyl, unsubstituted or substituted with one or more halogen;

the cyclopentyl group is unsubstituted or substituted with 1-3 fluorine;

Y is —$C_{1-6}$alkyl, unsubstituted or substituted with one or more halogen;

or a pharmaceutically acceptable salt thereof or an enantiomer or diastereomer thereof.

5. A compound having the formula (Ic):

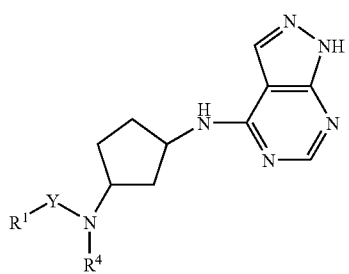

(Ic)

wherein:

R¹ is

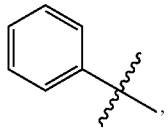

unsubstituted or substituted with halogen or —R², where R² is $C_{1-6}$alkyl, unsubstituted or substituted with one or more halogen;

R⁴ is hydrogen or $C_{0-6}$alkyl unsubstituted or substituted with one or more halogen;

the cyclopentyl group is unsubstituted or substituted with 1-3 fluorine;

Y is —$C_{1-6}$alkyl, unsubstituted or substituted with one or more halogen;

or a pharmaceutically acceptable salt thereof or an enantiomer or diastereomer thereof.

6. A compound of claim 1 selected from:

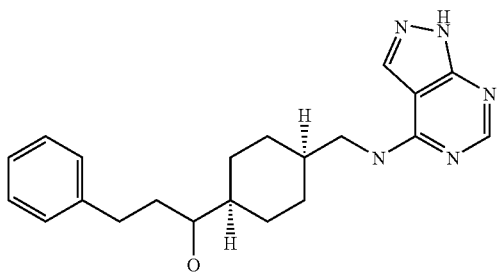

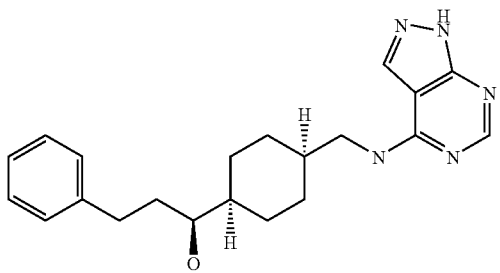

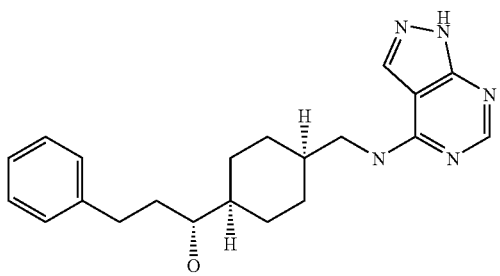

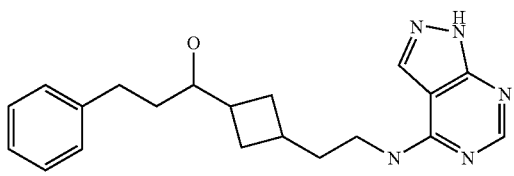

-continued

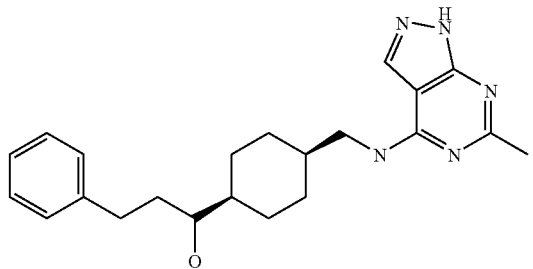

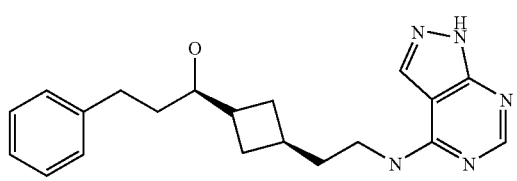

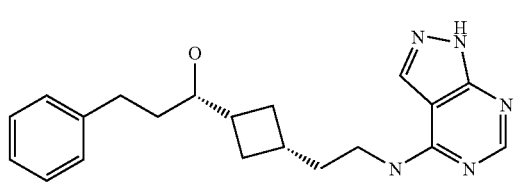

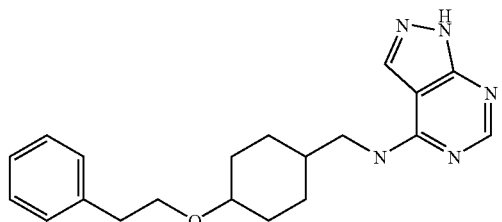

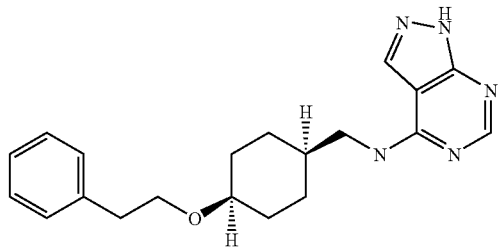

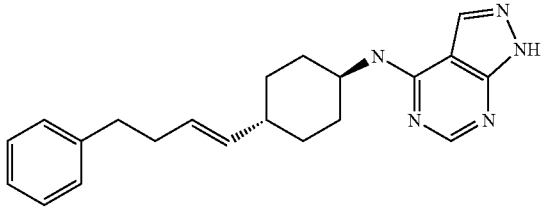

131
-continued
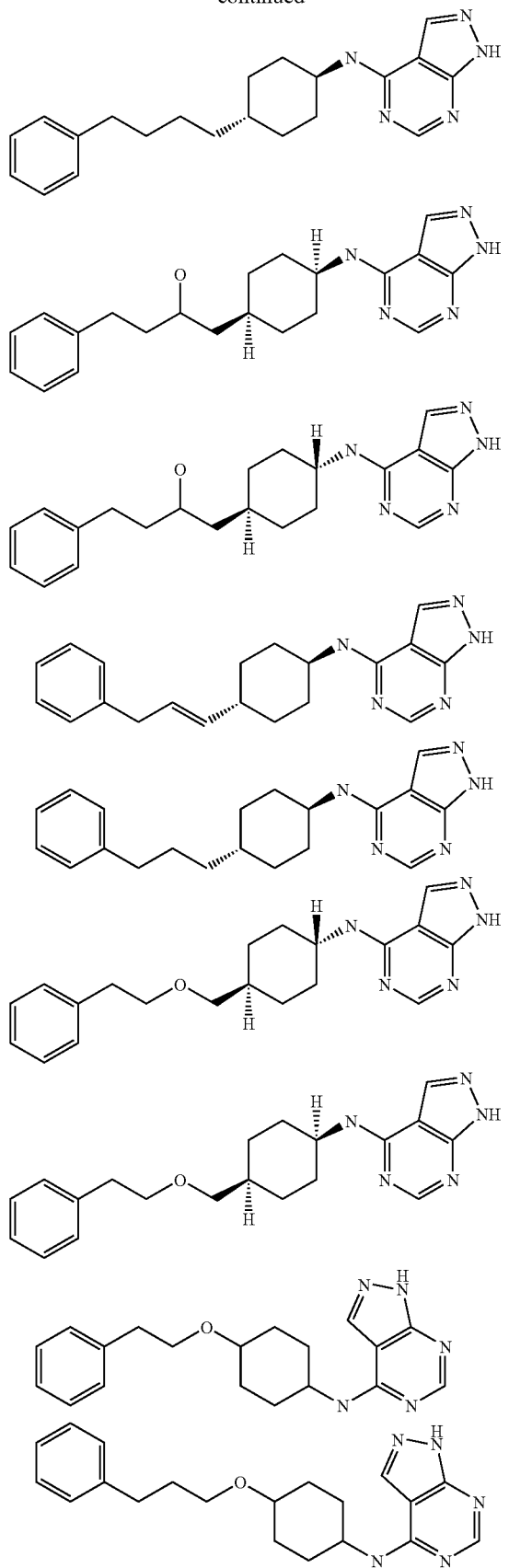
132
-continued
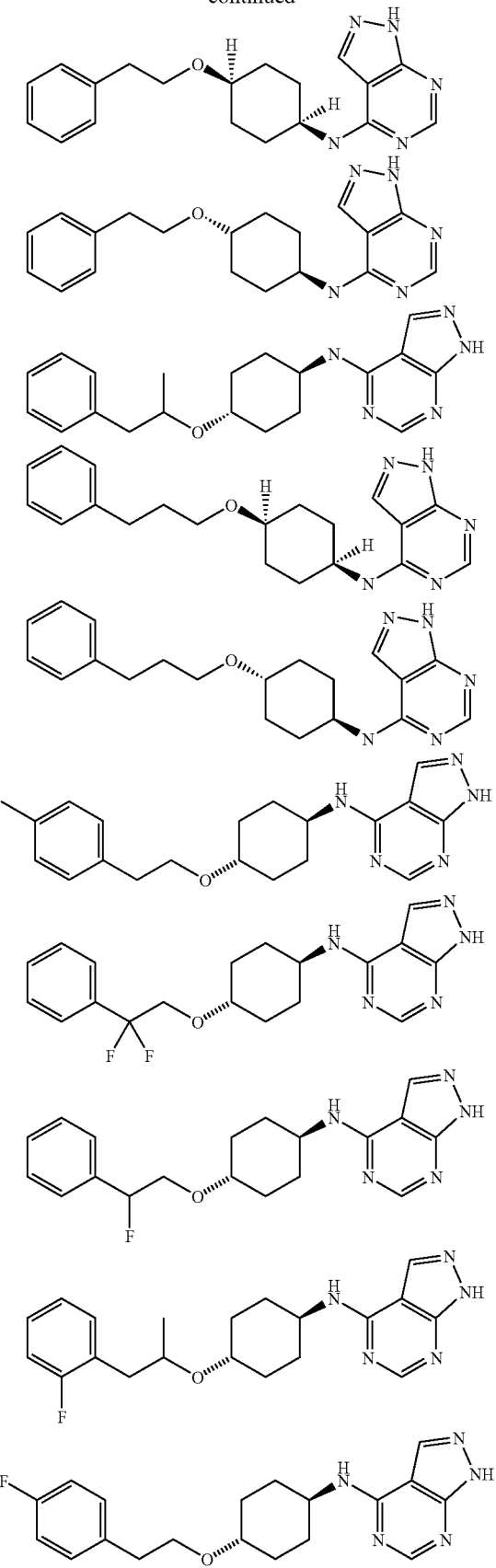

133
-continued
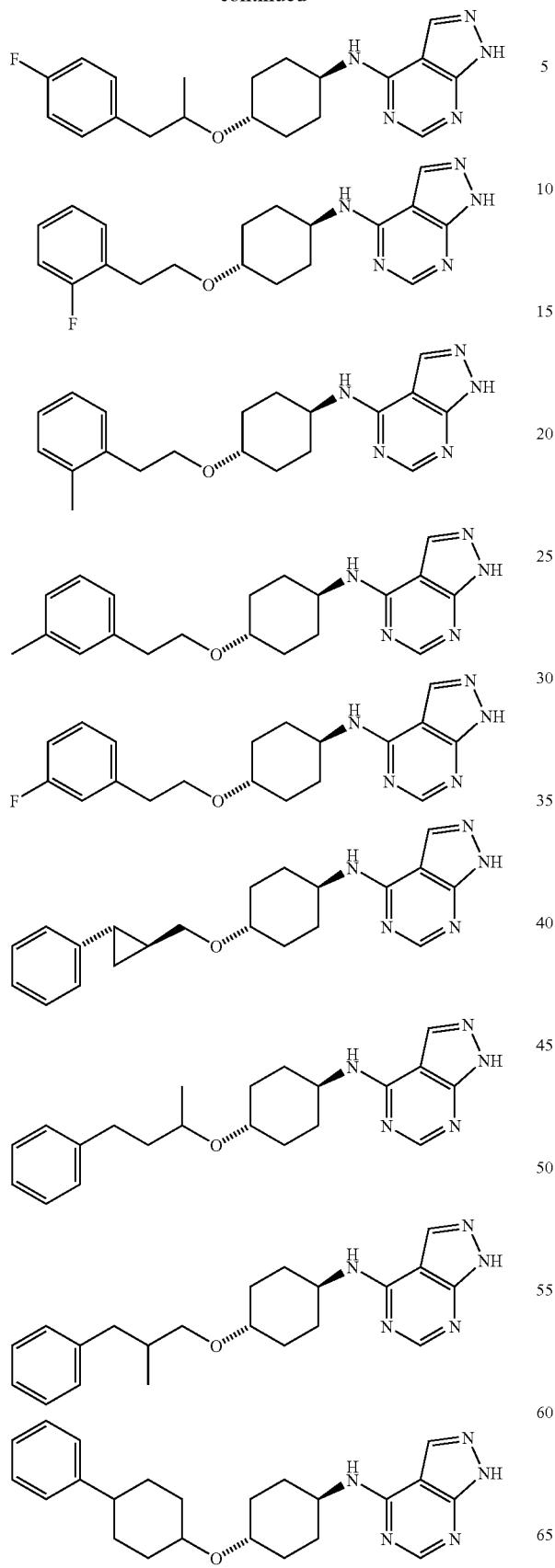
134
-continued
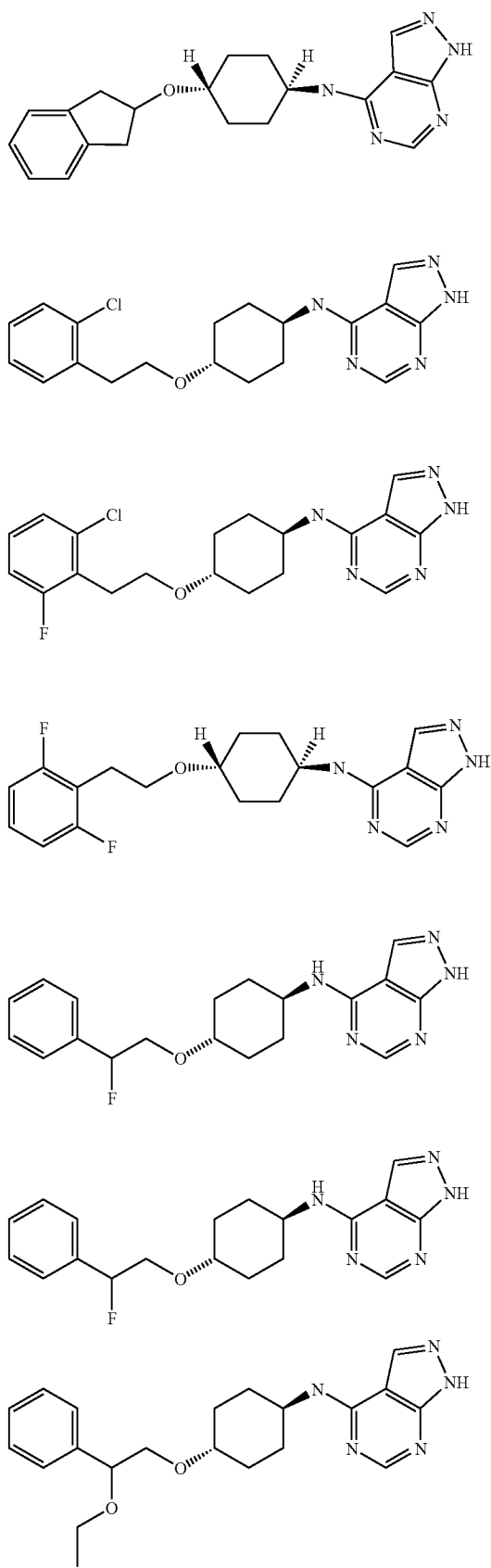

135
-continued
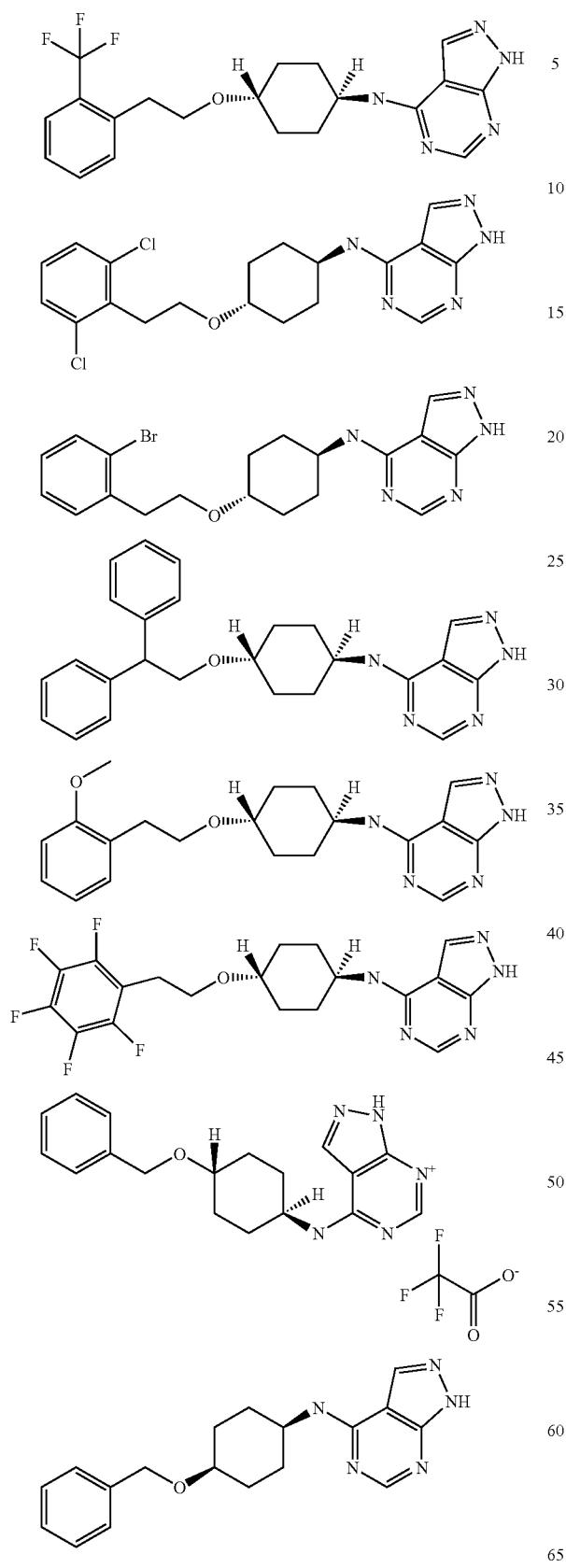
136
-continued
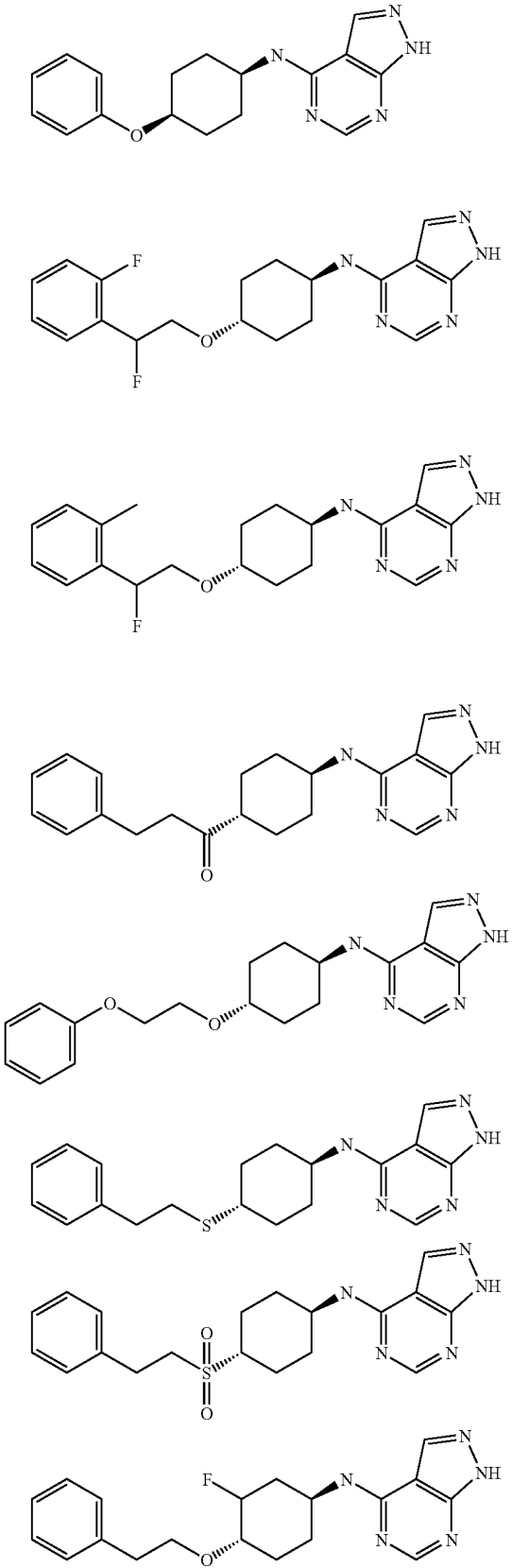

-continued

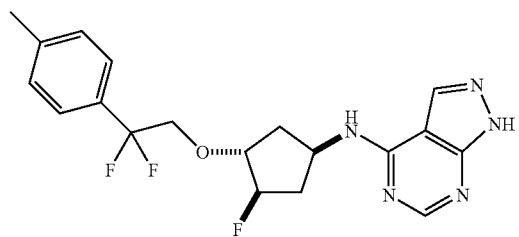
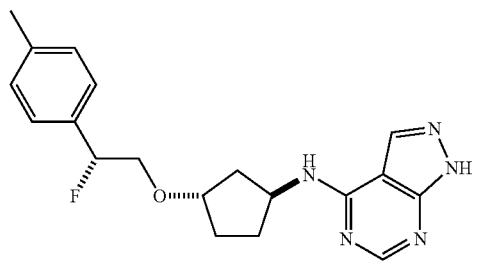
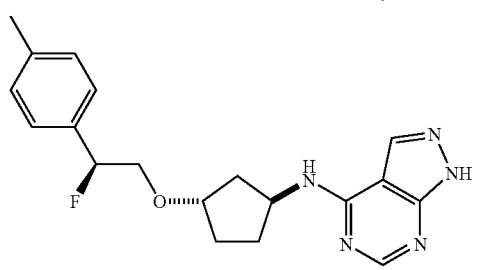
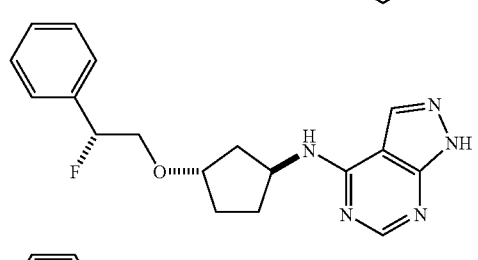
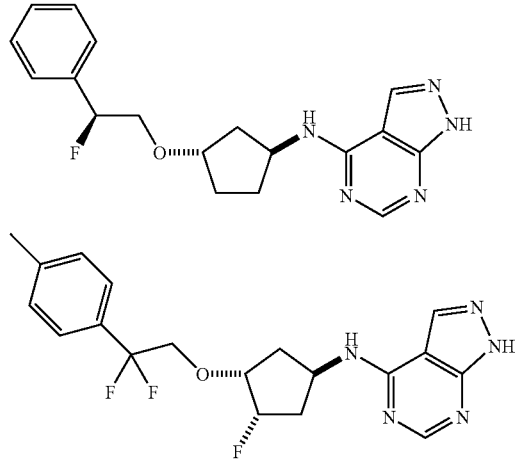
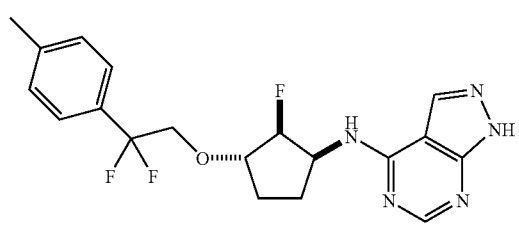
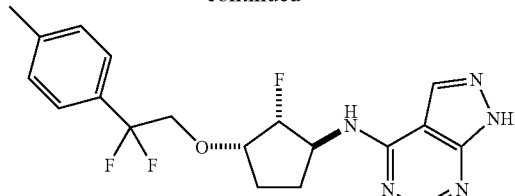
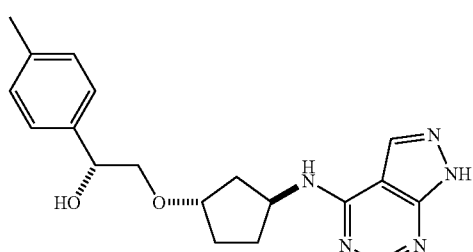
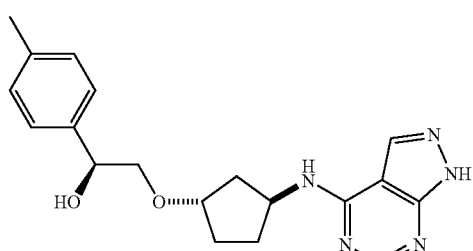
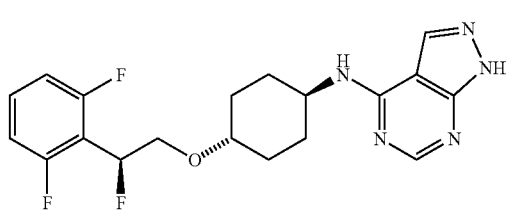
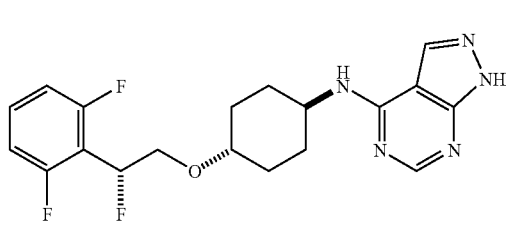
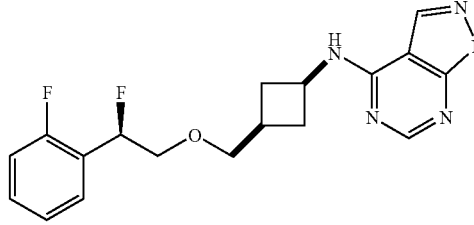
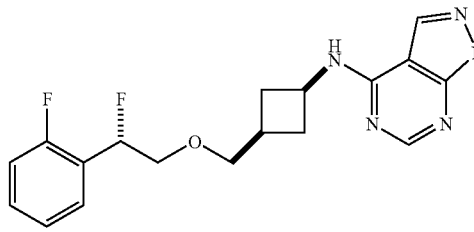

141
-continued
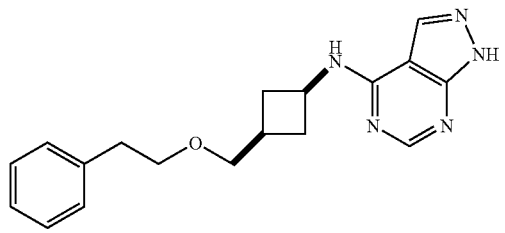
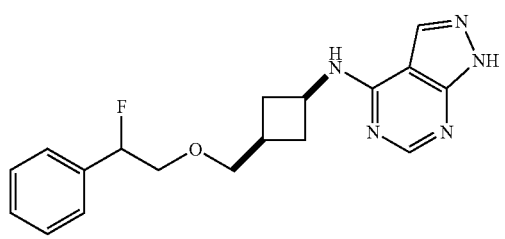
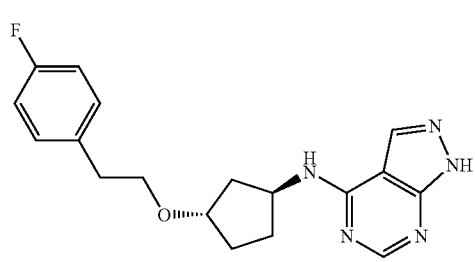
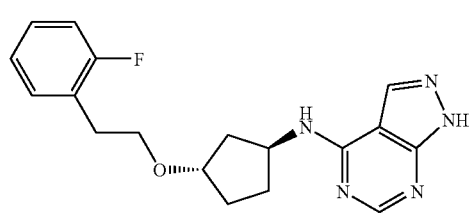
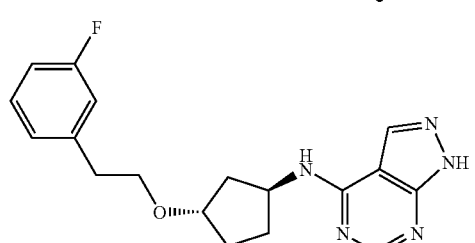
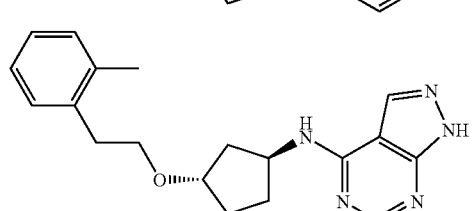
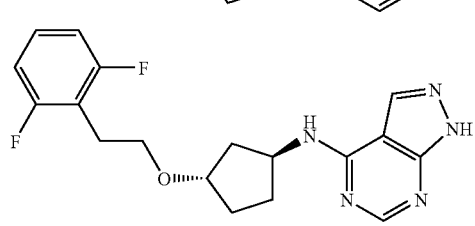
142
-continued
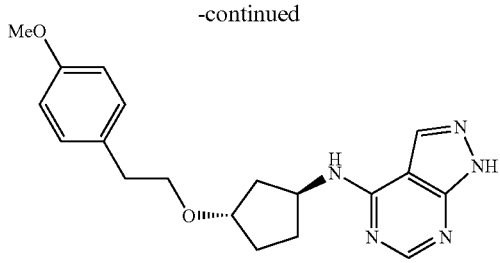
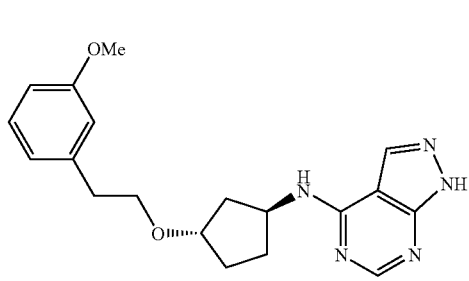
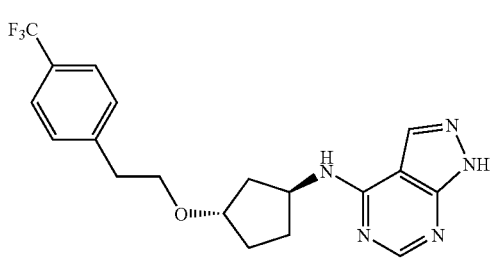
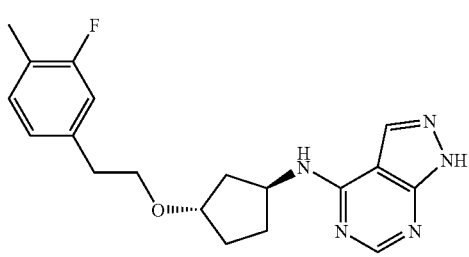
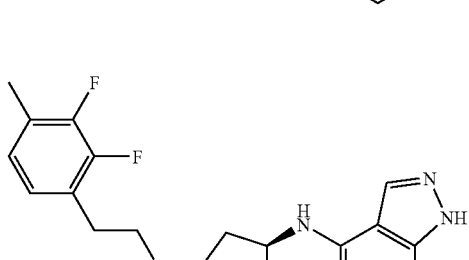
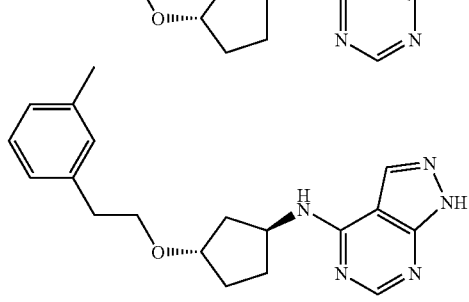

-continued
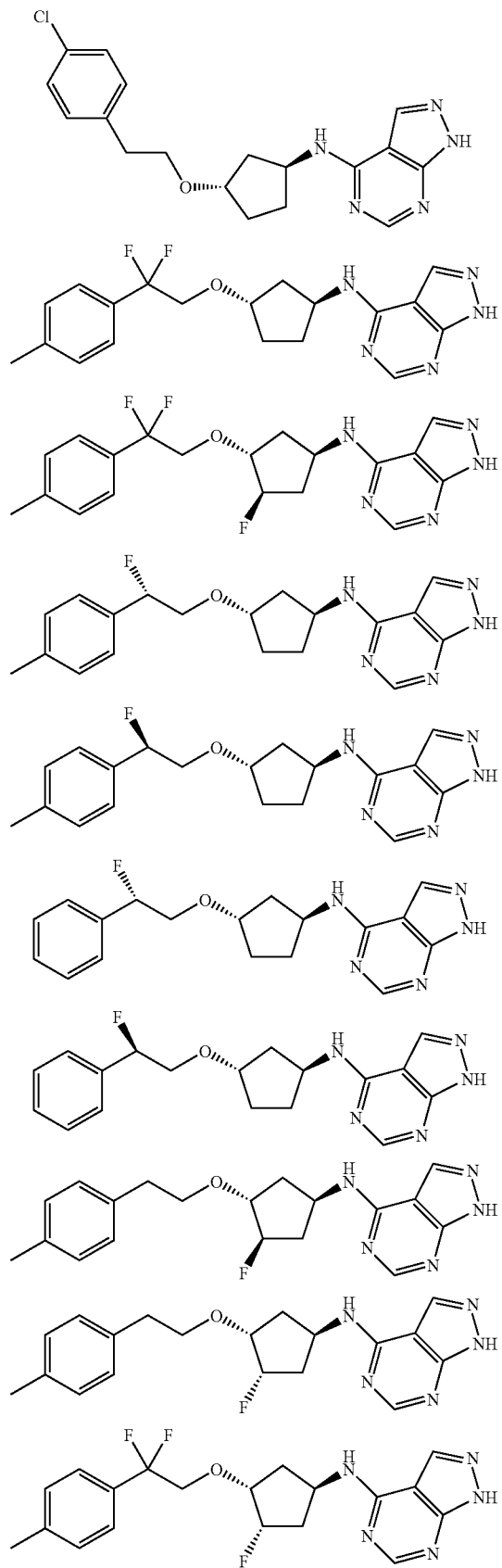
-continued
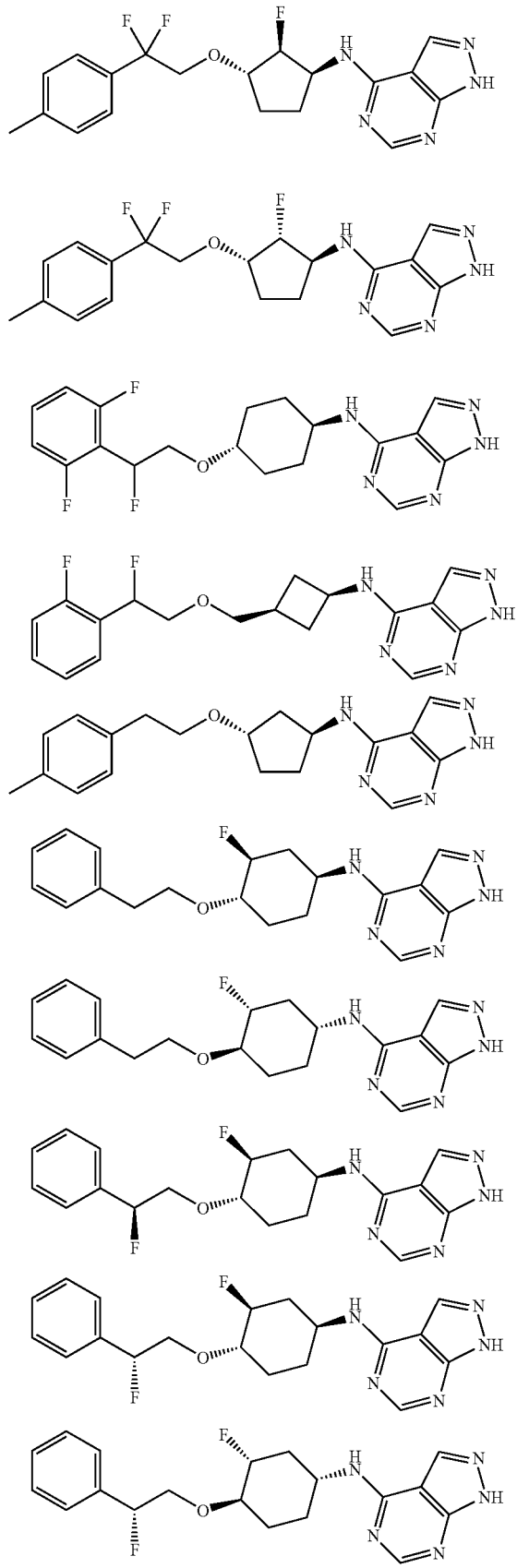

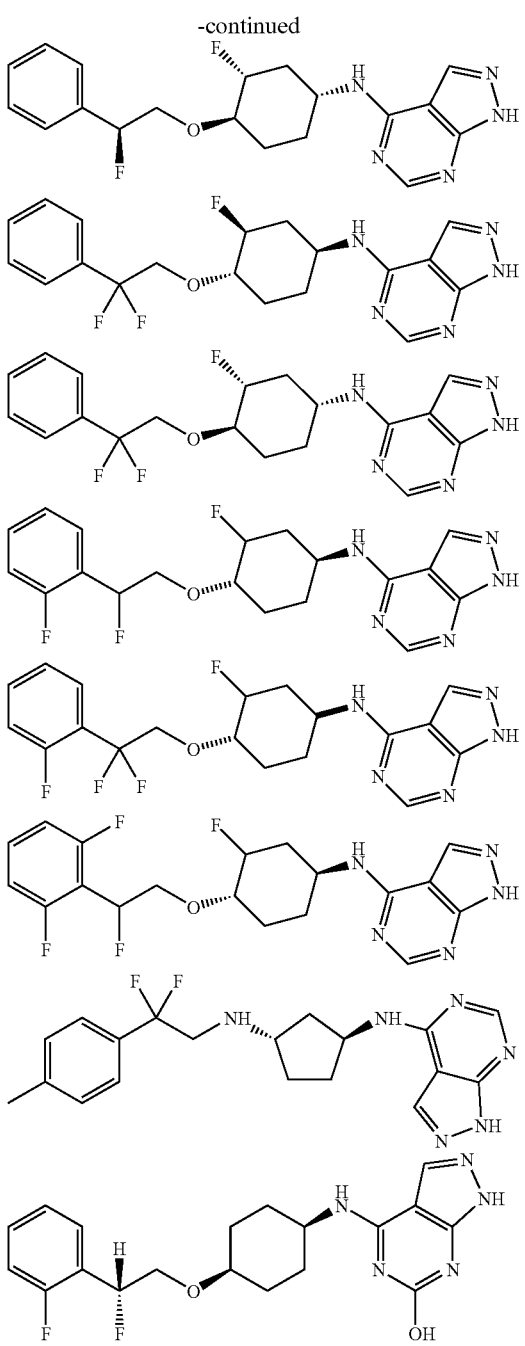

or a pharmaceutically acceptable salt thereof, or an enantiomer or diastereomer thereof.

7. A pharmaceutical composition comprising an inert carrier and a therapeutically effective amount of a compound according to claim 1.

8. The pharmaceutical composition according to claim 7, further comprising a second therapeutic agent selected from the group consisting of: (i) non-steroidal anti-inflammatory agents; (ii) COX-2 inhibitors; (iii) bradykinin B1 receptor antagonists; (iv) sodium channel blockers and antagonists; (v) nitric oxide synthase (NOS) inhibitors; (vi) glycine site antagonists; (vii) potassium channel openers; (viii) AMPA/ kainate receptor antagonists; (ix) calcium channel antagonists; (x) GABA-A receptor modulators (e.g., a GABA- A receptor agonist); (xi) matrix metalloprotease (MMP) inhibitors; (xii) thrombolytic agents; (xiii) opioids such as morphine; (xiv) neutrophil inhibitory factor (NIF); (xv) L-Dopa; (xvi) carbidopa; (xvii) levodopa/carbidopa; (xviii) dopamine agonists such as bromocriptine, pergolide, pramipexole, ropinirole; (xix) anticholinergics; (xx) amantadine; (xxi) carbidopa; (xxii) catechol O-methyltransferase ("COMT") inhibitors such as entacapone and tolcapone; (xxiii) Monoamine oxidase B ("MAO-B") inhibitors; (xiv) opiate agonists or antagonists; (xv) 5HT receptor agonists or antagonists; (xvi) NMDA receptor agonists or antagonists; (xvii) NK1 antagonists; (xviii) selective serotonin reuptake inhibitors ("SSRI") and/or selective serotonin and norepinephrine reuptake inhibitors ("SSNRI"); (xxix) tricyclic antidepressant drugs, (xxx) norepinephrine modulators; (xxxi) lithium; (xxxii) valproate; and (xxxiii) neurontin (gabapentin).

9. A compound selected from

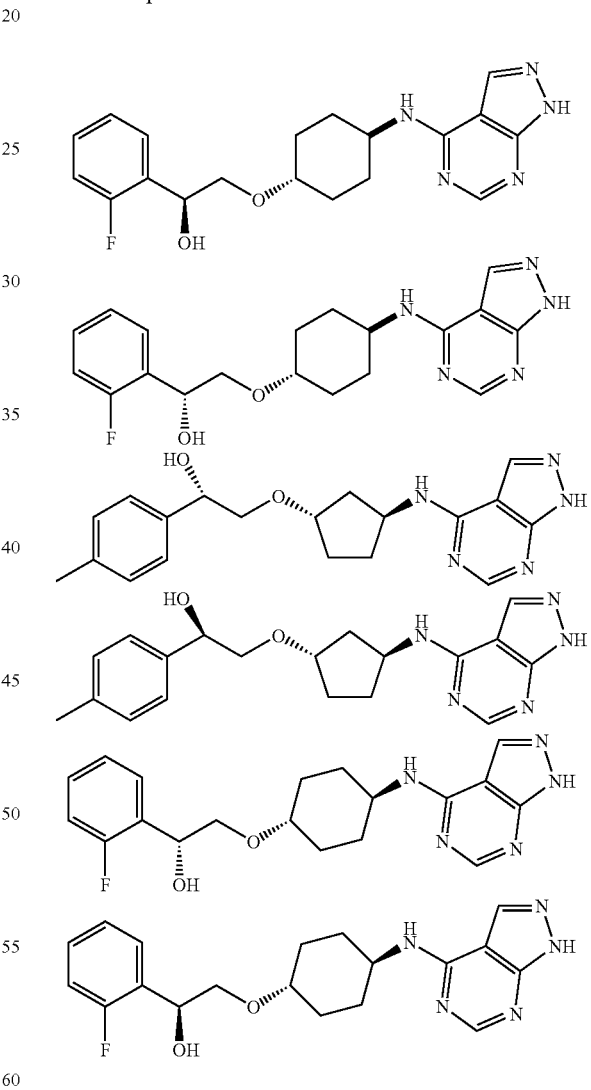

or a pharmaceutically acceptable salt thereof, or an enantiomer or diastereomer thereof.

* * * * *